US005202315A

United States Patent [19]

Kim et al.

[11] Patent Number: 5,202,315

[45] Date of Patent: Apr. 13, 1993

[54] CEPHALOSPORIN COMPOUNDS

[75] Inventors: Yong Z. Kim; Hun S. Oh; Jae H. Yeo; Jong C. Lim; Won S. Kim; Chan S. Bang; Hyeon J. Yim, all of Daejeon-si, Rep. of Korea

[73] Assignee: Lucky, Ltd., Seoul, Rep. of Korea

[21] Appl. No.: 494,163

[22] Filed: Mar. 15, 1990

[30] Foreign Application Priority Data

| | | | |
|---|---|---|---|
| May 11, 1989 | [KR] | Rep. of Korea | 89-6431 |
| Jun. 7, 1989 | [KR] | Rep. of Korea | 89-7827 |
| Jun. 7, 1989 | [KR] | Rep. of Korea | 89-7828 |
| Jul. 28, 1989 | [KR] | Rep. of Korea | 89-10755 |
| Feb. 5, 1990 | [KR] | Rep. of Korea | 90-1351 |

[51] Int. Cl.[5] .................. C07D 501/36; A61K 31/545

[52] U.S. Cl. .................................... 514/206; 540/227; 540/226

[58] Field of Search ................ 540/227, 202; 514/206, 514/202

[56] References Cited

FOREIGN PATENT DOCUMENTS

| | | |
|---|---|---|
| 0029901 | 6/1981 | European Pat. Off. . |
| 0047977 | 3/1982 | European Pat. Off. . |
| 0062321 | 10/1982 | European Pat. Off. . |
| 0074563 | 3/1983 | European Pat. Off. . |
| 1399086 | 6/1975 | United Kingdom . |
| 1522140 | 8/1978 | United Kingdom . |

*Primary Examiner*—Nicholas S. Rizzo

*Attorney, Agent, or Firm*—Birch, Stewart, Kolasch & Birch

[57] ABSTRACT

The present invention relates to new cephalosporin compounds of the formula(I), pharmaceutically acceptable non-toxic salts thereof, and physiologically hydrolyzable esters and solvates thereof, which have potent and broad antibacterial activities

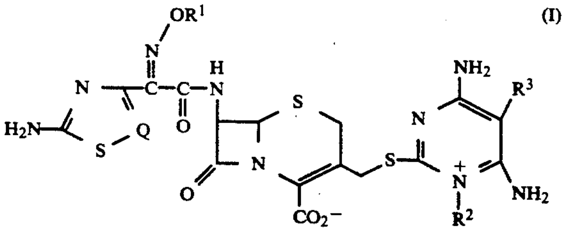

(I)

wherein $R^1$ is a $C_{1\sim4}$ alkyl, $C_{3\sim4}$ alkenyl, $C_{3\sim4}$ alkynyl group, or $-C(R^a)(R^b)CO_2H_1$ wherein $R^a$ and $R^b$ are the same or different, and each is a hydrogen atom or a $C_{1\sim4}$ alkyl group, or $R^a$ and $R^b$ form a $C_{3\sim7}$ cycloalkyl group with the carbon atom to which they are linked;

$R^2$ is a $C_{1\sim4}$ alkyl, $C_{3\sim4}$ alkenyl or $C_{3\sim4}$ cycloalkyl group, a substituted or unsubstituted amino group, or a substituted or unsubstituted phenyl group;

$R^3$ is hydrogen or a $C_{1\sim4}$ alkyl group; and

Q is N or CH.

The invention further relates to a process for preparing said compounds, and to pharamaceutical compositions containing said compounds.

58 Claims, No Drawings

CEPHALOSPORIN COMPOUNDS

FIELD OF THE INVENTION

The present invention relates to novel cephalosporin compounds, pharmaceutically acceptable non-toxic salts thereof, and physiologically hydrolyzable esters, hydrates and solvates thereof, which possess potent and broad antibacterial activities. The invention also relates to processes for preparing the same, and to pharmaceutical compositions containing the same as active ingredients.

BACKGROUND OF THE INVENTION

Antibiotics of cephalosporin series are widely used in therapy for treatment of diseases which are caused by general pathogenic bacteria in human beings and animals. It has been known that such antibiotics are useful for the treatment of diseases caused by bacteria exhibiting the resistance to other antibiotics, e.g. penicillin-resistant bacteria, and for treatment of penicillin-sensitive patients.

In most circumstances it is desirable to employ antibiotics showing broad antibacterial activities against both Gram-positive and Gram-negative bacteria. In this regard, there have been made many studies in developing a variety of cephalosporin antibiotics with broad-spectrum antibiotic activities.

For example, in GB patent No. 1,399,086 there are disclosed many cephalosporin derivatives which are shown by the formula

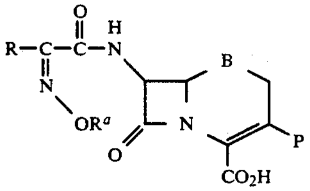

(A)

wherein

R is hydrogen or an organic group;

$R^a$ is an etherifying monovalent organic group linked to the oxygen atom through a carbon atom;

B is —S— or

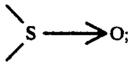

and

P is an organic group.

After the invention of these compounds, there were many attempts to develop antibiotic compounds having more improved properties, to a certain bacteria especially to Gram-negative bacteria.

GB patent No. 1,522,140 discloses cephalosporin antibiotic compounds of the formula(B) which exist as syn isomers, or as a mixture of syn and anti isomers wherein the syn isomers are present in at least 90%,

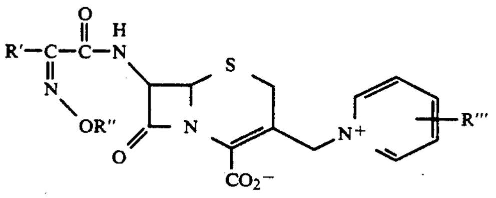

(B)

wherein

R′ is a furyl or thienyl group;

R″ is a $C_{1\sim4}$ alkyl, $C_{3\sim7}$ cycloalkyl, furylmethyl or thienylmethyl group; and R‴ is hydrogen or a carbamoyl, carboxymethyl, sulfonyl or methyl group.

The foregoing cephalosporin compounds have high antibacterial activities against a range of Gram-positive and Gram-negative bacteria, and particularly high stability to β-lactamases produced by various Gram-negative bacteria. Moreover, they are very stable in vivo.

Recently, there have been efforts to prepare new antibiotics having more improved and broadened antibiotic spectrum and while showing potent antibiotic activities, especially against Gram-negative bacteria. Consequently a large number of cephalosporin antibiotics with analogous structures to those above, have been developed.

As a part of said efforts, an acylamido group has been introduced into the 7-position of the cephem nucleus as shown in the foregoing formula(B) and a certain groups have been introduced into the 3-position thereof.

For example, in BE patent No. 852,427 there are reported a number of cephalosporin compounds having antibiotic activities which are shown by the foregoing formula(A) wherein the R is substituted with various organic groups including 2-aminothiazol, the oxygen atom of the oxyimino group, is directly bonded to an aliphatic hydrocarbon group, and which aliphatic hydrocarbon group may be itself substituted with a carboxy group. The substituent in 3-position of such compounds is an acetoxymethyl, hydroxymethyl, formyl group, or an optionally substituted hetero cyclic thiomethyl group.

Also, in U.S. Pat. No. 4,390,534 to Psutomu Terachi et al, there are reproted new cephem compounds of the formula

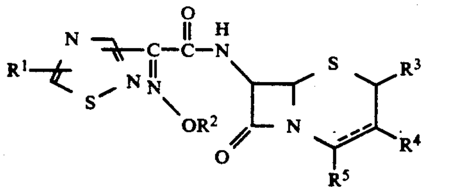

(C)

wherein $R^1$ is amino or a protected amino group;

$R^2$ is hydrogen, acyl, substituted or unsubstituted aryl, substituted alkyl, alkenyl, alkynyl, substituted or unsubstituted cycloalkyl, cycloalkenyl, or O- or S-containing 5-membered hetero cyclic group;

$R^3$ hydrogen or alkyl;

$R^4$ is an acyloxyalkyl, acylthioalkyl, substituted or unsubstituted pyridiniumalkyl, substituted or unsubstituted heterocyclic thioalkyl, alkyl, hydroxy, or substituted or unsubstituted thiazoliumalkyl group, or halogen;

$R^5$ is carboxy or a protected carboxy group, wherein $R^5$ is $COO^-$ when $R^4$ is a substituted or unsubstituted pyridiniumalkyl group or a substituted or unsubstituted thiazoliumalkyl group; and the dotted line "- - - " represents a single bond or a double bond.

While the P of the aforesaid GB patent No. 1,399,086 or the $R^4$ of the aforesaid U.S. Pat. No. 4,390,534 are defined very broadly as an organic group or a substituted or unsubstituted heterocyclic thioalkyl group, respectively, there is not therein mentioned the heart of the present invention that is a compound having a (1-substituted-4,6-diaminopyrimidinium-2-yl) thiomethyl group introduced into 3-position of the cephem nucleus.

Also, European patent application No. 62,321 discloses cephem compounds of the formula(D) and pharmaceutically acceptable salts thereof, and their intermediates of the formula(D')

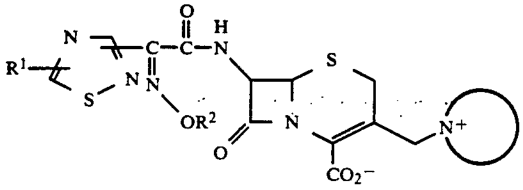
(D)

wherein $R^1$ is amino or a protected amino group;

$R^2$ is a substituted or unsubstituted lower aliphatic hydrocarbon group, or a cycloalkenyl group; and

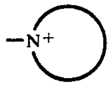

is a substituted or unsubstituted heterocyclic cation group containing one or more nitrogen atoms;

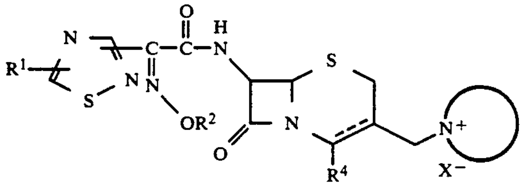
(D')

wherein $R^1$ and $R^2$ are the same as defined in the formula(D), respectively;

$R^4$ is a protected carboxyl group; and $X^-$ is an acid residue.

In European patent application NO. 74,563, the cephem compounds of the formula(E) and their salts are proposed as antibiotic compounds

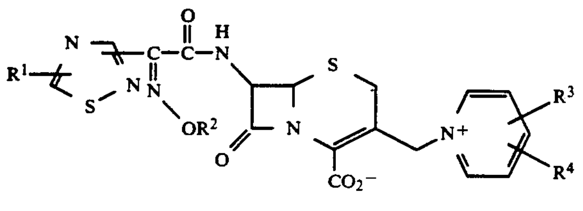
(E)

wherein $R^1$ is amino or a protected amino group;

$R^2$ is a protected or unprotected lower aliphatic hydrocarbon group, cyclo(lower)alkyl, or cyclo(lower)alkenyl group;

$R^3$ is (lower)alkylamino, N-protected(lower)alkylamino, di(lower) alkylamino, sulfo(lower)alkylamino, hydroxy(lower)alkylamino, N-protected hydroxy(lower)alkylamino, acyloxy(lower)alkyl, (lower)alkoxy(lower)alkoxy(lower)alkyl, di(lower)alkylamino (lower)alkyl, (lower)alkylthio(lower)alkyl, (lower)alkylthio, (lower)alkoxy(lower)alkoxy, (lower)alkoxy, hydroxy(lower)alkoxy, acyl(lower)alkyl, hydroxy(lower)alkylthio, di(lower)alkylamino (lower)alkylthio, N-containing unsaturated 5-membered heterocyclic group, N-containing unsaturated 5-membered heterocyclic thio group, or N-containing unsaturated 5- or 6-membered heterocyclic (lower)alkyl group which may be optionally substituted with suitable substituent(s); and $R^4$ is hydrogen or a (lower)alkyl group.

There are disclosed cephem compounds of the formula(F) and their salts in European patent application No. 47,977

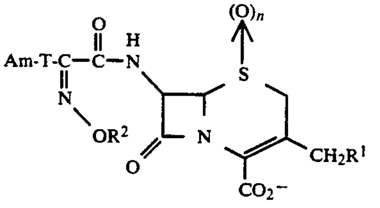
(F)

wherein n is an integer of 0 or 1;

Am is amino or a substituted amino group;

T is a thiadiazoly moiety, where one carbon atom is bonded to Am and the other carbon atom is bonded to the group of —C(=N—O—$R^2$)—;

$R^2$ is hydrogen, a substituted or unsubstituted carbamoyl group, a cycloalkyl group, or a substituted or unsubstituted carbamoyl group; and $R^1$ is a substituted or unsubstituted thiazolium group, a substituted or unsubstituted pyrazolium group, a tri(lower)alkyl ammonium group or a pyridinium group of the following formula

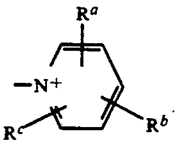

[wherein $R^a$ is (lower)alkyl [which is substituted with a substituent selected from the group consisting of cycloalkyl, methyl, hydroxy, alkoxy, halogen, cyano, carbamoyl, carboxyl and sulfonyl], (lower)alkenyl or carboxy-substituted (lower)alkenyl, (lower)alkylthio or carboxy-substituted (lower)alkylthio, amino or mono-substituted amino [wherein the substituent is selected from the group consisting of (lower) alkyl, (lower)alkanoyl or aminobenzenesulfonyl], di(lower)alkylamino, carbamoyl [which is substituted by (lower)alkyl, hydroxy(-lower)alkyl, (lower)alkoxy, hydroxy or cyano], di(lower)alkylcarbamoyl, thiocarbamoyl, cycloalkyl, phenyl, hydroxy, (lower)alkoxy, halogen, (lower)alkoxycarbonyl, (lower)alkanoyloxy, (lower)alkanoyl, carboxy, sulfocyano, nitro, a hydroxysulfo(lower)alkyl group];

$R^b$ is hydrogen, a carbamoyl group, or a group selected from the groups defined for the $R^a$; and $R^c$ is hydrogen or a group selected from the groups as defined in the $R^a$.

As described above, there are a variety of cephem compounds whose 7-positions are substituted by a substituted aminothiadiazole ring. However, there are no reports about the most important characteristic of the present invention that is a (1-substituted-4,6-diaminopyrimidinium-2-yl)thiomethyl group is introduced into the 3-position of the cephem nucleus.

SUMMARY OF THE INVENTION

An objective of the present invention is to provide new antibiotic cephalosporin compounds of the formula(I), pharmaceutically acceptable non-toxic salts thereof, and metabolically labile esters and solvates thereof (I)

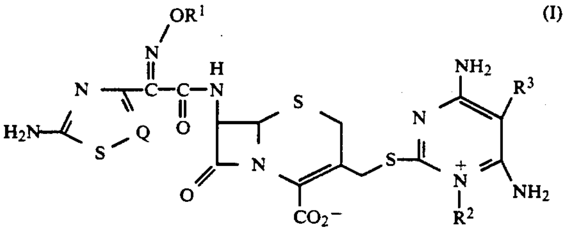

wherein $R^1$ is a $C_{1\sim4}$ alkyl (preferably methyl or ethyl), $C_{3\sim4}$ alkenyl (preferably allyl), $C_{3\sim4}$ alkynyl (preferably propargyl) group, or $—C(R^a)(R^b)CO_2H$ wherein, $R^a$ and $R^b$ or different, are a hydrogen atom or a $C_{1\sim4}$ alkyl group, or $R^a$ and $R^b$ form a $C_{3\sim7}$ cycloalkyl group with the carbon atom to which they are linked;

$R^2$ is a $C_{1\sim4}$ alkyl (preferably a straight alkyl group such as methyl, ethyl, n-propyl or n-butyl), $C_{3\sim4}$ alkenyl (preferably allyl), $C_{3\sim7}$ cycloalkyl, substituted or unsubstituted amino or substituted or unsubstituted phenyl (preferably phenyl, 4-hydroxyphenyl, 4-chlorophenyl, 3,4-dimethylphenyl, 2,4-dimethylphenyl or 2,6-dimethyoxyphenyl) group;

$R^3$ is hydrogen or a $C_{1\sim4}$ alkyl group(preferably methyl or ethyl); and Q is N or CH.

Another objective of the present invention is to provide processes for preparing the cephalosporin compounds of formula (I).

A further objective of the present invention is to provide pharmaceutical compositions comprising one or more of the cephalosporin compounds of formula(I) as active ingredients.

DETAILED DESCRIPTION OF THE INVENTION

The new cephalosporin compounds of the present invention are either syn isomers or mixtures of syn and anti isomers which contain at least 90% of the syn isomer and not more than 10% of the anti isomer. Also, when the $R^1$ group of formula(I) compounds is $—C(-R^a)(R^b)CO_2H$ wherein $R^a$ and $R^b$ are different, the carbon atom to which $R^a$ and $R^b$ are linked becomes an asymmetrical center, these compounds being diastereoisomers. Therefore, the present invention also includes such diastereoisomers of cephalosporin compounds of formula (I), and mixtures thereof.

Also, the solvates including hydrates of the compounds(I) are included within the scope of the invention. In addition, the compounds of the formula(I) according to the present invention may exist in tautomeric forms and such tautomers are also included within the scope of the invention. Namely, when the Q of the formula (I) is a carbon atom, the aminothiazolyl group undergoes tautomerism to form a iminothiazolinyl group, its tautomer, as follows:

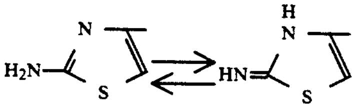

When the Q of the formula (I) is a nitrogen atom, the aminothiadiazolyl group forms iminothiadiazolinyl groups, its tautomers, by tautomerism as follows:

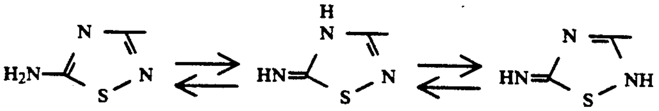

The compounds of the formula (I) also include the following resonance structures (I') and (I''):

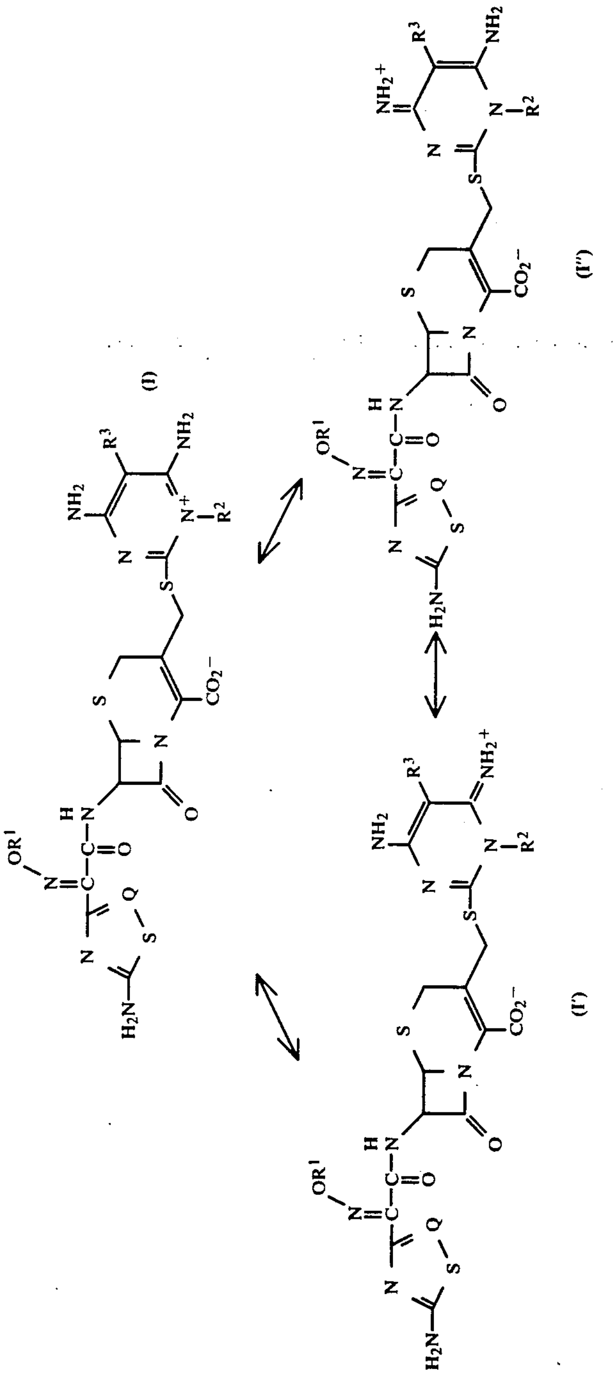
(I) (I') (I'')

Suitable pharmaceutically acceptable salts of the object compounds (I) are conventional non-toxic salts and may include an inorganic salt, for example, a metal salt such as an alkali metal salt(e.g., sodium salt, potassium salt, etc.) and an alkaline earth metal salt(e.g., calcium salt, magnesium salt, etc.), ammonium salt, etc.; an organic salt, for example, an organic amine salt(e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino) methane salt, phenylethylbenzylamine salt; dibenzylethylenediamine salt, etc.) etc.; an organic carboxylic or sulfonic acid salt(e.g., formate, acetate, maleate, tartrate, methanesulfonate, benzenesulfonate, toluenesulfonate etc.); an inorganic acid salt(e.g., hydrochloride, hydrobromide, sulfate, phosphate, etc.); a salt with a basic or acidic amino acid(e.g., arginine, aspartic acid, glutamic acid, lysine, etc.) and the like.

The physiologically hydrolyzable esters of the compounds (I) may include, for example, indanyl, phthalidyl, methoxymethyl, pivaloyloxymethyl, glycyloxymethyl, phenylglycyloxymethyl or 5-methyl-2-oxo-1,3-dioxolan-4-yl esters, and other physiologically hydrolyzable esters which have been widely used in the technical fields of penicillin and cephalosporin antibiotics. These esters can be prepared in accordance with known methods.

The cephalosporin compounds of the formula(I) exhibit high antibacterial activities against both Gram-positive and Gram-negative bacteria, and are especially useful in the theraphy for therapeutic and prophylactic treatment of bacterial infections in human beings and animals.

The present invention also includes within its scope pharmaceutical compositions comprising one or more of the compounds(I) according to the present invention as active ingredients, in association with pharmaceutically acceptable carriers, excipients or other additives.

The antibiotic compounds(I) of the invention may be formulated for administration, which may be presented in unit dose form or in multidose containers. The compositions may take various forms such as solutions, suspensions or emulsions in oily or aqueous vehicles, which can contain conventional additives such as dispersing agents, suspending agents, stabilizing agents, and the like. Alternatively, the active ingredient may be formed into a dried powder that can be normally dissolved in an aqueous solution of sterile, pyrogen-free water, before use. The compounds(I) may be also formulated into suppositories containing conventional suppository bases such as cocoa butter or other glycerides.

The pharmaceutical compositions in unit dose form preferably comprise about from 50 to 1,500 mg of the active ingredient, depending on the age and body weight of the patient, the nature and the severity of the illness, and so on. In general it has proved advantageous to administer the active compounds in an amount of about 500 to 5,000 mg per day in order to achieve the desired results, depending on the routes and frequency of administration. In case of intramuscular or intravenous administrations for adult human treatment, the dose of about 150 to 3,000 mg per day is thought sufficient, and but it may be increased in case of treatment for specific infections caused by some strains.

If desired, the compounds(I) can be administered in combination with other antibiotics such as penicillins or other cephalosporins.

The compounds of the present invention as described above, exhibit potent and broad antibacterial activities against Gram-positive bacteria and a variety of Gram-negative bacteria as well, particularly against Pseudomonas. Also, these compounds have high stability to $\beta$-lactamases produced by a number of Gram-negative bcteria.

Examples of especially preferred compounds(I) are the compounds(I-1) and (I-15) of the formula(I) wherein $R^1$ is $-C(CH_3)_2CO_2H$, $R^2$ is methyl or amino, $R^3$ is hydrogen, and Q is CH, and their pharmaceutically acceptable non-toxic salts. These compounds(I-1) and (I-15) posseses excellent antibacterial activities, especially against Pseudomonas.

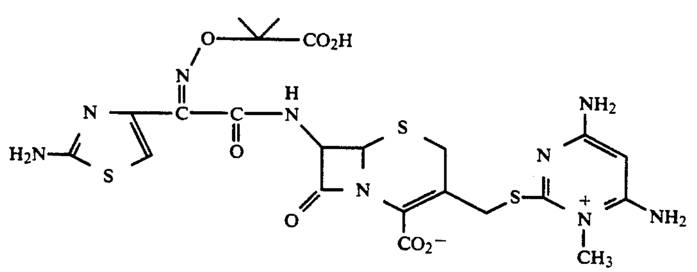

(I-1)

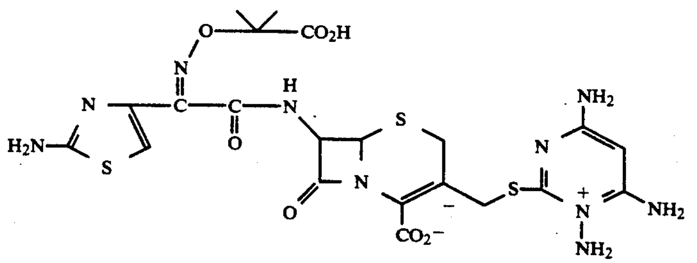

(I-15)

Further examples of preferred compounds(I) of the present invention are as follows:

| $R^1$ | $R^2$ | $R^3$ | Q |
|---|---|---|---|
| $-C(CH_3)_2CO_2H$ | $-CH_3$ | H | CH |
| $-C(CH_3)_2CO_2H$ | $-CH_2CH_3$ | H | CH |
| $-C(CH_3)_2CO_2H$ | $-NH_2$ | H | CH |

-continued

| $R^1$ | $R^2$ | $R^3$ | Q |
|---|---|---|---|
| $—C(CH_3)_2CO_2H$ | $—CH_3$ | $—CH_3$ | CH |
| $—CH(CH_3)CO_2H$ | $—CH_3$ | H | CH |
| $—CH(CH_3)CO_2H$ | $—CH_2CH_3$ | H | CH |
| $—CH(CH_3)CO_2H$ | $—CH_2CH_2CH_3$ | H | CH |
| $—C(CH_3)CO_2H$ | $—NH_2$ | H | CH |
| $—CH_2C{\equiv}CH$ | $—CH_3$ | H | CH |
| $—CH_2C{\equiv}CH$ | $—CH_2CH_3$ | H | CH |
| $—CH_2C{\equiv}CH$ | $—NH_2$ | H | CH |
| $—CH_2CH_3$ | $—NH_2$ | H | CH |
| $—CH_2CH_3$ | $—CH_2$ | H | N |
| $—CH_2CH_3$ | $—NH_2$ | H | N |
| $—CH_2CO_2H$ | $—CH_3$ | H | CH |
| $—CH_3CO_2H$ | $—CH_2CH_3$ | H | CH |

The cephalosporin compounds(I), pharmaceutically acceptable non-toxic salts thereof, or physiologically hydrolyzable esters or solvats(including hydrates) thereof may be prepared by reacting the compounds of the formula (II) with the compounds of the formula(III) in the presence of a solvent, and then, if necessary, removing the amino protecting group and/or the carboxyl protecting group and/or reducing S-oxide [that is, $S{\rightarrow}(O)_n$] by a known method, before or after said reaction. This process also constitutes a further aspect of the invention.

roethyl), tetrahydropyranyl, substituted phenylthio, substituted alkylidene, substituted aralkylidene or substituted cyclolidene. The acyl group as an amino protecting group may include, for example, $C_{1\sim6}$ (lower) alkanoyl (e.g. formyl and acetyl), $C_{2\sim6}$ alkoxycarbonyl-(e.g. methoxycarbonyl and ethoxycarbonyl), (lower)alkanesulfonyl (e.g. methanesulfonyl and ethanesulfonyl), or aryl (lower)alkoxycarbony(e.g. benzyloxycarbonyl), where the acyl group can be substituted by $1\sim3$ substituent(s) such as halogen, hydroxy, cyano or nitro. In addition, the amino protecting group may include reaction products obtained from amino groups and silane, boron or phosphorus compounds.

The carboxyl protecting group as $R^c$ of $R^5$ or $R^6$ may include for example, (lower)alkylesters (e.g. methylester and t-butylester), (lower) alkenylesters(e.g. vinylester and allylester), (lower)alkoxy(lower) alkylesters-(e.g. methoxymethylester), (lower)alkylthio(lower-)alkylesters (e.g. methylthiomethylester), halo(lower-)alkylesters(e.g. 2,2,2-trichloroethylester), substituted or unsubstituted aralkylesters(e.g. benzylester and p-nitrobenzylester) or silylesters, which can be selected after consideration of the chemical property of the desired compounds(I).

It is desired that the aforementioned amino or carboxyl protecting groups may be readily removed under

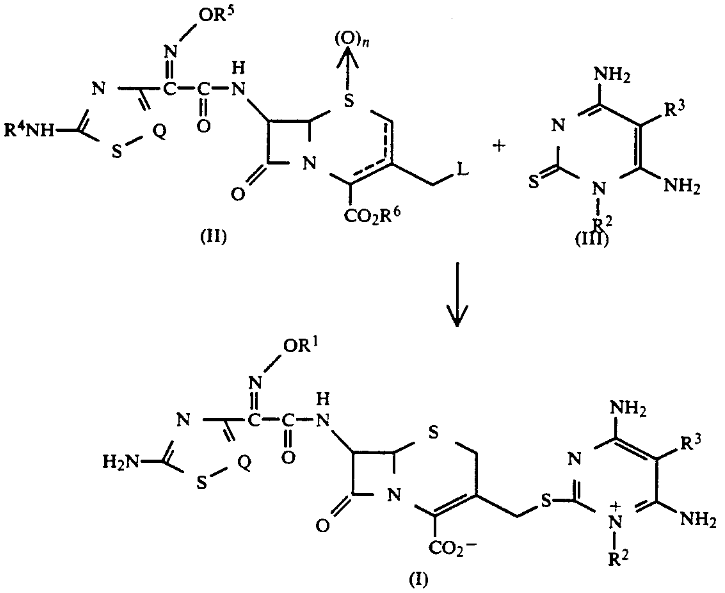

(II) (III) (I)

Wherein $R^1$, $R^2$, $R^3$ and Q are the same as defined above;

n is an integer of 0 or 1;

$R^4$ is hydrogen or an amino protecting group;

$R^5$ is a $C_{1\sim4}$ alkyl, $C_{3\sim4}$ alkenyl or $C_{3\sim4}$ alkynl group, or $—C(R^a)(R^b)CO_2(R^c)$ wherein $R^a$ and $R^b$ same or different are a hydrogen atom or a $C_{1\sim4}$ alkyl group, or $R^a$ and $R^b$ may form a $C_{3\sim7}$ cycloalkyl group with the carbon atom to which they are linked; and $R^c$ is hydrogen or a carboxyl protecting group;

$R^5$ is a hydrogen atom or a carboxyl protecting group; and

L is a leaving group.

The amino protecting group may include acyl, substituted or unsubstituted aryl (lower)alkyl(e.g. benzyl, diphenylmethyl, triphenylmethyl and 4-methoxybenzyl), halo(lower)alkyl(e.g. trichloromethyl and trichlomild reaction conditions by a known method.

The leaving group L may include, for example, halogen such as chlorine or fluorine, an (lower)alkanoyloxy group such as acetoxy, a (lower)alkanesulfonyloxy group such as methanesulfonyloxy, an arenesulfonyloxy group such as p-toluenesulfonyloxy, an alkoxycarbonyloxy groups and the like.

The starting materials of the compounds(II) are known as intermediates conventionally employed for the preparation of cephalosporin compounds. The dotted line of the formula(II) represents a single bond or a double bond and, therefore, the compounds of the formula(II) may be the compounds of the formula(II-a), or compounds of the formula (II-b), or mixtures thereof:

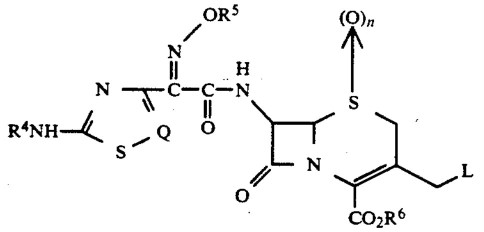

(II-a)

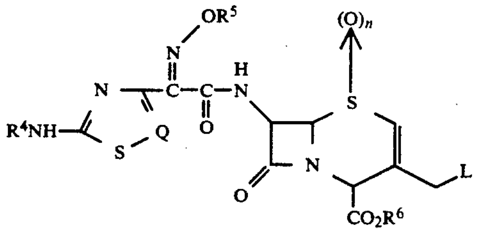

(II-b)

wherein
n, $R^4$, $R^5$, $R^6$, Q and L are the same as defined above.

The compounds of the formula(II) can be prepared by activating the compounds of the formula(IV) or their salts with an acylating agent, and reacting with the compounds of the formula(V), as follows:

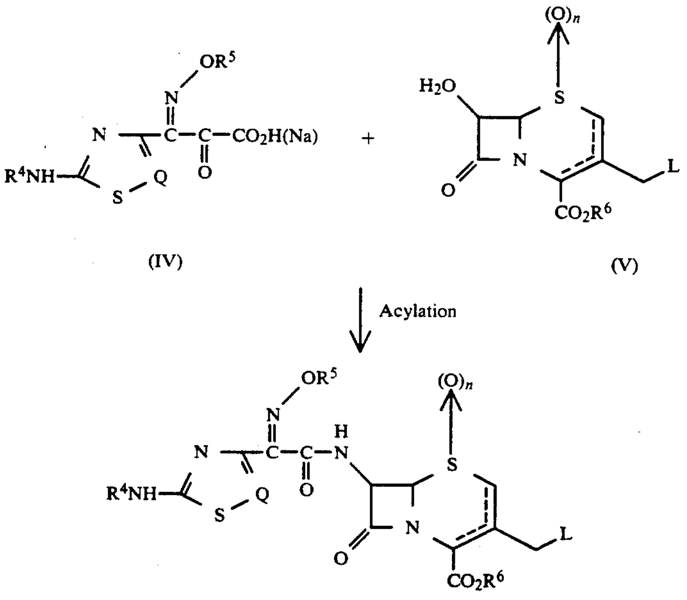

(IV) (V)

(II)

wherein
n, $R^4$, $R^5$, $R^6$, Q and L are the same as defined above; and the dotted line of the formula(V) presents a single bond or a double bond, so that the compounds of the formula(V) may be or compounds of the formula(V-a), the compounds of the formula(V-b), or mixtures thereof

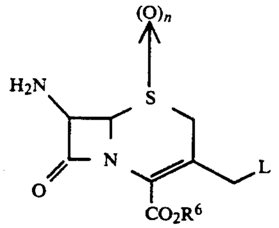

(V-a)

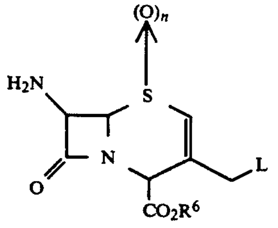

(V-b)

wherein n, $R^6$ and L and the same as defined above.

In the preparation of the objective compounds(I), the compounds of the formula(II) are used preferably in an amount of from 1 to 2 equivalent(s) based on 1 equivalent of the compounds of the formula(III).

Amino or acid protecting groups can be readily removed by a conventional deprotection method which are well known in the field of cephalosporin antibiotics. For example, acid- or base-hydrolysis or reduction are generally applicable. For further examples, when the protecting group is an amido group, it is feasible to subject such compounds to imino-halogenation and imino-etherification, and then, follow by hydrolysis. Acid hydrolysis is preferably applicable to removal of such groups as tri(di)phenylmethyl or alkoxycarbonyl, and is carried out in the presence of an organic acid such as formic acid, trifluoroacetic acid, or p-tolueneacetic acid or an inorganic acid such as hydrochloric acid or the like.

The reaction for introducing the compounds(III) into the 3-position of the compounds(II) to prepare compounds(I) is carried out in the presence of a solvent such as water, or a mixed aqueous solvent of water and a water-mixable solvent. In the reaction, the pH of the solvent showed ranges from 5 to 8, but preferably 6 to 7.5. An appropriate water-mixable solvent is acetonitrile or acetone.

Also, the reaction may be carried out at 40° to 100° C., preferably 60° to 80° C.

To stabilize reaction products and their intermediates, one or more salts selected from the group consisting of sodium iodide, potassium iodide, sodium bromide, potassium bromide and potassium thiocyanate can be used as stabilizing agents.

On the other hand, the separation and purification of the compounds(I) can be carried out using a known method such as recrystallization, column chromatography over silica gel or ion-exchange chromatography.

The cephalosporin compounds(I) of the present invention, and their non-toxic salts, preferably alkali metal salts, alkaline earth metal salts, inorganic acid salts or amino acid salts, show potent antibacterial activities against a variety of general pathogenic bacteria including Gram-negative and Gram-positive bacteria, therefore, they are especially useful in theraphy for treatment of bacterial infections in human beings and animals.

In order to illustrate the usefulness of the invented compounds, the minimal inhibitory concentrations(-MIC) thereof against standard strains and against clinically isolated-strains, were determined and compared with Ceftazidime of a known compound.

Also, the in vitro antibacterial activity was determined by the by a two-fold dilution method as described below:

That is, the two-fold serial dilutions of the compound were made dispersed in Müller-Hinton agar medium. 2 μl of standard test strain which had the $10^7$ CFU per ml was inoculated on the medium, and was incubated at 37° C. for 20 hours. The results of the MIC tests are shown in Table 1.

The results of the MIC tests against clinically separated-strains are shown in Table 2.

Specific examples of the compounds of formula(I) provided by this invention are shown below:

I-1: 7-[(Z)-2-(2-aminothiazol-4-yl)-2-(2-carboxylprop-2-oxyimino)acetamido]-3-(4,6-diamino-1-methylpyrimidinium-2-yl)thiomethyl-3-cephem-4-carboxylate

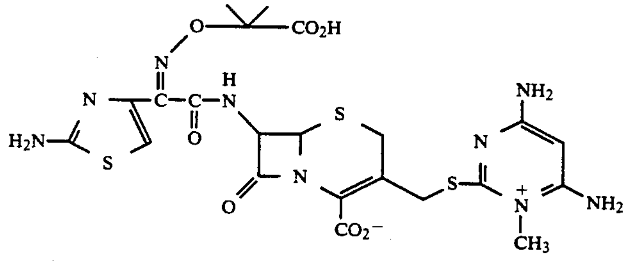

I-2: 7-[(Z)-2-(2-aminothiazol-4-yl)-2-(2-carboxylprop-2-oxyimino)acetamino]-3-(4,6-diamino-1-ethylpyrimidinium-2-yl)thiomethyl-3-cephem-4-carboxylate

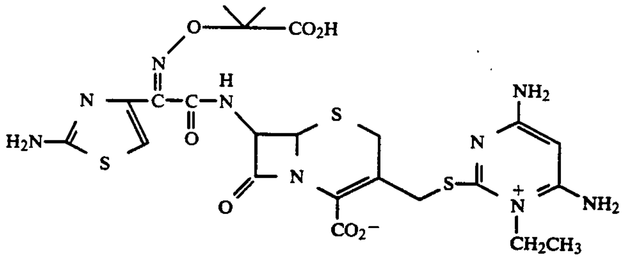

I-3: 3-(1-allyl-4,6-diaminopyrimidinium-2-yl)thiomethyl-7-[(Z)-2-(2-aminothiazol-4-yl)-2-(2-carboxyprop-2-oxyimino)acetamido]-3-cephem-4-carboxylate

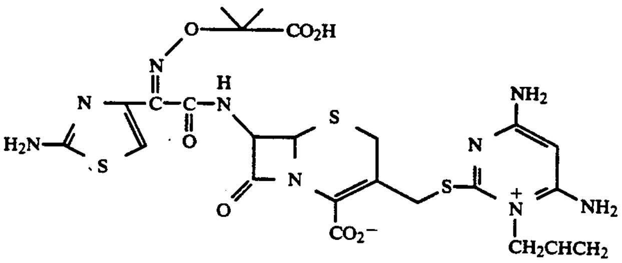

I-4: 7-[(Z)-2-(2-aminothiazol-4-yl)-2-(1-carboxyeth-1-oxyimino)acetamido]-3-(4,6-diamino-1-methylpyrimidinium-2-yl)thiomethyl-3-cephem-4-carboxylate -continued

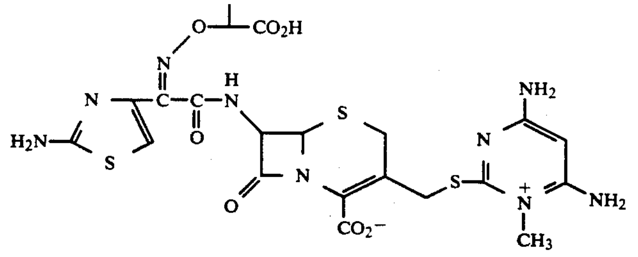

I-5: 7-[(Z)-2-(2-aminothiazol-4-yl)-2-(1-carboxyeth-1-oxyimino)acetamido]-3-(4,6-diamino-1-ethylpyrimidinium-2-yl)thiomethyl-3-cephem-4-carboxylate

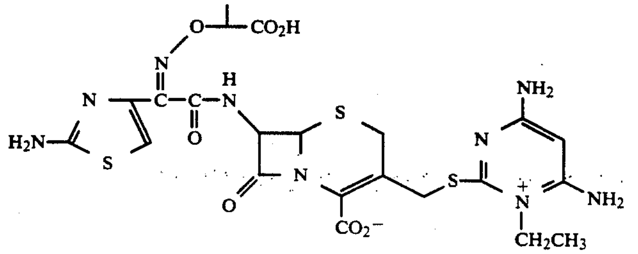

I-6: 3-(1-allyl-4,6-diaminopyrimidinium-2-yl)thiomethyl-7-[(Z)-2-(2-aminothiazol-4-yl)-2-(1-carboxyeth-1-oxyimino)acetamido]-3-cephem-4-carboxylate

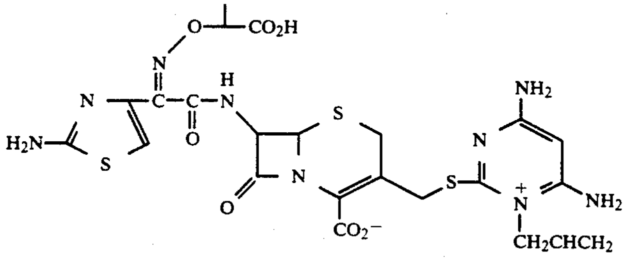

I-7: 7-[(Z)-2-(2-aminothiazol-4-yl)-2-(carboxymethoxyimino)acetamido]-3-(4,6-diamino-1-methylpyrimidinium-2-yl)thiomethyl-3-cephem-4-carboxylate

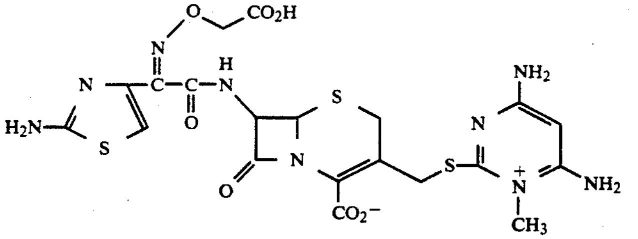

I-8: 7-[(Z)-2-(2-aminothiazol-4-yl)-2-(carboxymethoxyimino)acetamido]-3-(4,6-diamino-1-ethylpyrimidinium-2-yl)thiomethyl-3-cephem-4-carboxylate

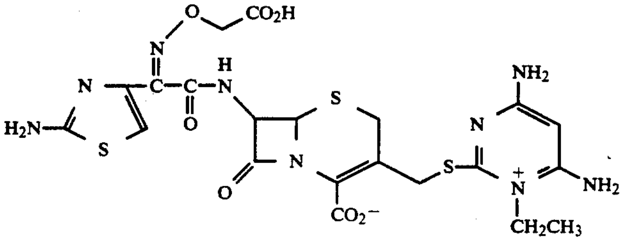

I-9: 3-(1-allyl-4,6-diaminopyrimidinium-2-yl)thiomethyl-7-[(Z)-2-(2-aminothiazol-4-yl)-2-(carboxymethoxyimino)acetamido]-3-cephem-4-carboxylate -continued

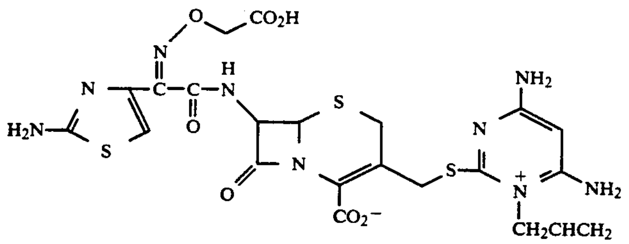

I-10: 7-[(Z)-2-(2-aminothiazol-4-yl)-2-(methoxyimino)acetamido]-3-(4,6-diamino-1-methylpyrimidinium-2-yl)thiomethyl-3-cephem-4-carboxylate

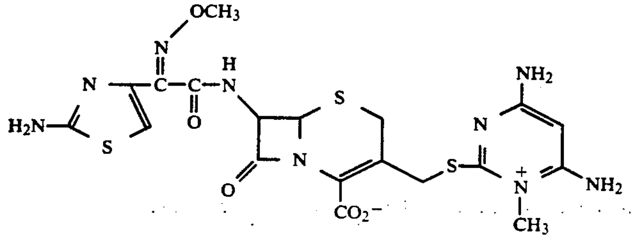

I-11: 7-[(Z)-2-(2-aminothiazol-4-yl)-2-(ethoxyimino)acetamido]-3-(4,6-diamino-1-methylpyrimidinium-2-yl)thiomethyl-3-cephem-4-carboxylate

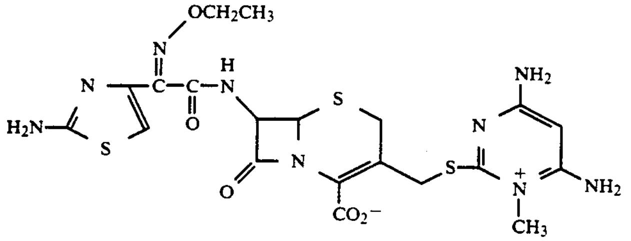

I-12: 7-[(Z)-2-(2-aminothiazol-4-yl)-2-(ethoxyimino)acetamido]-3-(4,6-diamino-1-ethylpyrimidinium-2-yl)thiomethyl-3-cephem-4-carboxylate

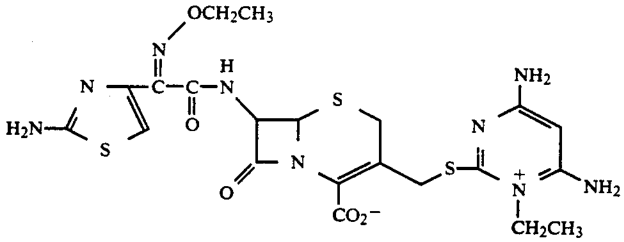

I-13: 7-[(Z)-2-(5-amino-1,2,4-thiadiazol-3-yl)-2-(2-carboxyprop-2-oxyimino)acetamido]-3-(1,4,6-triaminopyrimidinium-2-yl)thiomethyl-3-cephem-4-carboxylate

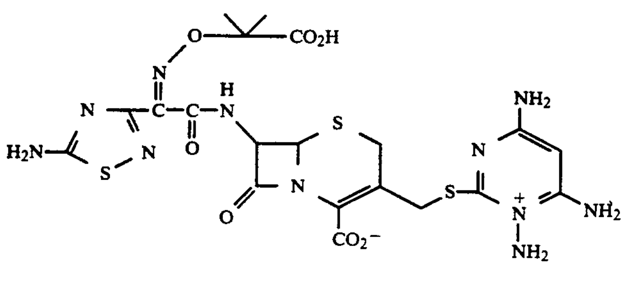

I-14: 7-[(Z)-2-(2-aminothiazol-4-yl)-2-(1-carboxyeth-1-oxyimino)acetamido]-3-(1,4,6-triaminopyrimidinium-2-yl)thiomethyl-3-cephem-4-carboxylate -continued

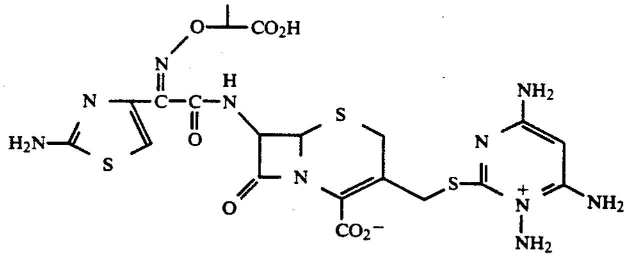

I-15: 7-[(Z)-2-(2-aminothiazol-4-yl)-2-(2-carboxyprop-2-oxyimino)acetamido]-3-(1,4,6-triaminopyrimidinium-2-yl)thiomethyl-3-cephem-4-carboxylate

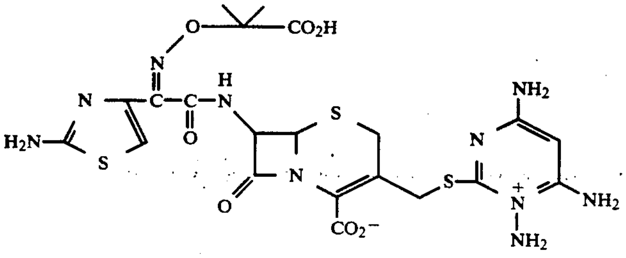

I-16: 7-[(Z)-2-(2-aminothiazol-4-yl)-2-(ethoxyimino)acetamido]-3-(1,4,6-triaminopyrimidinium-2-yl)thiomethyl-3-cephem-4-carboxylate

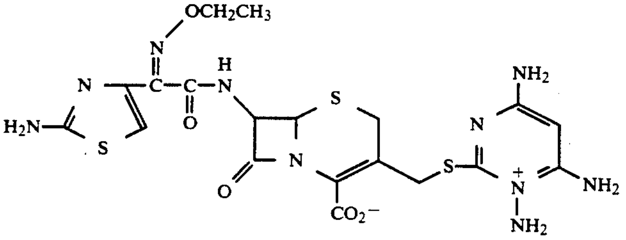

I-17: 7-[(Z)-2-(5-amino-1,2,4-thiadiazol-3-yl)-2-(ethoxyimino)acetamido]-3-(1,4,6-triaminopyrimidinium-2-yl)thiomethyl-3-cephem-4-carboxylate

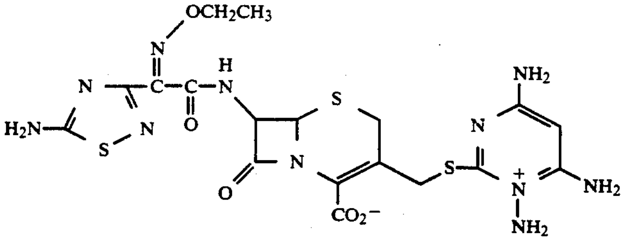

I-18: 7-[(Z)-2-(2-aminothiazol-4-yl)-2-(2-propyn-1-oxyimino)acetamido]-3-(1,4,6-triaminopyrimidinium-2-yl)thiomethyl-3-cephem-4-carboxylate

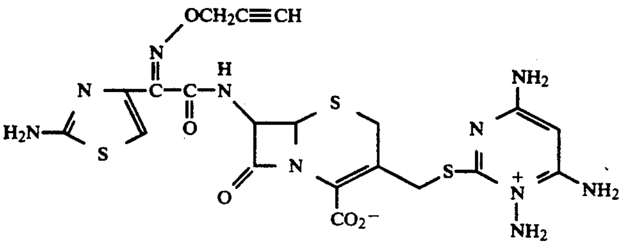

I-19: 7-[(Z)-2-(2-aminothiazol-4-yl)-2-(methoxyimino)acetamido]-3-(1,4,6-triaminopyrimidinium-2-yl)thiomethyl-3-cephem-4-carboxylate -continued

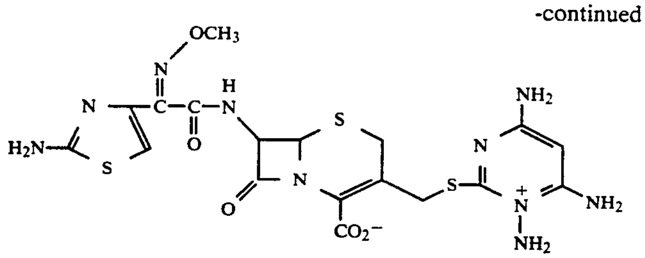

I-20: 7-[(Z)-2-(5-amino-1,2,4-thiadiazol-3-yl)-2-(ethoxyimino)acetamido]-3-(4,6-diamino-1-methylpyrimidinium-2-yl)thiomethyl-3-cephem-4-carboxylate

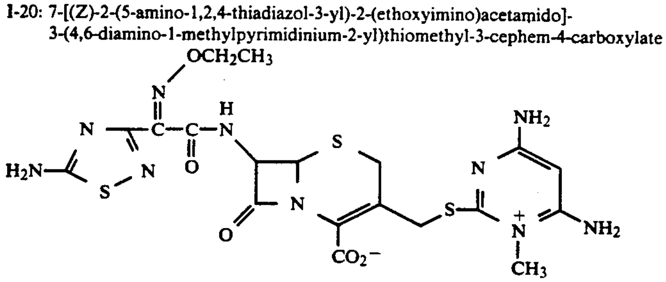

I-21: 7-[(Z)-2-(5-amino-1,2,4-thiadiazol-3-yl)-2-(ethoxyimino)acetamido]-3-(4,6-diamino-1-ethylpyrimidinium-2-yl)thiomethyl-3-cephem-4-carboxylate

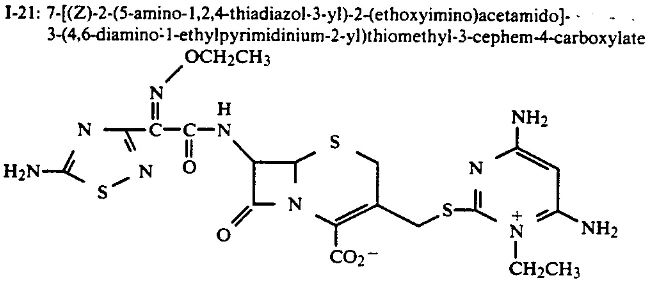

I-22: 7-[(Z)-2-(5-amino-1,2,4-thiadiazol-3-yl)-2-(ethoxyimino)acetamido]-3-(4,6-diamino-1-propylpyrimidinium-2-yl)thiomethyl-3-cephem-4-carboxylate

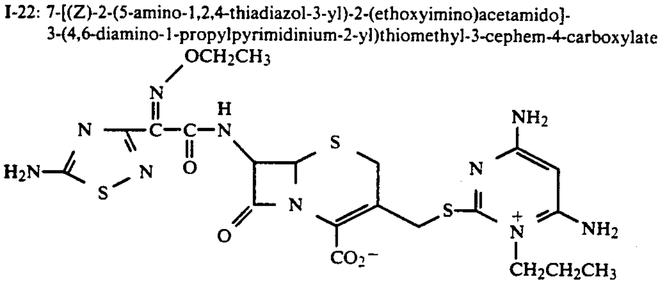

I-23: 3-(1-allyl-4,6-diaminopyrimidinium-2-yl)-7-[(Z)-2-(5-amino-1,2,4-thiadiazol-3-yl)-2-(ethoxyimino)acetamido]-3-cephem-4-carboxylate

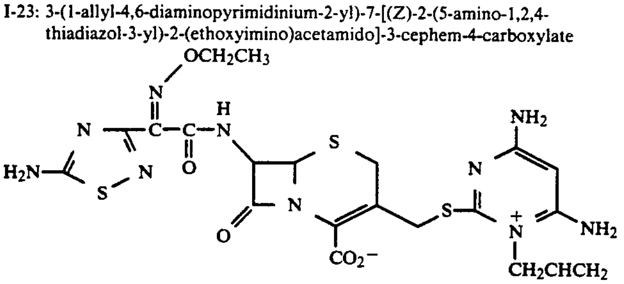

I-24: 7-[(Z)-2-(5-amino-1,2,4-thiadiazol-3-yl)-2-(methoxyimino)acetamido]-3-(4,6-diamino-1-methylpyrimidinium-2-yl)thiomethyl-3-cephem-4-carboxylate

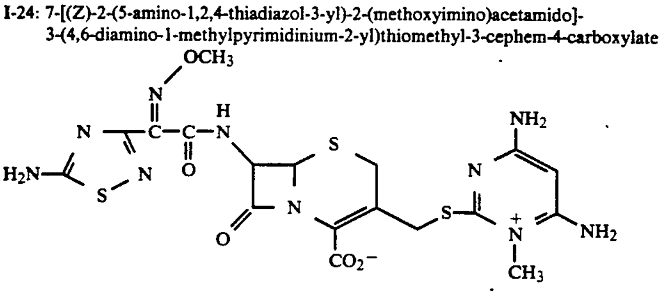

-continued

I-25: 7-[(Z)-2-(5-amino-1,2,4-thiadiazol-3-yl)-2-(methoxyimino)acetamido]-3-(4,6-diamino-1-ethylpyrimidinium-2-yl)thiomethyl-3-cephem-4-carboxylate

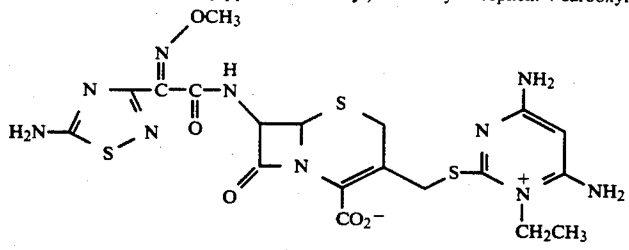

I-26: 7-[(Z)-2-(5-amino-1,2,4-thiadiazol-3-yl)-2-(2-carboxyprop-2-oxymino)acetamido]-3-(4,6-diamino-1-methylpyrimidinium-2-yl)thiomethyl-3-cephem-4-carboxylate

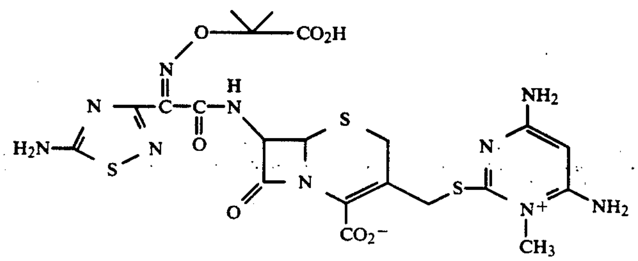

I-27: 7-[(Z)-2-(5-amino-1,2,4-thiadiazol-3-yl)-2-(2-carboxyprop-2-oxyimino)acetamido]-3-(4,6-diamino-1-ethylpyrimidinium-2-yl)thiomethyl-3-cephem-4-carboxylate

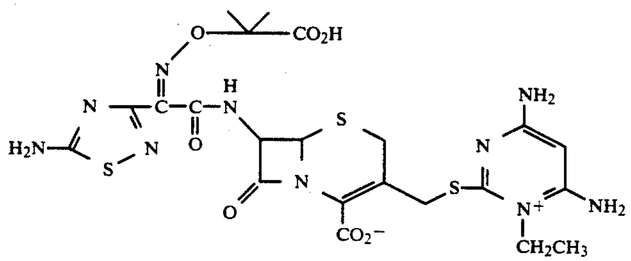

I-28: 7-[(Z)-2-(5-amino-1,2,4-thiadiazol-3-yl)-2-(2-carboxyprop-2-oxyimino)acetamido]-3-(4,6-diamino-1-propylpyrimidinium-2-yl)thiomethyl-3-cephem-4-carboxylate

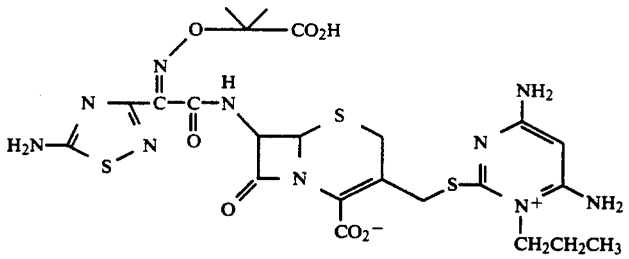

I-29: 7-[(Z)-2-(5-amino-1,2,4-thiadiazol-3-yl)-2-(2-carboxyprop-2-oxyimino)acetamido]-3-(1-butyl-4,6-diaminopyrimidinium-2-yl)thiomethyl-3-cephem-4-carboxylate

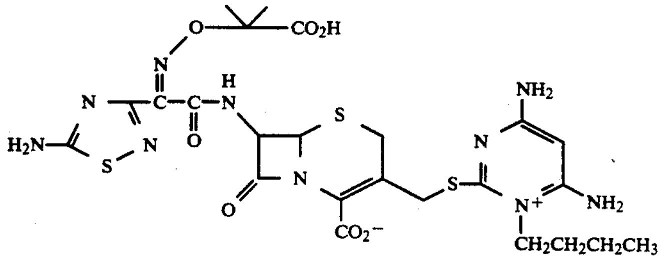

I-30: 7-[(Z)-2-(2-aminothiazol-4-yl)-2-(2-carboxyprop-2-oxyimino)acetamido]-3-(4,6-diamino-1,5-dimethylpyrimidinium-2-yl)thiomethyl-3-cephem-4-carboxylate -continued

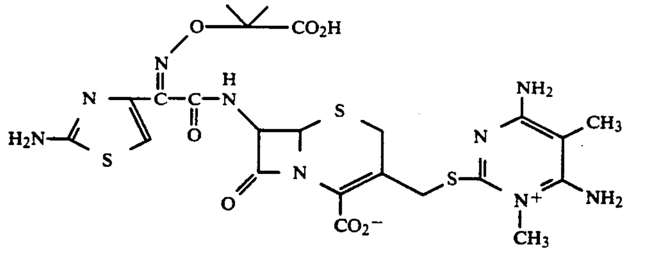

I-31: 7-[(Z)-2-(2-aminothiazol-4-yl)-2-(2-carboxyprop-2-oxyimino)acetamido]-3-(4,6-diamino-5-ethyl-1-methylpyrimidinium-2-yl)thiomethyl-3-cephem-4-carboxylate

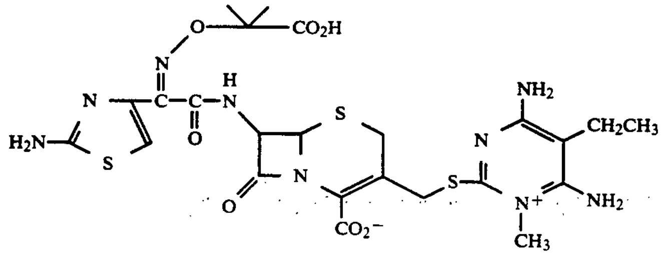

I-32: 7-[(Z)-2-(2-aminothiazol-4-yl)-2-(2-carboxyprop-2-oxyimino)acetamido]-3-(4,6-diamino-1-ethyl-5-methylpyrimidinium-2-yl)thiomethyl-3-cephem-4-carboxylate

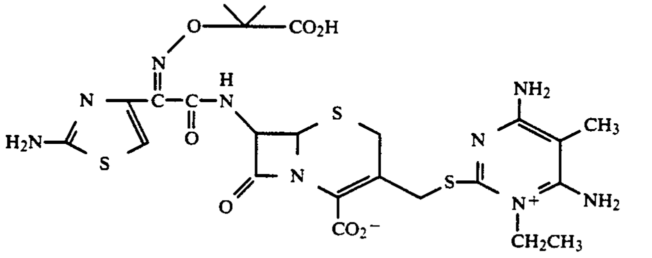

I-33: 7-[(Z)-2-(2-aminothiazol-4-yl)-2-(2-carboxyprop-2-oxyimino)acetamido]-3-(4,6-diamino-1,5-diethylpyrimidinium-2-yl)thiomethyl-3-cephem-4-carboxylate

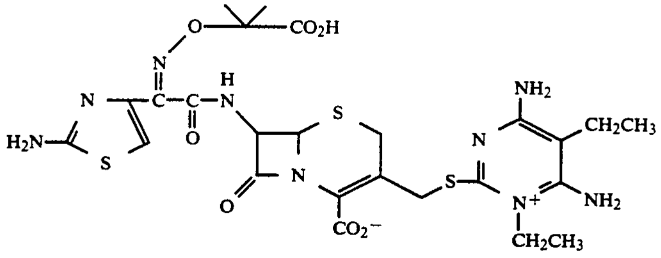

I-34: 7-[(Z)-2-(2-aminothiazol-4-yl)-2-(2-carboxyprop-2-oxyimino)acetamido]-3-(5-methyl-1,4,6-triaminopyrimidinium-2-yl)thiomethyl-3-cephem-4-carboxylate

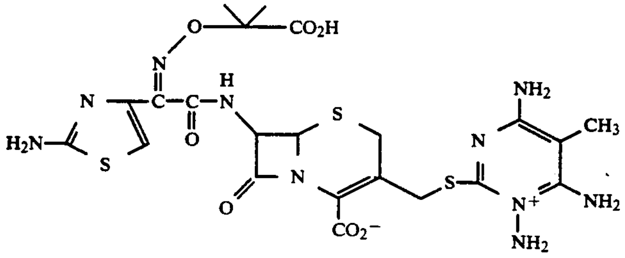

I-35: 7-[(Z)-2-(2-aminothiazol-4-yl)-2-(2-carboxyprop-2-oxyimino)acetamido]-3-(4,6-diamino-1-phenylpyrimidinium-2-yl)thiomethyl-3-cephem-4-carboxylate -continued

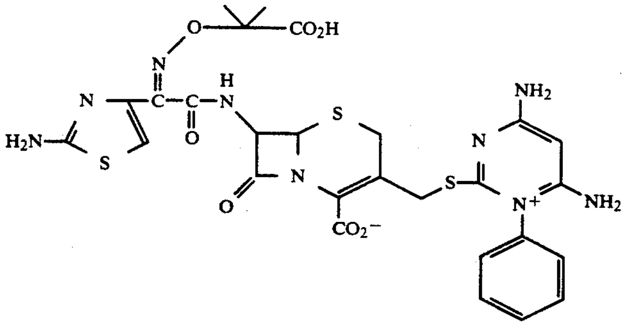

I-36: 7-[(Z)-2-(2-aminothiazol-4-yl)-2-(2-carboxyprop-2-oxyimino)acetamido]-3-[1-(4-hydroxyphenyl)-4,6-diaminopyrimidinium-2-yl]-thiomethyl-3-cephem-4-carboxylate

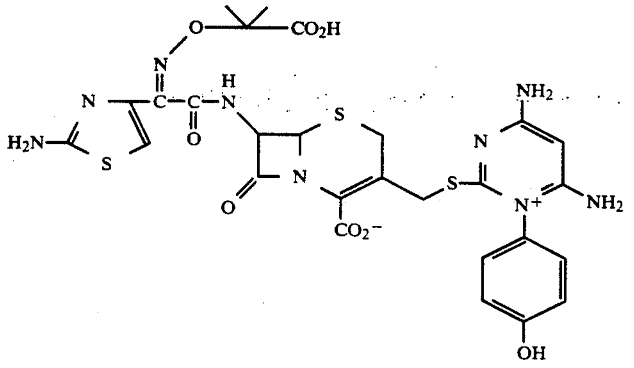

I-37: 7-[(Z)-2-(2-aminothiazol-4-yl)-2-(carboxymethoxyimino)acetamido]-3-(4,6-diamino-1-phenylpyrimidinium-2-yl)thiomethyl-3-cephem-4-carboxylate

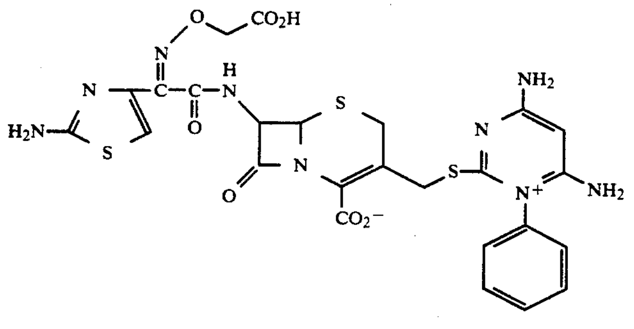

I-38: 7-[(Z)-2-(2-aminothiazol-4-yl)-2-(1-carboxyeth-1-oxyimino)acetamido]-3-(4,6-diamino-1-phenylpyrimidinium-2-yl)thiomethyl-3-cephem-4-carboxylate

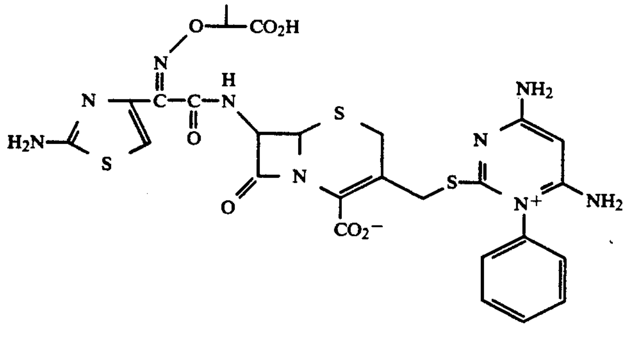

I-39: 7-[(Z)-2-(2-aminothiazol-4-yl)-2-(ethoxyimino)acetamido]-3-(4,6-diamino-1-phenylpyrimidinium-2-yl)thiomethyl-3-cephem-4-carboxylate -continued

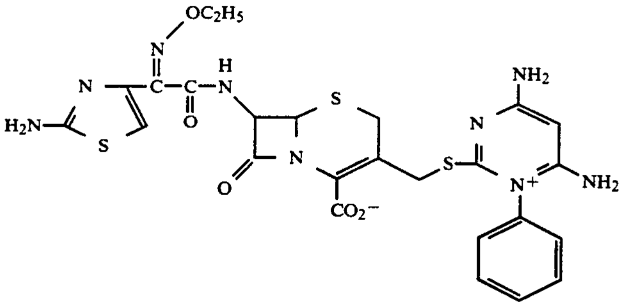

I-40: 7-[(Z)-2-(2-aminothiazol-4-yl)-2-(ethoxyimino)acetamido]-3-[1-(4-chlorophenyl)-4,6-diaminopyrimidinium-2-yl]thiomethyl-3-cephem-4-carboxylate

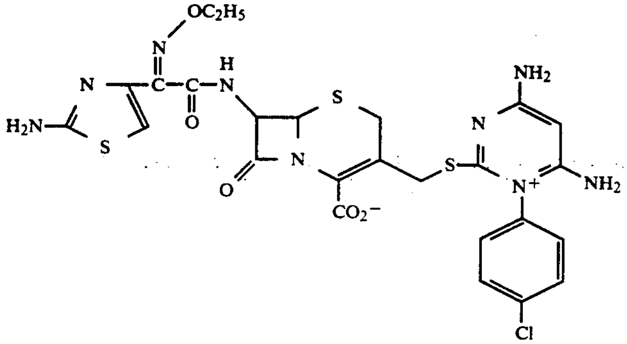

I-41: 7-[(Z)-2-(2-aminothiazol-4-yl)-2-(2-carboxyprop-2-oxyimino)acetamido]-3-[4,6-diamino-1-(2,4-dimethylphenyl)-pyrimidinium-2-yl]thiomethyl-3-cephem-4-carboxylate

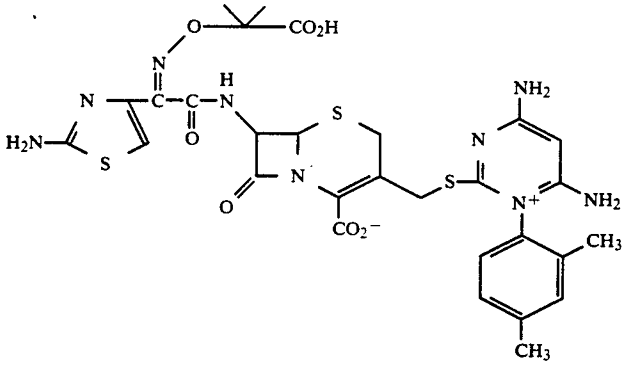

I-42: 7-[(Z)-2-(2-aminothiazol-4-yl)-2-(ethoxyimino)acetamido]-3-(4,6-diamino-1-(2,4-dimethylphenyl)-pyrimidinium-2-yl]-thiomethyl-3-cephem-4-carboxylate

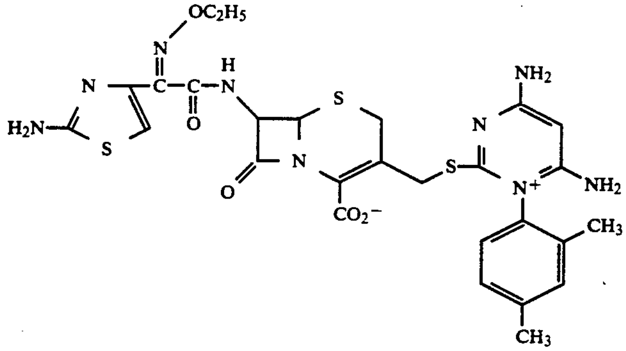

I-43: 7-[(Z)-2-(2-aminothiazol-4-yl)-2-(2-carboxyprop-2-oxyimino)acetamido]-3-[4,6-diamino-1-(2,6-dimethoxyphenyl)-pyrimidinium-2-yl]thiomethyl-3-cephem-4-carboxylate -continued

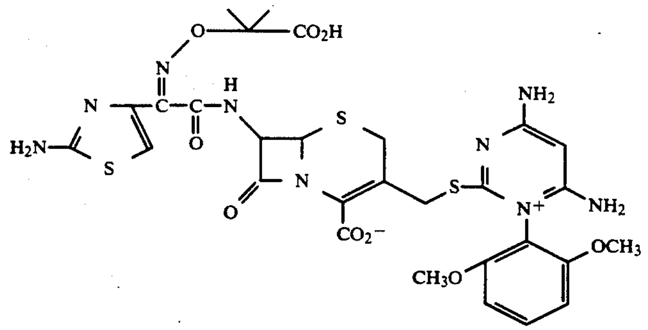

I-44: 7-[(Z)-2-(2-aminothiazol-4-yl)-2-(2-carboxyprop-2-oxyimino)acetamido]-3-[4,6-diamino-1-(4-chlorophenyl)-pyrimidinium-2-yl]thiomethyl-3-cephem-4-carboxylate

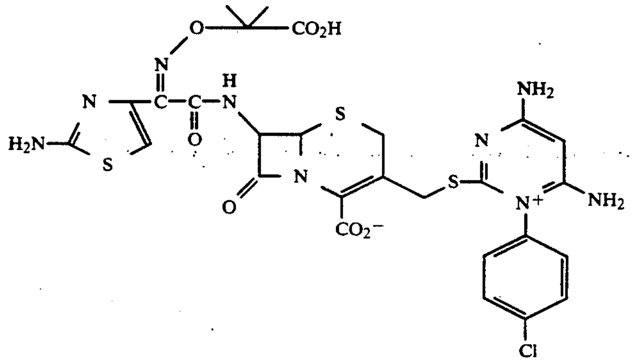

I-45: 7-[(Z)-2-(2-aminothiazol-4-yl)-2-(1-carboxyeth-1-oxyimino)acetamido]-3-[4,6-diamino-1-propylpyrimidinium-2-yl]thiomethyl-3-cephem-4-carboxylate

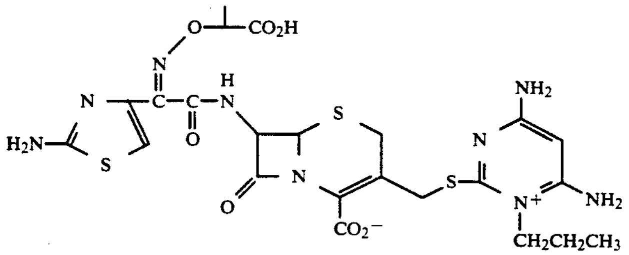

I-46: 7-[(Z)-2-(2-aminothiazol-4-yl)-2-(2-propyn-1-oxyimino)acetamido]-3-(4,6-diamino-1-methylpyrimidinium-2-yl)thiomethyl-3-cephem-4-carboxylate

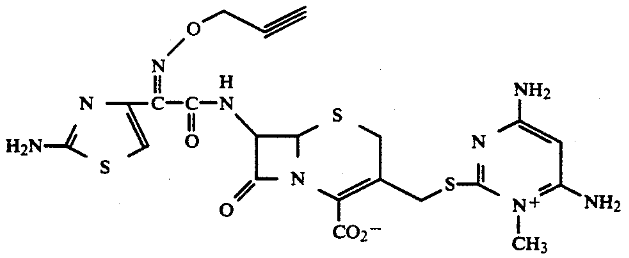

I-47: 7-[(Z)-2-(2-aminothiazol-4-yl)-2-(2-propyn-1-oxyimino)acetamido]-3-(4,6-diamino-1-ethylpyrimidinium-2-yl)thiomethyl-3-cephem-4-carboxylate

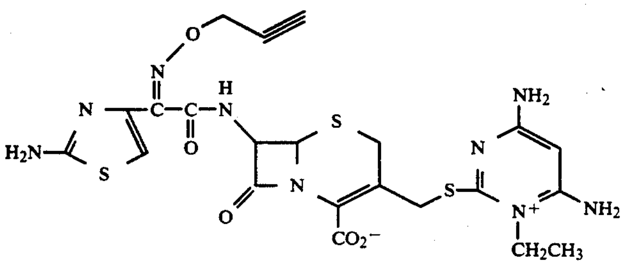

-continued

I-48: 7-[(Z)-2-(2-aminothiazol-4-yl)-2-(2-carboxyprop-2-oxyimino)acetamido]-3-(1-cyclopropyl-4,6-diaminopyrimidinium-2-yl)-3-cephem-4-carboxylate

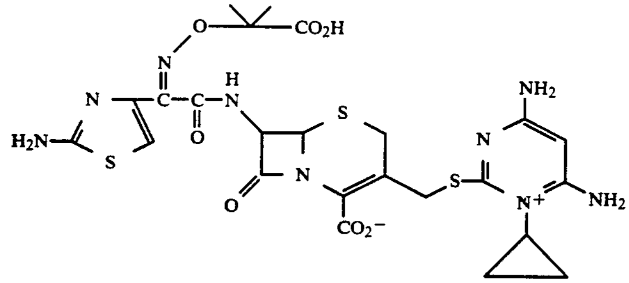

I-49: 7-[(Z)-2-(2-aminothiazol-4-yl)-2-(2-propen-1-oxyimino)acetamido]-3-(4,6-diamino-1-methylpyrimidinium-2-yl)-3-cephem-4-carboxylate

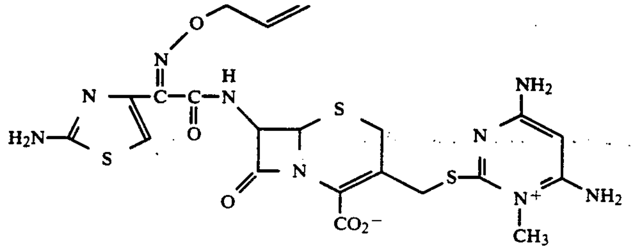

I-50: 7-[(Z)-2-(2-aminothiazol-4-yl)-2-(2-propen-1-oxyimino)acetamido]-3-(4,6-diamino-1-ethylpyrimidinium-2-yl)-3-cephem-4-carboxylate

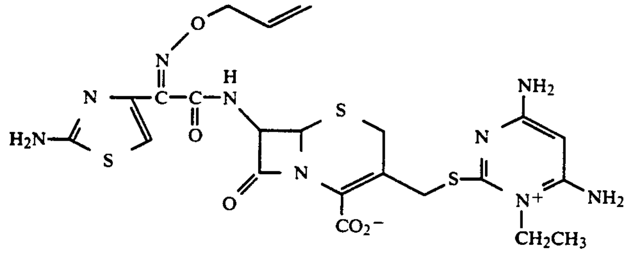

Comparative compound: Ceftazidime

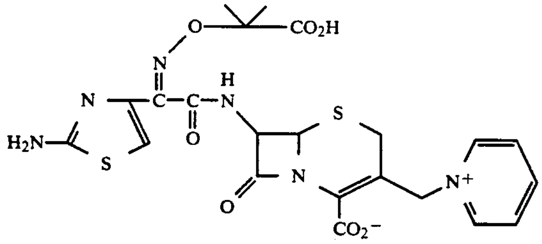

TABLE 1

Antibacterial Activity

| Strains | | MIC, μg/ml | | | | | | | |
|---|---|---|---|---|---|---|---|---|---|
| | | I-1 | I-2 | I-3 | I-4 | I-5 | I-6 | I-7 | I-8 |
| *Bacillus cereus* | ATCC 11778 | 64 | 64 | 64 | >128 | 128 | 128 | 128 | 64 |
| *Bacillus megaterium* | ATCC 9885 | 0.25 | 0.5 | 0.5 | 1 | 1 | 1 | 0.5 | 0.5 |
| *Micrococcus luteus* | ATCC 9341 | 0.25 | 0.25 | 0.25 | 0.5 | 0.25 | 0.25 | 0.5 | 0.13 |
| *Staphylococcus aureus* | ATCC 6538p | 2 | 2 | 4 | 4 | 2 | 4 | 2 | 4 |
| *Staphylococcus aureus* | ATCC 10537 | 1 | 2 | 2 | 2 | 2 | 2 | 2 | 2 |
| *Staphylococcus epidermidis* | ATCC 12228 | 1 | 1 | 2 | 2 | 1 | 2 | 1 | 1 |
| *Streptococcus faecalis* | ATCC 29212 | | | >128 | | | >128 | >128 | >128 |
| *Acinetobacter calcoaceticus* | ATCC 15473 | 2 | 4 | 4 | 4 | 4 | 4 | 4 | 8 |
| *Citrobacter freundii* | ATCC 8090 | 0.063 | 0.13 | 0.13 | 0.063 | 0.063 | 0.063 | 0.031 | 0.031 |
| *Enterobacter aerogenes* | ATCC 29751 | 1 | 2 | 2 | 1 | 0.5 | 1 | 0.5 | 1 |
| *Enterobacter cloacae* | ATCC 27508 | 0.016 | 0.031 | 0.031 | 0.016 | 0.016 | 0.016 | <=0.008 | <=0.008 |
| *Escherichia coli* | ATCC 10536 | 0.063 | 0.063 | 0.13 | 0.063 | 0.063 | 0.063 | 0.016 | 0.031 |
| *Escherichia coli* | ATCC 25922 | 0.063 | 0.063 | 0.13 | 0.031 | 0.063 | | 0.016 | 0.031 |
| *Klebsiella pneumoniae* | ATCC 10031 | 0.063 | 0.063 | 0.063 | 0.031 | 0.031 | | 0.016 | 0.016 |

TABLE 1-continued

| Antibacterial Activity | | | | | | | | | |
|---|---|---|---|---|---|---|---|---|---|
| *Morganella morganii* | ATCC 8076h | <=0.008 | <=0.008 | <=0.008 | <=0.008 | <=0.008 | <=0.008 | <=0.008 | <=0.008 |
| *Proteus mirabilis* | ATCC 25933 | 0.031 | 0.031 | 0.031 | 0.031 | 0.031 | 0.031 | 0.016 | 0.031 |
| *Proteus vulgaris* | ATCC 6059 | 0.031 | 0.031 | 0.031 | 0.031 | 0.031 | 0.031 | 0.016 | 0.016 |
| *Providencia rettgeri* | ATCC 9250 | <=0.008 | <=0.008 | <=0.008 | <=0.008 | <=0.008 | <=0.008 | <=0.008 | 0.016 |
| *Pseudomonas aeruginosa* | ATCC 25619 | 1 | 1 | 1 | 2 | 1 | 2 | 2 | 2 |
| *Pseudomonas aeruginosa* | ATCC 27853 | 1 | 1 | 2 | 1 | 1 | 2 | 2 | 2 |
| *Pseudomonas aeruginosa* | ATCC 10145 | 2 | 2 | 2 | 2 | 2 | 4 | 4 | 4 |
| *Salmonella typhimurium* | ATCC 14028 | 0.13 | 0.25 | 0.25 | 0.13 | 0.13 | 0.25 | 0.063 | 0.063 |
| *Serratia marcescens* | ATCC 27117 | 0.063 | 0.13 | 0.13 | 0.063 | 0.063 | 0.13 | 0.016 | 0.031 |
| *Shigella flexneri* | ATCC 11836 | 0.031 | 0.031 | 0.031 | 0.031 | 0.031 | 0.031 | <=0.008 | 0.016 |
| *Shigella sonnei* | ATCC 11060 | 0.031 | 0.063 | 0.063 | 0.031 | 0.031 | 0.063 | 0.016 | 0.031 |

| Strains | | MIC, μg/ml | | | | | | | |
|---|---|---|---|---|---|---|---|---|---|
| | | I-9 | I-10 | I-11 | I-12 | I-13 | I-14 | I-15 | I-16 |
| *Bacillus cereus* | ATCC 11778 | 64 | 32 | 32 | 16 | >128 | 64 | 64 | 4 |
| *Bacillus megaterium* | ATCC 9885 | 0.25 | 0.25 | 0.13 | 0.063 | 1 | 0.5 | 0.5 | 0.063 |
| *Micrococcus luteus* | ATCC 9341 | 0.25 | 0.063 | 0.016 | <=0.008 | 1 | 0.5 | 0.25 | 0.016 |
| *Staphylococcus aureus* | ATCC 6538p | 4 | 0.25 | 0.25 | 0.25 | 16 | 4 | 4 | 0.25 |
| *Staphylococcus aureus* | ATCC 10537 | 2 | 0.25 | 0.25 | 0.25 | 8 | 2 | 2 | 0.25 |
| *Staphylococcus epidermidis* | ATCC 12228 | 1 | 0.13 | 0.063 | 0.063 | 4 | 1 | 2 | 0.063 |
| *Streptococcus faecalis* | ATCC 29212 | >128 | | | 32 | >128 | >128 | >128 | 32 |
| *Acinetobacter calcoaceticus* | ATCC 15473 | 8 | 8 | 4 | 4 | 4 | 2 | 2 | 4 |
| *Citrobacter freundii* | ATCC 8090 | 0.063 | 0.063 | 0.063 | 0.063 | 0.13 | 0.031 | 0.063 | 0.063 |
| *Enterobacter aerogenes* | ATCC 29751 | 1 | 0.5 | 0.5 | 0.5 | 1 | 0.5 | 1 | 0.25 |
| *Enterobacter cloacae* | ATCC 27508 | <=0.008 | <=0.008 | <=0.008 | <=0.008 | 0.031 | <=0.008 | 0.016 | 0.016 |
| *Escherichia coli* | ATCC 10536 | 0.031 | 0.063 | 0.13 | 0.063 | 0.13 | 0.031 | 0.063 | 0.063 |
| *Escherichia coli* | ATCC 25922 | 0.031 | 0.063 | 0.13 | 0.13 | 0.13 | 0.031 | 0.063 | 0.063 |
| *Klebsiella pneumoniae* | ATCC 10031 | 0.031 | 0.016 | 0.016 | <=0.008 | 0.063 | 0.031 | 0.063 | <=0.008 |
| *Morganella morganii* | ATCC 8076h | <=0.008 | <=0.008 | <=0.008 | <=0.008 | 0.016 | <=0.008 | <=0.008 | <=0.008 |
| *Proteus mirabilis* | ATCC 25933 | 0.031 | 0.13 | 0.25 | 0.13 | 0.13 | 0.031 | 0.016 | 0.13 |
| *Proteus vulgaris* | ATCC 6059 | 0.031 | 0.13 | 0.25 | 0.25 | 0.13 | 0.031 | 0.016 | 0.13 |
| *Providencia rettgeri* | ATCC 9250 | <=0.008 | <=0.008 | <=0.008 | <=0.008 | <=0.008 | <=0.008 | <=0.008 | <=0.008 |
| *Pseudomonas aeruginosa* | ATCC 25619 | 2 | 2 | 2 | 1 | 2 | 1 | 1 | 0.5 |
| *Pseudomonas aeruginosa* | ATCC 27853 | 4 | 8 | 4 | 2 | 1 | 1 | 1 | 2 |
| *Pseudomonas aeruginosa* | ATCC 10145 | 16 | 32 | 8 | 8 | 2 | 2 | 1 | 4 |
| *Salmonella typhimurium* | ATCC 14028 | 0.13 | 0.25 | 0.25 | 0.5 | 0.5 | 0.13 | 0.13 | 0.25 |
| *Serratia marcescens* | ATCC 27117 | 0.063 | 0.063 | 0.13 | 0.13 | 0.25 | 0.031 | 0.063 | 0.13 |
| *Shigella flexneri* | ATCC 11836 | 0.031 | 0.016 | 0.031 | 0.031 | 0.063 | 0.031 | 0.031 | 0.016 |
| *Shigella sonnei* | ATCC 11060 | 0.063 | 0.063 | 0.13 | 0.13 | 0.013 | 0.016 | 0.063 | 0.063 |

| Strains | | MIC, μg/ml | | | | | | | |
|---|---|---|---|---|---|---|---|---|---|
| | | I-17 | I-18 | I-19 | I-20 | I-21 | I-22 | I-23 | I-24 |
| *Bacillus cereus* | ATCC 11778 | 8 | 8 | 8 | 32 | 16 | 16 | 16 | 32 |
| *Bacillus megaterium* | ATCC 9885 | 0.13 | 0.063 | 0.13 | 0.13 | 0.13 | 0.13 | 0.25 | 0.25 |
| *Micrococcus luteus* | ATCC 9341 | 0.016 | 0.013 | 0.016 | 0.031 | 0.016 | 0.016 | 0.016 | 0.13 |
| *Staphylococcus aureus* | ATCC 6538p | 0.5 | 0.25 | 0.25 | 0.5 | 0.5 | 0.5 | 1 | 0.5 |
| *Staphylococcus aureus* | ATCC 10537 | 0.5 | 0.25 | 0.5 | 0.25 | 0.25 | 0.5 | 1 | 0.5 |
| *Staphylococcus epidermidis* | ATCC 12228 | 0.25 | 0.063 | 0.063 | 0.25 | 0.13 | 0.25 | 0.25 | 0.25 |
| *Streptococcus faecalis* | ATCC 29212 | 32 | 32 | 32 | 32 | 16 | 16 | 32 | 32 |
| *Acinetobacter calcoaceticus* | ATCC 15473 | 2 | 2 | 4 | 2 | 4 | 4 | 8 | 2 |
| *Citrobacter freundii* | ATCC 8090 | 0.063 | 0.063 | 0.13 | 0.13 | 0.13 | 0.25 | 0.25 | 0.13 |
| *Enterobacter aerogenes* | ATCC 29751 | 0.25 | 0.25 | 0.25 | 0.25 | 0.5 | 1 | 2 | 1 |
| *Enterobacter cloacae* | ATCC 27508 | 0.016 | <=0.008 | 0.016 | 0.016 | 0.016 | 0.031 | 0.031 | 0.063 |
| *Escherichia coli* | ATCC 10536 | 0.13 | 0.13 | 0.13 | 0.13 | 0.13 | 0.25 | 0.5 | 0.13 |
| *Escherichia coli* | ATCC 25922 | 0.13 | 0.063 | 0.13 | 0.13 | 0.13 | 0.25 | 0.25 | 0.13 |
| *Klebsiella pneumoniae* | ATCC 10031 | 0.016 | <=0.008 | <=0.008 | 0.016 | 0.016 | 0.016 | 0.031 | 0.031 |
| *Morganella morganii* | ATCC 8076h | 0.016 | <=0.008 | 0.008 | 0.016 | 0.016 | 0.031 | 0.031 | 0.063 |
| *Proteus mirabilis* | ATCC 25933 | 0.5 | 0.13 | 0.13 | 0.5 | 1 | 2 | 2 | 1 |
| *Proteus vulgaris* | ATCC 6059 | 0.5 | 0.13 | 0.016 | 1 | 1 | 2 | 1 | 1 |
| *Providencia rettgeri* | ATCC 9250 | <=0.008 | <=0.008 | <=0.008 | <=0.008 | <=0.008 | <=0.008 | <=0.008 | 0.016 |
| *Pseudomonas aeruginosa* | ATCC 25619 | 0.5 | 0.5 | 0.5 | 1 | 1 | 1 | 2 | 4 |
| *Pseudomonas aeruginosa* | ATCC 27853 | 2 | 2 | 1 | 2 | 2 | 4 | 8 | 4 |
| *Pseudomonas aeruginosa* | ATCC 10145 | 4 | 4 | 2 | 4 | 4 | 16 | 16 | 16 |
| *Salmonella typhimurium* | ATCC 14028 | 0.5 | 0.25 | 0.25 | 0.5 | 0.5 | 2 | 2 | 0.5 |
| *Serratia marcescens* | ATCC 27117 | 0.25 | 0.13 | 0.25 | 0.25 | 0.25 | 0.5 | 1 | 0.25 |
| *Shigella flexneri* | ATCC 11836 | 0.031 | 0.016 | 0.016 | 0.031 | 0.063 | 0.13 | 0.13 | 0.031 |
| *Shigella sonnei* | ATCC 11060 | 0.13 | 0.13 | 0.063 | 0.13 | 0.25 | 0.5 | 0.5 | 0.13 |

| Strains | | MIC, μg/ml | | | | | | | |
|---|---|---|---|---|---|---|---|---|---|
| | | I-25 | I-26 | I-27 | I-28 | I-29 | I-30 | I-31 | I-32 |
| *Bacillus cereus* | ATCC 11778 | 32 | >128 | >128 | 128 | 128 | 128 | 128 | 64 |
| *Bacillus megaterium* | ATCC 9885 | 0.13 | 1 | 1 | 0.25 | 0.25 | 0.5 | | |
| *Micrococcus luteus* | ATCC 9341 | 0.031 | 1 | 0.5 | 0.5 | 0.5 | 0.5 | 0.5 | 0.25 |
| *Staphylococcus aureus* | ATCC 6538p | 0.5 | 8 | 8 | 8 | 8 | 4 | 4 | 4 |
| *Staphylococcus aureus* | ATCC 10537 | 0.5 | 8 | 4 | 4 | 4 | 2 | 4 | 2 |
| *Staphylococcus epidermidis* | ATCC 12228 | 0.13 | 4 | 4 | 4 | 8 | 2 | 2 | 1 |
| *Streptococcus faecalis* | ATCC 29212 | 32 | >128 | >128 | >128 | >128 | | >128 | >128 |
| *Acinetobacter calcoaceticus* | ATCC 15473 | 2 | 4 | 8 | 8 | 32 | 4 | 8 | 8 |
| *Citrobacter freundii* | ATCC 8090 | 0.13 | 0.13 | 0.25 | 0.13 | 0.25 | 0.13 | 0.13 | 0.13 |
| *Enterobacter aerogenes* | ATCC 29751 | 1 | 1 | 2 | 4 | 1 | 2 | 2 | 2 |

TABLE 1-continued

Antibacterial Activity

| | | | | | | | | | |
|---|---|---|---|---|---|---|---|---|---|
| *Enterobacter cloacae* | ATCC 27508 | 0.031 | 0.031 | 0.063 | 0.031 | 0.063 | 0.063 | 0.016 | 0.016 |
| *Escherichia coli* | ATCC 10536 | 0.13 | 0.13 | 0.13 | 0.13 | 0.25 | 0.063 | 0.063 | 0.13 |
| *Escherichia coli* | ATCC 25922 | 0.13 | 0.13 | 0.13 | 0.13 | 0.25 | 0.063 | 0.13 | 0.13 |
| *Klebsiella pneumoniae* | ATCC 10031 | 0.031 | 0.13 | 0.063 | 0.13 | 0.13 | 0.063 | 0.063 | 0.063 |
| *Morganella morganii* | ATCC 8076h | 0.031 | <=0.008 | <=0.008 | <=0.008 | 0.016 | <=0.008 | <=0.008 | <=0.008 |
| *Proteus mirabilis* | ATCC 25933 | 1 | 0.13 | 0.13 | 0.13 | 1 | 0.031 | 0.031 | 0.031 |
| *Proteus vulgaris* | ATCC 6059 | 1 | 0.13 | 0.13 | 0.25 | 1 | 0.063 | 0.063 | 0.063 |
| *Providencia rettgeri* | ATCC 9250 | 0.016 | <=0.008 | <=0.008 | <=0.008 | <=0.008 | <=0.008 | <=0.008 | <=0.008 |
| *Pseudomonas aeruginosa* | ATCC 25619 | 4 | 2 | 2 | 2 | 4 | 2 | 1 | 2 |
| *Pseudomonas aeruginosa* | ATCC 27853 | 4 | 2 | 2 | 2 | 2 | 2 | 2 | 2 |
| *Pseudomonas aeruginosa* | ATCC 10145 | 16 | 2 | 4 | 4 | 8 | 2 | 4 | 4 |
| *Salmonella typhimurium* | ATCC 14028 | 0.25 | 0.5 | 0.5 | 0.5 | 0.5 | 0.25 | 0.25 | 0.25 |
| *Serratia marcescens* | ATCC 27117 | 0.25 | 0.25 | 0.25 | 0.25 | 0.5 | 0.13 | 0.25 | 0.13 |
| *Shigella flexneri* | ATCC 11836 | 0.031 | 0.063 | 0.25 | 0.063 | 0.13 | 0.031 | 0.063 | 0.031 |
| *Shigella sonnei* | ATCC 11060 | 0.13 | 0.13 | 0.13 | 0.13 | 0.5 | 0.063 | 0.063 | 0.13 |

| Strains | | MIC, μg/ml | | | | | | | |
|---|---|---|---|---|---|---|---|---|---|
| | | I-33 | I-34 | I-35 | I-36 | I-40 | I-43 | I-45 | I-46 |
| *Bacillus cereus* | ATCC 11778 | 128 | 128 | 16 | 32 | 16 | 32 | 64 | 8 |
| *Bacillus megaterium* | ATCC 9885 | | | 0.5 | 0.13 | 0.063 | 0.25 | 0.5 | 0.063 |
| *Micrococcus luteus* | ATCC 9341 | 0.5 | 0.5 | 0.25 | 0.25 | 0.016 | 0.25 | 0.5 | 0.016 |
| *Staphylococcus aureus* | ATCC 6538p | 4 | 4 | 4 | 4 | 0.5 | 4 | 2 | 0.13 |
| *Staphylococcus aureus* | ATCC 10537 | 4 | 2 | 2 | 2 | 0.25 | 2 | 2 | 0.13 |
| *Staphylococcus epidermidis* | ATCC 12228 | 2 | 2 | 2 | 2 | 0.13 | 2 | 1 | 0.031 |
| *Streptococcus faecalis* | ATCC 29212 | >128 | >128 | >128 | >128 | 32 | >128 | >128 | 16 |
| *Acinetobacter calcoaceticus* | ATCC 15473 | 16 | 4 | 16 | 16 | 16 | 32 | 8 | 2 |
| *Citrobacter freundii* | ATCC 8090 | 0.13 | 0.063 | 0.25 | 0.25 | 1 | 1 | 0.063 | 0.063 |
| *Enterobacter aerogenes* | ATCC 29751 | 4 | 1 | 0.5 | 2 | 2 | 2 | 1 | 0.25 |
| *Enterobacter cloacae* | ATCC 27508 | 0.031 | 0.016 | 0.063 | 0.063 | 0.13 | 0.25 | 0.016 | <=0.008 |
| *Escherichia coli* | ATCC 10536 | 0.13 | 0.063 | 0.25 | 0.25 | 0.5 | 0.5 | 0.063 | 0.063 |
| *Escherichia coli* | ATCC 25922 | 0.13 | 0.13 | 0.25 | 0.25 | 0.5 | 0.5 | 0.063 | 0.063 |
| *Klebsiella pneumoniae* | ATCC 10031 | 0.13 | 0.063 | 0.13 | 0.13 | 0.031 | 0.25 | 0.063 | <=0.008 |
| *Morganella morganii* | ATCC 8076h | <=0.008 | <=0.008 | <=0.008 | <=0.008 | 0.016 | 0.031 | <=0.008 | <=0.008 |
| *Proteus mirabilis* | ATCC 25933 | 0.063 | 0.031 | 0.25 | 0.13 | 0.5 | 0.5 | 0.063 | 0.063 |
| *Proteus vulgaris* | ATCC 6059 | 0.13 | 0.063 | 0.13 | 0.13 | 0.5 | 0.5 | 0.063 | 0.13 |
| *Providencia rettgeri* | ATCC 9250 | <=0.008 | <=0.008 | 0.031 | <=0.008 | <=0.008 | 0.031 | <=0.008 | <=0.008 |
| *Pseudomonas aeruginosa* | ATCC 25619 | 2 | 2 | 2 | 1 | 2 | 4 | 1 | 0.5 |
| *Pseudomonas aeruginosa* | ATCC 27853 | 2 | 2 | 2 | 1 | 8 | 4 | 2 | 2 |
| *Pseudomonas aeruginosa* | ATCC 10145 | 4 | 2 | 4 | 2 | 16 | 8 | 4 | 4 |
| *Salmonella typhimurium* | ATCC 14028 | 0.5 | 0.13 | 0.5 | 0.5 | 2 | 2 | 0.25 | 0.25 |
| *Serratia marcescens* | ATCC 27117 | 0.5 | 0.13 | 0.5 | 0.5 | 1 | 2 | 0.13 | 0.13 |
| *Shigella flexneri* | ATCC 11836 | 0.063 | 0.031 | 0.13 | 0.063 | 0.25 | 0.25 | 0.031 | 0.016 |
| *Shigella sonnei* | ATCC 11060 | 0.25 | 0.063 | 0.25 | 0.25 | 0.5 | 0.5 | 0.063 | 0.063 |

| Strains | | MIC, μg/ml | | | | |
|---|---|---|---|---|---|---|
| | | I-47 | I-48 | I-49 | I-50 | Ceftazidime |
| *Bacillus cereus* | ATCC 11778 | 8 | 64 | 32 | 8 | 128 |
| *Bacillus megaterium* | ATCC 9885 | 0.13 | 0.5 | 0.25 | 0.13 | 0.25 |
| *Micrococcus luteus* | ATCC 9341 | <=0.008 | 0.5 | 0.031 | <=0.008 | 1 |
| *Staphylococcus aureus* | ATCC 6538p | 0.25 | 4 | 0.25 | 0.13 | 16 |
| *Staphylococcus aureus* | ATCC 10537 | 0.13 | 4 | 0.25 | 0.13 | 8 |
| *Staphylococcus epidermidis* | ATCC 12228 | 0.031 | 2 | 0.13 | 0.063 | 8 |
| *Streptococcus faecalis* | ATCC 29212 | 32 | >128 | 16 | 8 | >128 |
| *Acinetobacter calcoaceticus* | ATCC 15473 | 4 | 4 | 8 | 4 | 4 |
| *Citrobacter freundii* | ATCC 8090 | 0.13 | 0.13 | 0.25 | 0.13 | 0.25 |
| *Enterobacter aerogenes* | ATCC 29751 | 0.5 | 2 | 1 | 0.5 | 8 |
| *Enterobacter cloacae* | ATCC 27508 | 0.016 | 0.031 | 0.031 | 0.016 | 0.063 |
| *Escherichia coli* | ATCC 10536 | 0.13 | 0.13 | 0.25 | 0.13 | 0.13 |
| *Escherichia coli* | ATCC 25922 | 0.13 | 0.13 | 0.25 | 0.13 | 0.13 |
| *Klebsiella pneumoniae* | ATCC 10031 | <=0.008 | 0.063 | 0.016 | <=0.008 | 0.13 |
| *Morganella morganii* | ATCC 8076h | <=0.008 | <=0.008 | <=0.008 | <=0.008 | 0.016 |
| *Proteus mirabilis* | ATCC 25933 | 0.13 | 0.063 | 0.5 | 0.25 | 0.063 |
| *Proteus vulgaris* | ATCC 6059 | 0.13 | 0.13 | 0.5 | 0.25 | 0.063 |
| *Providencia rettgeri* | ATCC 9250 | <=0.008 | <=0.008 | <=0.008 | <=0.008 | <=0.008 |
| *Pseudomonas aeruginosa* | ATCC 25619 | 1 | 2 | 1 | 1 | 1 |
| *Pseudomonas aeruginosa* | ATCC 27853 | 2 | 2 | 8 | 4 | 1 |
| *Pseudomonas aeruginosa* | ATCC 10145 | 8 | 4 | 16 | 4 | 2 |
| *Salmonella typhimurium* | ATCC 14028 | 0.25 | 0.5 | 1 | 0.5 | 0.25 |
| *Serratia marcescens* | ATCC 27117 | 0.13 | 0.25 | 0.5 | 0.25 | 0.13 |
| *Shigella flexneri* | ATCC 11836 | 0.016 | 0.063 | 0.063 | 0.031 | 0.063 |
| *Shigella sonnei* | ATCC 11060 | 0.13 | 0.13 | 0.25 | 0.13 | 0.13 |

TABLE 2

Antibacterial Activity against Clinically isolated-Strains

| Compound | Strains (No. tested) | MIC(mcg/ml)* | | |
|---|---|---|---|---|
| | | Range | 50% | 90% |
| I-1 | *Escherichia coli* (38) | 0.016~0.25 | 0.063 | 0.13 |

TABLE 2-continued

Antibacterial Activity against Clinically isolated-Strains

| Compound | Strains (No. tested) | MIC(mcg/ml)* Range | 50% | 90% |
|---|---|---|---|---|
| | *Klebsiella pneumoniae* (10) | 0.063∼0.25 | 0.063 | 0.13 |
| | Staphylococcus aureus methicillin susceptible (42) | 2∼4 | 2 | 2 |
| | *Staphylococcus aureus* methicillin resistant (7) | 32∼>128 | >128 | >128 |
| | *Pseudomonas aeruginosa* (54) | 0.13∼64 | 1 | 4 |
| I-2 | *Escherichia coli* (38) | 0.016∼0.25 | 0.063 | 0.13 |
| | *Klebsiella pneumoniae* (10) | 0.031∼0.25 | 0.13 | 0.13 |
| | *Staphylococcus aureus* methicillin susceptible (42) | 1∼4 | 2 | 2 |
| | *Staphylococcus aureus* methicillin resistant (7) | 32∼>128 | >128 | >128 |
| | *Pseudomonas aeruginosa* (54) | 0.13∼64 | 2 | 4 |
| I-4 | *Escherichia coli* (38) | =0.008∼0.25 | 0.031 | 0.063 |
| | *Klebsiella pneumoniae* (10) | 0.031∼0.13 | 0.031 | 0.13 |
| | *Staphylococcus aureus* methicillin susceptible (42) | 2∼4 | 4 | 4 |
| | *Staphylococcus aureus* methicillin resistant (7) | >32 | >32 | >32 |
| | *Pseudomonas aeruginosa* (54) | 1∼>128 | 4 | 16 |
| I-5 | *Escherichia coli* (38) | <=0.008∼0.5 | 0.063 | 0.13 |
| | *Klebsiella pneumoniae* (10) | 0.063∼0.25 | 0.063 | 0.25 |
| | *Staphylococcus aureus* methicillin susceptible (42) | 2∼8 | 4 | 4 |
| | *Staphylococcus aureus* methicillin resistant (7) | 64∼>128 | >128 | >128 |
| | *Pseudomonas aeruginosa* (54) | 0.25∼64 | 4 | 8 |
| I-7 | *Escherichia coli* (38) | 0.008∼0.016 | 0.016 | 0.063 |
| | *Klebsiella pneumoniae* (10) | 0.016∼0.063 | 0.016 | 0.031 |
| | *Staphylococcus aureus* methicillin susceptible (42) | 2∼4 | 4 | 4 |
| | *Staphylococcus aureus* methicillin resistant (7) | >32 | >32 | >32 |
| | *Pseudomonas aeruginosa* (54) | 0.5∼128 | 4 | 16 |
| I-14 | *Escherichia coli* (38) | =0.008∼0.25 | 0.031 | 0.063 |
| | *Klebsiella pneumoniae* (10) | 0.016∼0.063 | 0.031 | 0.063 |
| | *Staphylococcus aureus* methicillin susceptible (42) | 0.5∼4 | 4 | 4 |
| | *Staphylococcus aureus* methicillin resistant (7) | 4∼>128 | >128 | >128 |
| | *Pseudomonas aeruginosa* (54) | 0.25∼64 | 1 | 4 |
| I-19 | *Escherichia coli* (38) | 0.016∼0.25 | 0.063 | 0.13 |
| | *Klebsiella pneumoniae* (10) | 0.031∼0.25 | 0.13 | 0.13 |
| | *Staphylococcus aureus* methicillin susceptible (42) | 2∼8 | 2 | 4 |
| | *Staphylococcus aureus* methicillin resistant (7) | 32∼>128 | >128 | >128 |
| | *Pseudomonas aeruginosa* (54) | 0.25∼32 | 2 | 8 |
| I-16 | *Escherichia coli* (38) | 0.031∼0.5 | 0.13 | 0.25 |
| | *Klebsiella pneumoniae* (10) | 0.063∼0.25 | 0.13 | 0.13 |
| | *Staphylococcus aureus* methicillin susceptible (42) | 0.25∼0.5 | 0.25 | 0.25 |
| | *Staphylococcus aureus* methicillin resistant (7) | 8∼>32 | >32 | >32 |
| | *Pseudomonas aeruginosa* (54) | 0.5∼64 | 4 | 16 |
| I-17 | *Escherichia coli* (38) | 0.063∼1 | 0.13 | 0.25 |
| | *Klebsiella pneumoniae* (10) | 0.13∼0.25 | 0.25 | 0.25 |
| | *Staphylococcus aureus* methicillin susceptible (42) | 0.5∼1 | 0.5 | 1 |
| | *Staphylococcus aureus* methicillin resistant (7) | 2∼128 | 16 | 64 |
| | *Pseudomonas aeruginosa* (54) | 0.5∼128 | 4 | 8 |
| I-18 | *Escherichia coli* (38) | 0.031∼1 | 0.13 | 0.25 |
| | *Klebsiella pneumoniae* (10) | 0.13 | 0.13 | 0.13 |
| | *Staphylococcus aureus* methicillin susceptible (42) | 0.13∼0.25 | 0.25 | 0.25 |
| | *Staphylococcus aureus* methicillin resistant (7) | 8∼>128 | 128 | >128 |
| | *Pseudomonas aeruginosa* (54) | 0.5∼16 | 4 | 8 |
| I-20 | *Escherichia coli* (38) | 0.016∼0.5 | 0.063 | 0.25 |
| | *Klebsiella pneumoniae* (10) | 0.063∼0.25 | 0.13 | 0.13 |
| | *Staphylococcus aureus* methicillin susceptible (42) | 0.25∼0.5 | 0.5 | 0.5 |
| | *Staphylococcus aureus* methicillin resistant (7) | 1∼128 | 16 | 32 |
| | *Pseudomonas aeruginosa* (54) | 1∼64 | 4 | 16 |
| I-30 | *Escherichia coli* (38) | 0.031∼0.5 | 0.13 | 0.25 |
| | *Klebsiella pneumoniae* (10) | 0.063∼0.25 | 0.13 | 0.25 |

TABLE 2-continued

| Compound | Strains (No. tested) | MIC(mcg/ml)* Range | 50% | 90% |
|---|---|---|---|---|
| | Antibacterial Activity against Clinically isolated-Strains | | | |
| | *Staphylococcus aureus* methicillin susceptible (42) | 2~8 | 2 | 4 |
| | *Staphylococcus aureus* methicillin resistant (7) | 32~>128 | >128 | >128 |
| | *Pseudomonas aeruginosa* (54) | 0.13~32 | 2 | 4 |
| I-45 | *Escherichia coli* (38) | 0.031~0.25 | 0.13 | 0.13 |
| | *Klebsiella pneumoniae* (10) | 0.063~0.25 | 0.13 | 0.13 |
| | *Staphylococcus aureus* methicillin susceptible (42) | 2~4 | 2 | 2 |
| | *Staphylococcus aureus* methicillin resistant (7) | 64~>128 | >128 | >128 |
| | *Pseudomonas aeruginosa* (54) | 0.5~128 | 4 | 16 |
| I-46 | *Escherichia coli* (38) | 0.031~0.5 | 0.13 | 0.25 |
| | *Klebsiella pneumoniae* (10) | 0.063~0.25 | 0.13 | 0.13 |
| | *Staphylococcus aureus* methicillin susceptible (42) | 0.13~1 | 0.25 | 0.25 |
| | *Staphylococcus aureus* methicillin resistant (7) | 4~>32 | >32 | >32 |
| | *Pseudomonas aeruginosa* (54) | 0.5~32 | 4 | 8 |
| I-47 | *Escherichia coli* (38) | 0.016~0.5 | 0.063 | 0.25 |
| | *Klebsiella pneumoniae* (10) | 0.063~0.25 | 0.25 | 0.25 |
| | *Staphylococcus aureus* methicillin susceptible (42) | 0.13~0.25 | 0.25 | 0.25 |
| | *Staphylococcus aureus* methicillin resistant (7) | 4~128 | 64 | 64 |
| | *Pseudomonas aeruginosa* (54) | 0.5~16 | 4 | 16 |
| Ceftazidime | *Escherichia coli* (38) | 0.063~4 | 0.13 | 0.13 |
| | *Klebsiella pneumoniae* (10) | 0.063~0.5 | 0.063 | 0.5 |
| | *Staphylococcus aureus* methicillin susceptible (42) | 2~16 | 8 | 8 |
| | *Staphylococcus aureus* methicillin resistant (7) | 64~>128 | 128 | >128 |
| | *Pseudomonas aeruginosa* (54) | 0.5~128 | 4 | 16 |

<Note>
*Broth microdilution test

In-vivo absorbency of the invented compounds(I) was studied in SD rat(♂) weighing 220~340 g, as follows: The test compound was intravenously administered in a dose of 20 mg/kg respectively to 2~5 rats. The blood samples from the femoral vein of the rats were taken every hour after administration, and analyzed by bio-assay(agar well method). The results were shown in Table 3.

TABLE 3

| Compounds | | I-1 | I-2 | I-4 | I-5 | I-7 | I-8 | I-15 | I-16 | I-30 | I-31 | I-32 | I-33 | I-34 | I-45 | CTZ |
|---|---|---|---|---|---|---|---|---|---|---|---|---|---|---|---|---|
| In-vivo Absorbency (Plasma Concentrations & Pharmacokinetic Parameters) | | | | | | | | | | | | | | | | |
| Plasma Conc. (μg/ml) | Sampling Time 0.5 (min) | | | | | | | | | | 208 | 162 | 194 | 181 | | |
| | 1 | 152 | 55 | 64 | 134 | 128 | 121 | 148 | 149 | 148 | | | | | 147 | 135 |
| | 2.5 | 101 | 33 | 42 | 91 | 83 | 92 | 104 | 106 | 100 | 85 | 75 | 79 | 89 | 84 | 94 |
| | 5 | 65 | 22 | 32 | 72 | 59 | 64 | 71 | 79 | 80 | 62 | 53 | 55 | 68 | 67 | 71 |
| | 10 | 45 | 14 | 14 | .49 | 43 | 48 | 53 | 52 | 54 | 45 | 35 | 36 | 47 | 52 | 53 |
| | 20 | 29 | 7.3 | 7.3 | 29 | 29 | 36 | 22 | 32 | 29 | 30 | 21 | 21 | 31 | 29 | 26 |
| | 40 | 14 | 4.5 | 4.5 | 13 | 15 | 15 | 10 | 13 | 17 | 14 | 13 | 13 | 15 | 16 | 10 |
| | 60 | 7.7 | 2.6 | 2.6 | 9.7 | 8.1 | 8.7 | 2.4 | 8.8 | 9.6 | 7.7 | 7.5 | 7.0 | 7.8 | 11 | 4.7 |
| | 120 | 1.8 | 0.4 | 0.4 | 3.0 | 1.9 | 2.7 | 0.6 | 1.9 | 2.7 | 1.6 | 1.8 | 1.2 | 1.2 | 3.6 | 1.6 |
| | 150 | | | | | | | | | 1.3 | | | | | | |
| Pharmacokinetic Parameters | $T\frac{1}{2}$ (α)(min) | 3 | 2 | 2 | 5 | 2 | 6 | 3 | 4 | 4 | 6 | 3 | 2 | 1 | 4 | 5 |
| | $T\frac{1}{2}$ (β)(min) | 26 | 23 | 26 | 36 | 26 | 32 | 29 | 24 | 30 | 27 | 29 | 24 | 21 | 38 | 20 |
| | AUC (μg.min/ml) | 2118 | 683 | 1115 | 2337 | 2140 | 2604 | 2604 | 2304 | 2510 | 1830 | 1829 | 1829 | 2230 | 2572 | 1863 |
| n | | 4 | 4 | 5 | 5 | 5 | 5 | 3 | 5 | 3 | 5 | 5 | 5 | 4 | 2 | 5 |

<Note>
Two-Compartment Model
Dose: 20 mg/kg
Tested animal: SD male Rat (220~340 g)

The present invention is described in detail by the following Preparations and Examples:

PREPARATION 1

Preparation of 4,6-diamino-1-methyl-2(1H)-pyrimidinethione

Sodium metal (4.6 g) was added to dried ethyl alcohol (100 ml), and refluxed for an hour. After N-methylthiourea (9 g) and malononitrile (6.6 g) were added thereto, the reaction mixture was refluxed for 24 hours. The reaction mixture was cooled to room temperature and neutralized with conc. hydrochloric acid. The precipitates were filtered, washed with water (20 ml) and ethyl alcohol (50 ml) and dried in vacuo to give the above-indicated compound (8.1 g) in pale yellow solid.

m.p.: 185° C.~(decomp.).

NMR: δ ($D_2O$+acetone-$d_6$) 3.80(s, 3H), 5.39(s, 1H).

MS(EI): 156(M+), 126.

IR(KCl. $cm^{-1}$): 3441, 3335(N—H), 1682(C═N), 1095(C═S).

PREPARATION 2

Preparation of 4,6-diamino-1-ethyl-2(1H)-pyrimidinethione

Sodium metal (4.6 g) was added to dried ethyl alcohol (100 ml), and refluxed for an hour. After N-ethylthiourea (10.4 g) and malononitrile (6.6 g) were added thereto, the obtained reaction mixture was refluxed for 48 hours. The reaction mixture was cooled to room temperature and neutralized with conc. hydrochloric acid. The precipitates were filtered, washed with ethyl alcohol (50 ml), and the filtrate was concentrated under reduced pressure. The residue was chromatographed over silica gel to give the above-indicated compound (6.2 g) in yellow solid.

m.p.: 197° C.~(decomp.).

NMR: δ ($D_2O$+acetone-$d_6$) 1.32(t, 3H), 4.61(q, 2H), 5.68(s, 1H).

MS(EI): 170(M+), 142.

IR(KCl, $cm^{-1}$): 3480, 3200(N—H), 1665(C═N), 1130(C═S).

PREPARATION 3

Preparation of 4,6-diamino-1-propyl-2(1H)-pyrimidinethione

Sodium metal (4.6 g) was added to dried ethyl alcohol (100 ml), and refluxed for an hour. After N-propylthiourea (11.8 g) and malononitrile (6.6 g) were added thereto, the reaction mixture was refluxed for 72 hours, cooled to room temperature, and neutralized with conc. hydrochloric acid. The precipitates were filtered, washed with ethyl alcohol (50 ml), and the filtrate was concentrated under reduced pressure. The residue was chromatographed over silica gel to give the above-indicated compound (5.7 g) in yellowish brown solid.

m.p.: 195° C.~(decomp.).

NMR: δ ($D_2O$+acetone-$d_6$) 0.96(t, 3H), 1.81(m, 2H), 4.51(t, 2H), 5.46(s, 1H).

MS(EI): 184(M+), 142.

IR(KCl, $cm^{-1}$): 3310, 3200(N—H), 1634(C═N), 1150(C═S).

PREPARATION 4

Preparation of 1-butyl-4,6-diamino-2(1H)-pyrimidinethione

Sodium metal (4.6 g) was added to dried ethyl alcohol (100 ml), and refluxed for an hour. After N-butylthiourea (13.2 g) and malononitrile (6.6 g) were added thereto, the reaction mixture was refluxed for 72 hours, cooled to room temperature and neutralized with conc. hydrochloric acid. The precipitates were filtered, washed with ethyl alcohol (50 ml), and the filtrate was concentrated under reduced pressure. The residue was chromatographed over silica gel to give the above-indicated compound (4.6 g) in brown solid.

m.p.: 195° C.~(decomp.).

NMR: δ ($D_2O$+acetone-$d_6$) 0.88(t, 3H), 1.36(m, 2H), 1.69(m, 2H), 4.59(t, 2H), 5.41(s, 1H).

MS(EI): 198(M+), 142.

IR(KCl, $cm^{-1}$): 3320, 3200(N—H), 1640(C═N), 1110(C═S).

PREPARATION 5

Preparation of 1-allyl-4,6-diamino-2(1H)-pyrimidinethione

Sodium metal (4.6 g) was added to dried ethyl alcohol (100 ml), and refluxed for an hour. After N-allylthiourea (11.6 g) and malononitrile (6.6 g) were added thereto, the reaction mixture was refluxed for 72 hours, cooled to room temperature and neutralized with conc. hydrochloric acid. The precipitates were filtered, washed with ethyl alcohol (50 ml), and the filtrate was concentrated under reduced pressure. The residue was chromatographed over silica gel to give the above-indicated compound (6.2 g) in yellowish brown solid.

m.p.: 193° C.~(decomp.).

NMR: δ ($CD_3OD$) 5.42(s, 1H), 5.16~6.11(m, 5H).

MS(EI): 182(M+), 142.

IR(KCl, $cm^{-1}$): 3310, 3260(N—H), 1645(C═N), 1012(C═S).

PREPARATION 6

Preparation of 1,4,6-triamino-2(1H)-pyrimidinethione

Sodium metal (4.6 g) was added to dried ethyl/alcohol (100 ml), and refluxed by heating for an hour. After malononitrile (6.6 g) and thiosemicarbazide(9.1 g) were added thereto, the reaction mixture was refluxed for 24 hours, cooled to room temperature. The precipitates were filtered, washed with ethyl alcohol (50 ml), and dried under reduced pressure to give the above-indicated compound (8.3 g) in white solid.

m.p.: 225° C.~(decomp.)

NMR: δ ($D_2O$+acetone-$d_6$) 5.42(s, 1H).

MS(EI): 157(M+), 126.

IR(KCl, $cm^{-1}$): 3440, 3420(N—$NH_2$), 3310, 3260(N—H), 1645(C═N), 1138(C═S).

PREPARATION 7

Preparation of 4,6-diamino-1,5-dimethyl-2(1H)-pyrimidinethione

A. Preparation of methyl (±)-2-cyanopropionate

To (±)-2-bromopropionic acid (81.08 g) was added water (70 ml). Sodium carbonate (28.62 g) was added slowly over an hour and dissolved therein. A solution of potassium cyanide(37.77 g) dissolved in water (75 ml) was added, and heated to about 50° C. Accordingly as the reaction progressed, the temperature of the reaction solution rose to 90° C. The reaction solution was stirred at 90°~100° C. for an hour, cooled to room temperature, and neutralized with conc. hydrochloric acid (60 ml). Afterwards, the thus neutralized solution was concentrated under reduced pressure, ethyl alcohol(300 ml) was added to the concentrated solution. The ethanolic solution was concentrated under reduced pressure again. To the residue was added ethyl alcohol (700 ml). followed by filtration. After conc. sulfuric acid(1~5 ml) was added to the filtrate, the solution was refluxed for 5 hours and distilled to remove about 300 ml of ethylalcohol. The solution was concentrated under reduced pressure, and residue was added to sodium carbonate saturated solution (200 ml). After extraction with ether (400 ml), the separated organic layer was washed with a 10% saline solution (500 ml) and a saturated saline solution (200 ml), and dried over anhydrous magnesium sulfate, filtered and then concentrated. The residue was distilled under reduced pressure to give the colorless above-indicated compound(44.74 g).

Yield: 70%.

b.p.: 87°~90° C./12 torr.

NMR: δ ($CDCl_3$) 1.33(t, 3H), 1.60(d, 3H), 3.55(q, 1H), 4.28(q, 2H).

B. Preparation of (±)-2-cyanopropionamide

To ethyl (±)-2-cyanopropionate (44.74 g) was added conc. aqueous ammonia solution (200 ml). The reaction mixture was stirred at room temperature for an hour and concentrated under reduced pressure. After addition of ethyl alcohol (200 ml), the ethanolic solution was concentrated again. The residue was dried in a vacuum oven to give the green above-indicated compound (33.00 g).

Yield: 96%.

NMR: δ (DMSO-$d_6$) 1.40(d, 3H), 3.74(q, 1H), 7.39(bs, 1H), 7.82(bs, 1H).

C. Preparation of 2-methylmalononitrile (±)-2-Cyanopropionamide (33.00 g), and phosphorus pentachloride (28.07 g) ground minutely in a mortar were added to a flask equipped with a distillation apparatus. While producing a vacuum using a water pump, the mixture was stirred at 90°~100° C. for 20 minutes to remove hydrogen chloride gas and phosphorus oxychloride, and distilled under reduced pressure in a bath heated to 180° C. to give the above-indicated compound(15.67 g). This compound was solidified to a white solid state at room temperature.

Yield: 58%.

b.p.: 86°~89° C./12 torr.

NNR: δ (DMSO-$d_6$) 1.63(d, 3H), 4.76(q, 1H).

D. Preparation of 4,6-diamino-1,5-dimethyl-2(1H)-pyrimidinethione

After sodium metal (9.01 g) was dissolved in dried ethyl/alcohol (150 ml) under nitrogen stream, N-methylthiourea(17.67 g) was added thereto and refluxed for an hour. 2-Methylmalononitrile (17.67 g) was added to the solution and then refluxed for 15 hours. The reaction mixture was cooled to 40° C. and filtered. The filtered solid was washed with cold ethyl alcohol (100 ml) and dried to give the pale yellow above-indicated compound(25.20 g).

m.p.: 230° C.~(decomp.).

Yield: 76%.

TLC: Rf 0.2($MeOH/CH_2Cl_2$=1/5).

NMR: δ (DMSO-$d_6$) 1.6(s, 1H), 3.60(s, 3H), 4.92(bs, 4H).

MS(EI): 170(M+), 156.

IR(KCl, $cm^{-1}$): 3480, 3360(N—H), 1623(C═N), 1090(C═S).

PREPARATION 8

Preparation of 4,6-diamino-1-ethyl-5-methyl-2(1H)-pyrimidinethione

After Sodium metal (2.30 g) was dissolved in dried ethyl alcohol (50 ml), N-ethylthiourea (5.20 g) was added and refluxed for an hour. 2-Methylmalononitrile (4.0 g) was added to the solution and then refluxed for 15 hours. The reaction mixture was cooled to room temperature, neutralized with conc. hydrochloric acid, and filtered. After water (20 ml) was added to the filtered solid, the mixture was stirred for 10 minutes, and filtered. The filtered solid was dried to give the pale yellow above-indicated compound(3.57 g).

m.p.: 281° C.~(decomp.).

Yield: 39%.

NMR: δ (DMSO-$d_6$) 1.15(t, 3H), 1.75(s, 3H), 4.57(bs, 2H), 6.24(bs, 2H), 6.68(bs, 2H).

MS(EI): 184(M+), 156.

IR(KCl, $cm^{-1}$): 3418, 3300(N—H), 1620(C═N), 1105(C═S).

PREPARATION 9

Preparation of 5-methyl-1,4,6-triamino-2(1H)-pyrimidinethione

After sodium metal (2.30 g) was dissolved in dried ethyl alcohol (50 ml), thiosemicarbazide (4.55 g) was added thereto and refluxed for an hour. 2-Methylmalononitrile (4.0 g) was added to the mixture and then refluxed for 15 hours. The reaction mixture was cooled to 40° C., and filtered, washed with ethyl alcohol (50 ml), and dried to give the pale yellow above-indicated compound(3.78 g).

m.p.: 215° C.~(decomp.).

Yield: 44%.

NMR: δ (DMSO-$d_6$) 1.68(s, 3H), 3.48(bs, 2H), 5.20(bs, 2H), 5.95(bs, 2H).

MS(EI): 171(M+), 156.

IR(KCl, $cm^{-1}$): 3470, 3340(N—H), 1622(C═N), 1060(C═S).

PREPARATION 10

Preparation of 4,6-diamino-5-ethyl-1-methyl-2(1H)-pyrimidinethione

A. Preparation of methyl (±)-2-cyanobutyrate

To (±)-2-bromobutyric acid(167.01 g) was added water (150 ml). Sodium carbonate (54.05 g) was added slowly over an hour and dissolved therein. A solution of potassium cyanide (68.55 g) dissolved in water (150 ml) was added, and heated to about 50° C. Accordingly as the reaction progressed, the temperature of the reaction solution rose to 80° C. The reaction solution was stirred at 80°~90° C. for an hour, cooled to room temperature, and neutralized with conc. hydrochloric acid (120 ml). Afterwards, the such neutralized solution was concentrated under reduced pressure, and ethyl alcohol (500 ml) was added to the residue. The obtained ethanolic solution was concentrated under reduced pressure again. To the residue was added ethyl alcohol (700 ml), followed by filtration. After conc. sulfuric acid (3 ml) was added to the filtrate, the solution was refluxed for 5 hours and distilled to remove about 300 ml of ethyl alcohol. The solution was concentrated under reduced prrssure, and the residue was added to sodium carbonate saturated solution(400 ml). After extraction with ether (500 ml), the separated organic layer was washed with a 10% saline solution (500 ml) and a saturated saline solution(300 ml), dried over anhydrous magnesium sulfate, filtered and then concentrated. The residue was distilled under reduced pressure to give the colorless above-indicated compound(49.90 g).

Yield: 35%.

b.p.: 93°~96° C./12 torr.

NMR: δ ($CDCl_3$) 1.14(t, 3H), 1.34(t, 3H), 2.01(m, 2H), 3.47(t, 1H), 4.28(q, 2H).

B. Preparation of (±)-2-cyanobutyramide

To ethyl (±)-2-cyanobutyrate (49.90 g) was added ethylalcohol (40 ml). After conc. aqueous ammonia solution(200 ml) was added therein over 10 minutes, the solution was stirred at 30°~40° C. for 30 minutes. Ether(500 ml) was added to the solution and stirred for 10 minutes. The precipitates were filtered, and dried to give the colorless above-indicated compound(31.96 g).

Yield: 81%.

NMR: δ (DMSO-$d_6$) 0.98(t, 3H), 1.83(m, 2H), 3.63(t, 1H), 7.43(bs, 1H), 7.76(bs, 1H).

C. Preparation of 2-ethylmalononitrile (±)-2-Cyanobutyramide (31.96 g), and phosphorus pentachloride (23.85 g) ground in a mortar were added to a flask equipped with a distillation apparatus. With producing a vaccum using a water pump, the mixture was stirred at 90°~100° C. for 20 minutes to remove hydrogen chloride gas and phosphorus oxychloride, and distilled under reduced pressure in a bath heated to 180° C. to give the above-indicated compound (19.45 g).

Yield: 73%.

NMR: δ (DMSO-$d_6$) 1.26(t, 3H), 2.10(m, 2H), 3.73(t, 1H).

D. Preparation of 4,6-diamino-5-ethyl-1-methyl-2(1H)-pyrimidinethione

After sodium metal (2.30 g) was dissolved in dried ethylalcohol (50 ml), N-methylthiourea(4.50 g) was added therein and refluxed for an hour. 2-Ethylmalononitrile (4.70 g) was added to the solution and then refluxed for 18 hours. The reaction mixture was cooled to 40° C., neutralized with conc. hydrochloric acid, and filtered. To the filtered solid was added water(50 ml). The mixture was stirred for 10 minutes, filtered, and dried to give the white above-indicated compound (4.15 g).

m.p.: 259° C.~(decomp.).

Yield: 45%.

NMR: δ (DMSO-$d_6$) 0.92(t, 3H), 2.34(q, 2H), 3.82(s, 3H), 6.78(bs, 2H), 7.06(bs, 2H).

MS(EI): 184(M+), 169, 156.

IR(KCl. $cm^{-1}$): 3410, 3280(N—H), 1645(C=N), 1086(C=S).

PREPARATION 11

Preparation of 4,6-diamino-1,5-diethyl-2(1H)-pyrimidinethione

After sodium metal (2.30 g) was dissolved in dried ethyl alcohol (50 ml), N-ethylthiourea (5.20 g) was added thereto and refluxed for an hour. 2-Ethylmalononitrile (4.70 g) was added to the reflux mixture and then refluxed for 18 hours. The reaction mixture was cooled to 40° C., and adjusted pH to 5 with a 28% solution of hydrogen chloride dissolved in isopropyl alcohol. The reaction mixture was filtered, and then water(50 ml) was added to filtered solid. After the solution was stirred for 10 minutes and filtered again, the residue was dried to give the pale yellow above-indicated compound(2.79 g).

m.p.: 269° C.~(decomp.).

Yield: 28%.

NMR: δ (DMSO-$d_6$) 0.91(t, 3H), 1.16(t, 3H),2.28(q, 2H), 4.57(bs, 2H), 6.45(bs, 2H), 6.70(bs, 2H).

MS(EI): 198(M+), 170.

IR(KCl. $cm^{-1}$): 3380, 3320(N—H), 1646(C=N), 1101(C=S).

PREPARATION 12

Preparation of 4,6-diamino-1-phenyl-2(1H)-pyrimidinethione

Sodium metal (6.6 g) was added to dried ethylalcohol(100 ml), and refluxed for an hour. After N-phenylthiourea (9 g) and malononitrile (6.6 g) were added therein, the reaction mixture was refluxed for 72 hours. The reaction mixture was cooled to room temperature and neutralized with conc. hydrochloric acid. The precipitates were filtered, washed with water(20 ml) and ethylalcohol (50 ml), and dried in vacuo to give the above-indicated compound (4.7 g) in pale yellow.

m.p.: 281° C.~(decomp.).

NMR: δ (acetone-$d_6$) 5.48(s, 1H), 5.90(bs, 2H), 6.52(bs, 2H), 6.80~7.70(m, 5H).

MS(EI): 128($M^{30}$).

IR(KCl, $cm^{-1}$): 3464, 3400(N—H), 1630(C=N), 1182(C=S).

PREPARATION 13

Preparation of 1-(4-chlorophenyl)-4,6-diamino-2(1H)-pyrimidinethione

N-(4-Chlorophenyl)-thiourea (11 g) and malononitrile (6.6 g) were reacted in the same method as described in Preparation 12 to give the above-indicated compound (5.3 g).

m.p.: 275° C.~(decomp.).

NMR: δ (DMSO-$d_6$) 5.31(s, 1H), 6.38(bs, 2H), 6.87(bs, 2H), 7.18(d, 2H), 7.55(d, 1H).

MS(EI): 252(M+).

IR(KCl, $cm^{-1}$): 3460, 3400(N—H), 1630(C=N), 1095(C=S).

PREPARATION 14

Preparation of 4,6-diamino-1-(2,4-dimethylphenyl)-2(1H)-pyrimidinethione

N-(2,4-Dimethylphenyl)-thiourea (10.8 g) and malononitrile (6.6 g) were reacted in the same method as described in Preparation 12 to give the above-indicated compound (5.7 g).

m.p.: 212° C.~(decomp.).

NMR: δ (acetone-$d_6$) 2.08(s, 3H), 2.30(s, 3H), 5.58(s, 1H), 5.91(bs, 2H), 6.80~7.20 (m, 5H).

MS(EI): 246(M+).

IR(KCl, $cm^{-1}$): 3440, 3300(N—H), 1632(C=N), 1090(C=S).

PREPARATION 15

Preparation of 4,6-diamino-1-(2,6-dimethoxyphenyl)-2(1H)-pyrimidinethione

N-(2,6-Dimethoxyphenyl)-thiourea (11.5 g) and malononitrile (6.6 g) were reacted in the same method as described in Preparation 12 to give the above-indicated compound (6.2 g).

m.p.: 207° C.~(decomp.).

NMR: δ (acetone-$d_6$) 3.64(s, 6H), 5.44(s, 1H), 5.89(bs, 2H), 6.48(bs, 2H), 6.40~7.01 (m, 3H).

MS(EI): 278(M+).

IR(KCl, $cm^{-1}$): 3438, 3310(N—H), 1631(C=N), 1043(C=S).

PREPARATION 16

Preparation of 4,6-diamino-1-(4-hydroxyphenyl)-2(1H)-pyrimidinethione

N-(4-hydroxyphenyl)-thiourea (9.3 g) and malononitrile (6.6 g) were reacted in the same method as described in Preparation 12 to give the above-indicated compound (4.1 g).

m.p.: 282° C.~.

NMR: δ (DMSO-$d_6$)

5.30(s, 1H), 6.19(bs, 2H), 6.76(bs, 2H), 6.84(s, 4H), 9.78(bs, 1H).

MS(EI): 234(M+).

IR(KCl, cm−): 3480, 3470(N—H), 1640(C=N), 1038(C=S).

PREPARATION 17

Preparation of 1-cyclopropyl-4,6-diamino-2(1H)-pyrimidinethione

N-cyclopropylthiourea (6.2 g) and malononitrile (6.6 g) were reacted in the same method as described in Preparation 12 to give the pale yellow above-indicated compound(3.7 g).

m.p.: 242° C.~(decomp.).

NMR: δ (DMSO-$d_6$) 0.88~1.52(m, 4H), 2.80~3.16(m, 1H), 5.48(s, 1H).

MS(EI): 182(M+).

IR(KCl. $cm^{-1}$): 1580(C=N), 1015(C=S).

PREPARATION 18

Preparation of 3-acethoxymethyl-7-[(Z)-2-(2-aminothiazol-4-yl)-2-(methoxyimino)acetamido]-3cephem-4-carboxylic acid A. Preparation of ethyl (Z)-2-(methoxyimino)-2-[2-(triphenylmethyl) aminothiazol-4-yl]acetate To ethyl (Z)-2-(hydroxyimino)-2-[2-(triphenylmethyl)aminothiazol-4-yl]acetate(46 g) were added iodo methane(28.4 g), potassium carbonate (27.6 g) and dimethylsulfoxide(500 ml), and the mixture was stirred for 5 hours at room temperature. After ethyl ether(2 l) was added to the reaction mixture, the mixture was washed 5 times with distilled water(500 ml). The separated organic layer was dehydrated with anhydrous magnesium sulfate, filtered, and then concentrated. The residue was chromatographed over silica gel to give the above-indicated compound (35.2 g) as a pale yellow solid.

B. Preparation of (Z)-2-(methoxyimino)-2-[2-(triphenylmethyl) aminothiazol-4-yl]acetic acid After the compound(23.6 g) prepared in (A) was dissolved in a mixed solvent of ethyl alcohol(100 ml) and tetrahydrofuran(50 ml), aqueous 5N-sodium hydroxide solution (20 ml) was added thereto. The reaction mixture was stirred for 2 hours and neutralized with 5N-hydrochrolic acid (20 ml). After the organic solvent was removed under reduced pressure, ethyl acetate (1 l) was added to the residue, and then the reaction mixture was washed twice with distilled water(500 ml). The separated organic layer was dehydrated, and concentrated to give the above-indicated compound(20.7 g) in white solid.

C. Preparation of 3-acethoxymethyl-7-[(Z)-2-(2-aminothiazol-4-yl)-2-(methoxyimino)acetamido]-3-cephem-4-carboxylic acid The compound(4.4 g) prepared in (B) was dissolved in N,N-dimethyl acetamide(30 ml). To the solution were added triethylamine (3.5 ml) and mesithylene sulfonyl chloride(2.3 g) at 0° C., and stirred for 20 minutes. After adding 7-aminocephalosporanic acid (2.9 g), the reaction mixture was stirred again for 2 hours. To the mixture was added ethyl acetate (300 ml), and it was washed with 1%-hydrochloric acid (100 ml), sodium chloride solution(100 ml) and distilled water(200 ml). The separated organic layer was dehydrated, and concentrated. Formic acid (40 ml) was added to the residue. After the solution was stirred for 2 hours at room temperature, the recipitates were filtered off. The filtrate was concentrated under reduced pressure, triturated with ethyl ether (100 ml). The solid was filtered, washed, and dried to give the above-indicated compound(4.17 g) in pale yellow solid.

NMR: δ ($D_2O$+$NaHCO_3$) 2.08(s, 3H), 3.52(ABq, 2H), 3.99(s, 3H), 4.41(ABq, 2H), 5.23 (d, 1H), 5.84(d, 1H), 7.01(s, 1H).

PREPARATION 19

Preparation of 3-acethoxymethyl-7-[(Z)-2-(2-aminothiazol-4-yl)-2-(ethoxyimino)acetamido]-3-cephem-4-carboxylic acid A. Preparation of ethyl (Z)-2-(ethoxyimino)-2-[2-(triphenylmethyl) aminothiazol-4-yl]acetate To ethyl (Z)-2-(hydroxyimino)-2-[2-(triphenylmethyl)aminothiazol-4-yl]acetate(46 ) were added bromoethane(21.8 g), potassium carbonate (27.6 g) and dimethylsulfoxide(500 ml), and the solution was stirred for 7 hours at room temperature. After ethyl ether (2 l) was added thereto, the mixture was washed 5 times with distilled water (500 ml). The separated organic layer was dehydrated, and concentrated to give the above-indicated compound(41.4 g) as a pale yellow solid.

B. Preparation of (Z)-2-(ethoxyimino)-2-[2-(triphenylmethyl) aminothiazol-4-yl]acetic acid The compound (24.3 g) prepared in (A) was dissolved in a mixed solvent of ethyl alcohol(100 ml) and tetrahydrofuran (50 ml). After aqueous 5N-sodium hydroxide solution(20 ml) was added thereto, the reaction mixture was stirred for 2 hours at room temperature. The reaction mixture was neutralized with 5N-hydrochloric acid, and the organic solvent was removed under reduced pressure. To the residue was added ethyl acetate(1 l), and it was washed twice with distilled water(500 ml). The separated organic layer was dehydrated, and concentrated to give the above-indicated compound(19.8 g) in white solid.

C. Preparation of 3-acethoxymethyl-7-[(Z)-2-(2-aminothiazol-4-yl)-2-(ethoximino)acetamido]-3-cephem-4-carboxylic acid (Z)-2-(ethoxyimino)-2-[2-(triphenylmethyl)aminothiazol-4-yl]acetic acid (4.6 g) was reacted in the same method as described in (C) of Preparation 18 to give the above-indicated compound(3.98 g) in white solid.

NMR: δ($D_2O$+$NaHCO_3$) 1.31(t,3H), 2.02(s, 3H), 3.57(ABq, 2H), 4.07(q, 2H), 4.52(ABq, 2H), 5.20(d, 1H), 5.81(d, 1H), 7.00(s, 1H)

PREPARATION 20

Preparation of 3-acethoxymethyl-7-[(Z)-2-(2-aminothiazol-4-yl)-2-(2-carboxyprop-2-oxyimino)acetamido]-3-cephem-4-carboxylic acid dihydrochloride A. Preparation of ethyl (Z)-2-(2-tert-butoxycarbonylprop-2-oxyimino)-2-[2-(triphenylmethyl)aminothiazol-4-yl]acetate To ethyl (Z)-2-(hydroxyimino)-2-[2-(triphenylmethyl)aminothiazol-4-yl]acetate (46 g) were added potassium carbonate (27.6 g), tert-butyl-2-bromo-2-methylpropionate(24.1 g) and dimethylsulfoxide (300 ml), and then the solution was stirred for 6 hours at room temperature. Afterwards distilled water (100 ml) was added therein, the solution was stirred again for an hour. The precipitates were filtered, washed with distilled water(500 ml), and dried under reduced pressure to give the above-indicated compound(45.1 g) as a white solid.

B. Preparation of (Z)-2-(2-tert-butoxycarbonylprop-2-oxyimino)-2-[2-(triphenylmethyl)aminothiazol-4-yl]acetic acid The compound (30 g) prepared in (A) was reacted in the same method as described in (B) of Preparation 19. The resultant solid was recrystalized with methyl/alcohol(100 ml) to give the above-indicatedcompound (21 g) as a white solid.

C. Preparation of 3-acethoxymethyl-7-[(Z)-2-(2-aminothiazol-4-yl)-2-(2-carboxyprop-2-oxyimino)acetamido-3-cephem-4-carboxylic acid dihydrochloride (Z)-2-(2-tert-butoxycarbonylprop-2-oxyimino)-2-[2-(triphenylmethyl)aminothiazol-4-yl]acetic acid (5.7 g) was dissolved in N,N-dimethylformamide (30 ml). Triethylamine (3.5 ml) and mesithylenesulfonyl chloride(2.3 g) were added thereto at 0° C., and the obtained solution was stirred for 10 minutes. After 7-aminocephalosporanic acid (2.9 g) was added to the solution, the mixture was further stirred for 2 hours.

To the reaction mixture was added ethyl acetate(300 ml), and it was then washed with 1%-hydrochloric acid (100 ml), saline solution (100 ml), and distilled water (200 ml). The separated organic layer was dehydrated, and concentrated. To the residue were added formic acid (40 ml) and conc. hydrochloric acid(3 ml) at 0° C. After stirring for 2 hours, the solid was filtered off. The filtrate was concentrated under reduced pressure, and triturated with ethyl/ether. The solid was filtered, washed, and dried to give the above-indicated compound (3.87 g) in a yellow solid.

NMR: δ (Acetone-$d_6$) 1.50(s, 6H), 2.05(s, 3H), 3.53(ABq, 2H), 4.38(ABq, 2H), 5.12(d, 1H), 5.98(q, 1H), 7.05(s, 1H), 7.32(bs, 2H).

PREPARATION 21

Preparation of 3-acethoxymethyl-7-[(Z)-2-(2-aminothiazol-4-yl)-2-(1-carboxyeth-1-oxyimino)acetamido]-3-cephem-4-carboxylic acid A. Preparation of ethyl (Z)-2-(1-tert-butoxycarbonyleth-1-oxyimino)-2-[2-(triphenylmethyl)aminothiazol-4-yl]acetate After potassium carbonate (27.6 g), tert-butyl-2-bromopiopyonate (23 g) and dimethylsulfoxide(300 ml) were added to ethyl (Z)-2-(hydroxyimino)-2-[2-(triphenylmethyl)aminothiazol-4-yl]acetate(46 g), the mixture was stirred for 5 hours at room temperature. Ethylether (2 l) was added therein, and washed 5 times with distilled water(500 ml). Separated organic layer was dehydrated, and concentrated to give the above-indicated compound (51 g) in pale yellow solid.

B. Preparation of (Z)-2-(1-carboxyeth-1-oxyimino-2-[2-(triphenylmethyl) aminothiazol-4-yl]acetic acid The compound (27.9 g) prepared in (A) was dissolved in a mixed solvent of ethylalcohol(100 ml) and tetrahydrofuran(50 ml). After an 5N-sodium hydroxide aqueous solution (40 ml) was added therein, the solution was stirred for 2 hours at room temperature. The reaction mixture was neutralized with 5N-hydrochioric acid (40 ml), and the organic solvent was removed under reduced pressure. To the residue was added ethyl acetate(1 l), and it was washed twice with distilled water (500 ml). The separated organic layer was dehydrated and dried to give the above-indicated compound(23.1 g) in a pale yellow solid.

C. Preparation of 3-acethoxymethyl-7-[(Z)-2-(2-aminothiazol-4-yl)-2-(1-carboxyeth-1-oxyimino)acetamido]-3-cephem-4-carboxylic acid To a solution of (Z)-2-(1-carboxyeth-1oxyimino)-2-[2-(triphenylmethyl)aminothiazol-4-yl]acetic acid(5.6 g) dissolved in N,N-dimethyl acetamide(30 ml) were added triethylamine (1.4 ml) and mesithylene sulfonylchloride (2.3 g) at −10° C. After stirred for 50 minutes, triethylamine(2.8 ml) and 7-aminocephalosporanic acid (2.9 g) was added thereto. The reaction mixture was stirred again for 2 hours. After raising the temperature of the reaction mixture to room temperature, ethyl acetate (500 ml) was added thereto. The reaction mixture was washed twice with 1% hydrochloric acid (200 ml), saline solution (200 ml) and distilled water (200 ml). The separated organic layer was dehydrated, and concentrated. To the residue was added formic acid (50 ml). The solution was stirred for 2 hours, and the obtained solid was filtered off. The filtrate was concentrated udnder reduced pressure, and powder-solidified by addition of ethyl ether. The solid was filtered, washed, and dried to give the above-indicated compound(3.65 g).

NMR: δ ($D_2O+NaHCO_3$) 1.45(d, 3H), 2.07(s, 3H), 3.54(ABq, 2H), 4.64(q, 1H), 4.91(ABq, 2H), 5.24(d, 1H), 5.86(dd, 1H), 7.03(s, 1H).

PREPARATION 22

Preparation of 3-acethoxymethyl-7-[(Z)-2-(2-aminothiazol-4-yl)-2-(1-carboxymethyoxyimino)acetamido]-3-cephem-4 carboxylic acid A. Preparation of ethyl (Z)-2-(butoxycarbonylmethoxyimino)-2-[2-(triphenylmethyl)aminothiazol-4-yl]acetate To ethyl (Z)-2-(hydroxyimino)-2-[2-(triphenylmethyl)aminothiazol-4-yl]acetate(46 g) were added potassium carbonate(27.6 g), tert-butyl-2-bromopropionate(20 g) and dimethylsulfoxide(300 ml). The reaction mixture was stirred for 5 hours at room temperature, followed by addition of ethyl ether (2 l). After the reaction mixture was washed 5 times with distilled water(500 ml), the separated organic layer was dehydrated and concentrated to give the above-indicated compound(47.2 g) in a yellow solid.

B. Preparation of (Z)-2-(carboxymethoxyimino)-2-[2-(triphenylmethyl) aminothiazol-4-yl]acetate The compound(27.2 g) prepared in (A) was reacted in the same method as described in (B) of Preparation 21 to give the above-indicated compound (21.3 g) in a pale yellow solid.

C. Preparation of 3-acethoxymethyl-7-[(Z)-2-(2-aminothiazol-4-yl)-2-(1-carboxymethoxy-1-oxyimino)acetamido]-3-cephem-4-carboxylic acid To a solution of (Z)-2-(1-carboxymethoxy-1-oxyimino)-2-[2-(triphenylmethyl)aminothiazol-4-yl]acetic acid(5.4 g) dissolved in N,N-dimethylacetamide(30 ml) were added triethylamine(1.4 ml) and mesithylene sulfonylchloride (2.3 g) at −20° C. After stirring for an hour, triethylamine(2.8 ml) and 7-aminocephalosporanic acid(2.9 g) were added thereto. The solution was stirred again for 2 hours. After slowly raising the temperature of the reaction mixture to room temperature, ethyl acetate(500 ml) was added thereto. The reaction mixture was washed twice with 1% hydrochloric acid (200 ml), saline solution (200 ml) and distilled water(200 ml). The separated organic layer was dehydrated, and concentrated. To the residue was added formic acid (50 ml). The solution was stirred for 2 hours at room temperature and the formed solid was filtered off. The filtrate was concentrated under reduced pressure, and then triturated with ethyl ether. The solid was filtered, washed, and dried to give the above-indicated compound(3.32 g) in a yellow solid.

NMR: δ ($D_2O+NaHCO_3$) 2.06(s, 3H), 3.52(ABq, 2H), 4.73(ABq, 2H), 4.82(s, 2H), 5.21 (d, 1H), 5.84(d, 1H), 7.07(s, 1H).

PREPARATION 23

Preparation of 3-acethoxymethyl-7-[(Z)-2-(2-aminothiazol-4-yl)-2-(2-propen-1-oxyimino)acetamido]-3-cephem-4-carboxylic acid A. Preparation of ethyl (Z)-2-(2-propen-1-oxyimino)-2-[2-(triphenylmethyl)aminothiazol-4-yl]acetate The above-indicated compound (39.1 g) was prepared in the same method as described in (A) of Preparation 19, except that 3-bromopropyne24.2 (24.2 g) was used in place of bromoethane.

B. Preparation of (Z)-2-(2-propen-1-oxyimino)-2-[2-(triphenylmethyl)aminothiazol-4-yl]acetic acid The compound (24.9 g) obtained in (A) was reacted in the same method as described in (B) of Preparation 18 to give the above-indicated compound(21.1 g).

C. Preparation of 3-acethoxymethyl-7-[(Z)-2-(2-aminothiazol-4-yl)-2-(2-propen-1-oxyimino)acetamido]-3-cephem-4-carboxylic acid (Z)-2-(2-propen-1-oxyimino)-2-[2-(triphenylmethyl-)aminothiazol-4-yl)acetic acid(4.7 g) was reacted in the same method as described in (C) of Preparation 18 to give the above-indicated compound (4.05 g) in a pale yellow solid.

NMR: δ ($D_2O+NaHCO_3$) 2.07(s, 3H), 3.52(ABq, 2H), 4.81(s, 2H), 4.80(ABq, 2H), 5.23(d, 1H), 5.84(d, 1H), 5.15~6.24(m, 3H), 6.99(s, 1H).

PREPARATION 24

Preparation of 3-acethoxymethyl-7-[(Z)-2-(2-aminothiazol-4-yl)-2-(2-propyn-1-oxyimino)acetamido]-3-cephem-4-carboxylic acid A. Preparation of ethyl (Z)-2-(2-propyn-1-oxyimino)-2-[2-(triphenylmethyl)aminolthiazol-4-yl]acetate The above-indicated compound (30.7 g) was prepared in the same method as described in (A) of Preparation 19, except that 3-bromopropyne(14.9 g) was used in place of bromoethane.

B. Preparation of (Z)-2-(2-propyn-1-oxyimino)-2-[2-(triphenylmethyl) aminothiazol-4-yl]acetic acid The compound(24.8 g) prepared in (A) was reacted in the same method as described in (B) of Preparation 19 to give the above-indicated compound(21.1 g).

C. Preparation of 3-acethoxymethyl-7-[(Z)-2-(2-aminothiazol-4-yl)-2-(2-propyn-1-oxyimino)acetamido]-3-cephem-4-carboxylic acid (Z)-2-(2-propyn-1-oxyimino)-2-[2-(triphenylmethyl-)aminothiazol-4-yl)acetic acid (4.7 g) was reacted in the same method as described in (C) of Preparation 17 to give the above-indicated compound(3.95 g) in a yellow solid.

NMR: δ ($D_2O+NaHCO_3$)

2.06(s, 3H), 2.96(s, 1H), 3.56(ABq, 2H), 4.15(ABq, 2H), 4.84 (s, 2H), 5.11(d, 1H), 5.84(d, 1H), 7.05(s, 1H).

PREPARATION 25

Preparation of 3-acethoxymethyl-7-[(Z)-2-(5-amino-1,2,4-thiadiazol-4-yl)-2-(2-methoxyimino)acetamido]-3-cephem-4-carboxylic acid A. Preparation of 2-(hydroxyimino)malononitrile To a solution of malononitrile(66.1 g) dissolved in water(50 ml) and acetic acid(50 ml), was added slowly sodium nitrite(69 g) dissolved in water(100 ml) at 4° C., and then, stirred for 3 hours at room temperature. The reaction mixture was extracted 3 times with ethyl acetate(respectively, 500 ml, 250 ml and 250 ml), dried with anhydrous magnesium sulfate, and concentrated in vacuo. The residue was triturated with ethyl ether to give the above-indicated compound(92.5 g) in a white solid.

B. Preparation of 2-(methoxyimino)malononitrile

To a solution of 2-(hydroxyimino)malononitrile (95 g) dissolved in dimethylsulfoxide(200 ml) were added potassium carbonate(140 g) and dimethylsulfate(126.1 g). The reaction mixture was stirred for an hour at room temperature and ethyl ether (700 ml) was added thereto. After the mixture was washed 5 times with distilled water (1 l), the separated organic layer was dehydrated, concentrated, and then, distilled under reduced pressure to give the above-indicated compound(90 g) in a pale yellow liquid.

b.p.: 60°~65° C./20 torr.

NMR: δ ($CDCl_3$) 3.90(s, 3H).

C. Preparation of 2-cyano-2-(methoxyimino)acetamidinium acetate

To a mixed solution of ammonium chloride(14.2 g) dissolved in ethanol (90 ml) and conc. ammonium hydroxide aqueous solution (178 ml) was added 2-(methoxyimino)malononitrile(29 g) at −5°~0° C., and the mixture was stirred for 10 hours at these temperatures. The reaction mixture was extracted 3 times with methylene chloride (respectively, 450 ml, 100 ml and 100 ml), dehydrated, filtered, and concentrated. The residue was dissolved in ethyl acetate, and crystalized with acetic acid to give the above-indicated compound (20.5 g) in pale brown.

NMR: δ (DMSO-$d_6$) 1.90(s, 3H), 1.90(s, 3H), 4.18(s, 3H), 7.88(s, 1H).

D. Preparation of 2-(5-amino-1,2,4-thiadiazol-3-yl)-2-(methoxyimino) acetonitrile To a solution of 2-cyano-2-(methoxyimino)acetamidinium acetate (12.5 g) dissolved in methanol(100 ml) was added triethylamine(23.4 ml). Thereafter, bromine (12.9 g) was added slowly in small portions at −15° C., and the mixture was stirred for 5 minutes at −15°~−10° C., Potassium thiocyanate(3.7 g) dissolved in methanol(55 ml) was then added dropwise to the mixture at temperatures of −10° to −5° C., and the mixture stirred for 2 hours at 0° C. The reaction mixture was poured into ice water (1.2 l), and stirred for 30 minutes. The precipitates were filtered and dired to give the above-indicated compound (12.2 g) in pale brown.

NMR: δ (DMSO-$d_6$) 3.90(s, 3H), 8.37(s, 2H).

E. Preparation of 2-(5-amino-1,2,4-thiadiazol-3-yl)-2-(methoxyimino) acetic acid A solution of 2-(5-amino-1,2,4-thiadiazol-3-yl)-2-(methoxyimino) acetonitrile(12.2 g) dissolved in 4N-sodium hydroxide aqueous solution (250 ml) was stirred for 5 hours at temperatures of 50° to 55° C. The reaction mixture was cooled to room temperature and the adjusted pH to 1 with phosphoric acid, followed by extraction with a 3:1 (v/v) mixed solvent of ethyl acetate and tetrahydrofuran. After the separated organic layer was dried, filtered and concentrated the residue was triturated with ethyl ether, and the solid was filtered to give the above-indicated compound(11.2 g) in pale brown.

NMR: δ (DMSO-$d_6$) 3.91(s, 3H), 8.20(s, 2H).

F. Preparation of 3-acethoxymethyl-7-[(Z)-2-(5-amino-1,2,4-thiadiazol-3-yl)-2-(2-methoxyimino)acetamido]-3-cephem-4-carboxylic acid 2-(5-amino-1,2,4-thiadiazol-3-yl)-2-(methoxyimino)acetic acid (2.0 g) was dissolved in dried dimethylacetamide(20 ml), and then cooled to −10° C. Triethylamine(1.5 ml) and mesithylene sulfonyl chloride(2.3 g) was added therein, and the mixture was stirred for an hour at −10° C. After addition of 7-amino-cephalosporanic acid(3.26 g) and triethylamine (3 ml), the mixture was stirred for 2 hours at room temperature. Water (100 ml) was added to the reaction mixture. The mixture was adjusted pH to 1 with phosphoric acid, and extracted with a 3:1 (v/v) mixed solvent of ethyl acetate and tetrahydrofuran. The reaction mixture was dried, filtered, and concentrated. The residue was triturated with isopropyl ether, and the solid was filtered to give the above-indicated compound(3.05 g) in a clear brown solid.

NMR: δ (DMSO-$d_6$) 2.05(s, 3H), 3.2∼3.6(ABq, 2H), 3.95(s, 3H), 4.42∼5.45(ABq, 2H), 5.18(d, 1H), 5.80(q, 1H), 8.20(s, 2H).

PREPARATION 26

Preparation of 3-acethoxymethyl-7-[(Z)-2-(5-amino-1,2,4,-thiadiazol-3-yl)-2-(2-carboxyprop-2-oxyimino) acetamido]-3-cephem-4-carboxylic acid A. Preparation of 2-(ethoxyimino)malonitrile 2-(hydroxyimino)malononitrile (95 g) and diethylsulfate (230 ml) were reacted in the same method as described in (B) of Preparation 25 to give the above-indicated compound (97 g).

b.p.: 65°∼67° C./13 torr.

NMR: δ ($CDCl_3$) 1.20(t, 3H), 4.20(q, 2H).

B. Preparation of 2-cyano-2-(ethoxyimino)acetamidinium acetate 2-(ethoxyimino)malononitrile (15.9 g) was reacted in the same method as described in (C) of Preparation 25 to give the above-indicated compound (22.4 g).

NMR: δ (DMSO-$d_6$) 1.20(t, 3H), 1.90(s, 3H), 4.10(q, 2H), 7.90(s, 4H).

C. Preparation of 2-(5-amino-1,2,4-thiadiazol-3-yl)-2-(ethoxyimino) acetonitrile 2-cyano-2-(ethoxyimino)acetamidinium acetate (13.1 g) was reacted in the same method as described in (D) of Preparation 25 to give the above-indicated compound (12.1 g).

NMR: δ (DMSO-$d_6$) 1.37(t, 3H), 4.50 (q, 2H), 8.37 (s, 2H).

D. Preparation of 2-(5-amino-1,2,4-thiadiazol-3-yl)-2-(ethoxyimino) acetic acid 2-(5-amino-1,2,4-thiadiazol-3-yl)-2-(ethoxyimino)acetonitrile (12.1 g) was reacted in the same method as described in (E) of Preparation 25 to give the above-indicated compound (10.8 g).

NMR: δ (DMSO-$d_6$) 1.20(t, 3H), 4.20(q, 2H), 8.21(s, 2H).

E. Preparation of 3-acethoxymethyl-7-[(Z)-2-(5-amino-1,2,4-thiadiazol-3-yl)-2-(2-ethoxyimino)acetamido]-3-cephem-4-carboxylic acid 2-(5-amino-1,2,4-thiadiazol-3-yl)-2-(ethoxyimino)acetic acid (2.14 g) was reacted in the same method as described in (F) of Preparation 25 to give the above-indicated compound (3.31 g).

NMR: δ (DMSO-$d_6$) 1.25(t, 3H), 2.05(s, 3H), 3.40∼3.80(ABq, 2H), 4.22(q, 2H), 4.60∼5.48(q, 1H), 8.28(s, 2H)

Preparation 27: Preparation of 3-acethoxymethyl-7-[(Z)-2-(5-amino-1,2,4-thiadiazol-3-yl)-2-(2-carboxyprop-2-oxyimino) acetamido]-3-cephem-4-carboxylic acid A. Preparation of 2-(tert-buthoxycarbonylprop-2-oxyimino)malononitrile 2-(hydroxyimino)malononitrile (95 g) and tert-butyl-2-bromo-2-methyl propionate (240 g) were reacted in the same method as described in (B) of Preparation 25 to give the above-indicated compound (176 g).

b.p.: 115°∼120° C./13 torr.

NNR: δ ($CDCl_3$) 1.48(s, 9H), 1.63(s, 6H).

B. Preparation of 2-(tert-butoxycarbonylprop-2-oxyimino)-2-cyanoacetamidinium acetate To ammonium acetate (18.5 g) dissolved in methanol (100 ml) was added 2-(tert-butoxycarbonylprop-2-oxyimino)malononitrile (19 g). After stirred for 2 hours, the mixture was standed overnight at room temperature. The reaction mixture was concentrated, and water (500 ml) was added therein. The obtained mixture was extracted with ethylacetate (500 ml). After the extract was dehydrated, filtered, and concentrated, ethylether was added therein, and stirred for 30 minutes. The precipitates were filtered to give the above-indicated compound (15 g) in pale yellow.

NMR: δ (DMSO-$d_6$) 1.40(s, 9H), 1.60(s, 6H), 1.98(s, 3H), 7.38(bs, 3H).

C. Preparation of 2-(5-amino-1,2,4-thiadiazol-3-yl)-2-(tertbutoxycarbonylprop-2-oxyimino)acetonitrile 2-(tert-butoxycarbonylprop-2-oxyimino)-2-cyanoacetamdinium acetate (24.1 g) was reacted in the same method as described in (D) of Preparation 25 to give the above-indicated compound (13.7 g).

NMR: δ (DMSO-$d_6$) 1.40(s,9H), 1.58(s, 6H), 8.43(s, 2H).

D. Preparation of 2-(5-amino-1,2,4,-thiadiazol-3-yl)-2-(2-carboxyprop-2-oxyimino)acetic acid 2-(5-amino-1,2,4-thiadiazol-3-yl)-2-(2-butoxycarbonylprop-2-oxyimino)acetonitrile (13.7 g) was reacted in the same method as described in (E) of Preparation 25 to give the above-indicated compound (10.1 g).

NMR: δ (DMSO-$d_6$) 1.42(s, 6H), 8.22(s, 2H).

E. Preparation of 3-acethoxymethyl-7-[(Z)-2-(5-amino-1,2,4-thiadiazol-3-yl)-2-(2-carboxyprop-2-oxyimino)acetamido]-3-cephem-4-carboxylic acid 2-(5-amino-1,2,4-thiadiazol-3-yl)-2-(2-carboxyprop-2-oxyimino) acetic acid (2.93 g) was reacted in the same method as described in (F) of Preparation 25 to give the above-indicated compound (3.42 g).

NMR: δ ($D_2O+NaHCO_3$) 1.58(s, 6H), 2.05(s, 3H), 3.10∼3.72(ABq, 2H), 4.60∼4.95 (ABq, 2H), 5.14(d, 1H), 5.70(d, 1H).

EXAMPLE 1

Synthesis of 7-[(Z)-2-(2-aminothiazol-4-yl)-2-(methoxyimino) acetamido]-3-(4,6-diamino-1-methylpyrimidinium-2-yl)thiomethyl-3-cephem-4-carboxylate To a solution of 3-acetoxymethyl-7-[(Z)-2-(2-aminothiazol-4-yl)2-methoxyimino) acetamido]-3-cephem-4-carboxylic acid(500 mg) suspended in distilled water(5 ml) were added 4,6-diamino-1-methyl-2(1H)-pyrimidinethione (200 mg) and potassium iodide(800 mg). While adjusting pH of the mixture to 7.1~7.2 with a sodium bicarbonate solution, the reaction mixture was heated to 70° C. After stirred for 4 hours, the mixture was cooled to room temperature. The pH was adjusted to 3~3.5 with 2N hydrochloric acid, and the precipitates were filtered, washed with distilled water(5 ml), and chromatographed over silica gel. Elution with a 5:1 (v/v) mixture of acetonitrile/distilled water gave the above-indicated compound (320 mg) in a pale white solid.

m.p.: 157° C.~(decomp.)

NMR: δ ($D_2O+NaHCO_3$) 3.54 (s, 3H), 3.61 (ABq, 2H), 3.98 (s, 3H), 5.17 (d, 1H), 5.65 (s, 1H), 5.78 (d, 1H), 7.03 (s, 1H).

MS(FAB, M+1): 552.

IR(KBr, $cm^{-1}$): 1765 (β-lactam), 1660, 1630, 1550.

EXAMPLE 2

Synthesis of 7-[(Z)-2-(2-aminothiazol-4-yl)-2-(ethoxyimino) acetamido]-3-(4,6-diamino-1-methyl-pyrimidinium-2-yl)thiomethyl-3-cephem-4-carboxylate 3-Acetoxymethyl-7-[(Z)-2-(2-aminothiazol-4-yl)-2-(ethoxyimino) acetamido]-3-cephem-4-carboxylic acid (500 mg) was reacted in the same manner as described in Example 1 to give the above-indicated compound (310 mg) in a white solid.

m.p.: 163° C.~(decomp.)

NMR: δ ($D_2O+NaHCO_3$) 1.09 (t, 3H), 3.48 (s, 3H), 3.56 (ABq, 2H), 4.14 (q, 2H), 5.11 (d, 1H), 5.56 (s, 1H), 5.78 (d, 1H), 6.94 (s, 1H).

MS(FAB, M+1): 566

IR(KBr, $cm^{-1}$): 1760 (β-lactam), 1660, 1590.

EXAMPLE 3

Synthesis of 7-[(Z)-2-(2-aminothiazol-4-yl)-2-(ethoxyimino) acetamido]-3-(4,6-diamino-1-ethylpyrimidinium-2-yl)thiomethyl-3-cephem-4-carboxylate To a solution of 3-acetoxymethyl-7-[(Z)-2-(2-aminothiazol-4-yl)-2-(ethoxyimino)acetamido]-3-cephem-4-carboxylic acid (500 mg) suspended in distilled water (5 ml) were added 4,6-diamino-1-ethyl-2(1H)-pyrimidinethione (200 mg) and potassium iodide (1 g). With adjusting pH of the mixture to pH 7.1~7.2 with a sodium bicarbonate solution, the reaction mixture was heated to 70° C. After stirred for 5 hours, the mixture was cooled to room temperature. The pH was adjusted to 3~3.5 with 2N hydrochloric acid, and the precipitates were filtered, washed with distilled water (5 ml), and chromatographed over silica gel. Elution with a 5:1 (v/v) mixture of acetonitrile/distilled water gave the above-indicated compound(290 mg) in a pale white solid.

m.p.: 161° C.~(decomp.)

NMR: δ($D_2O+NaHCO_3$) 1.31 (m, 6H), 3.60 (ABq, 2H), 4.19 (m, 4H), 4.43 (ABq, 2H), 5.19 (d, 1H), 5.66 (s, 1H), 5.84 (d, 1H), 6.92 (s, 1H).

MS(FAB, M+1): 580.

IR(KBr, $cm^{-1}$): 1768 (β-lactam), 1680, 1620, 1560.

EXAMPLE 4

Synthesis of 3-(1-allyl-4,6-diaminopyrimidinium-2-yl)thiomethyl-7-[(Z)-2-(2-aminothiazol-4-yl)-2-(ethoxyimino)acetamido]-3-cephem-4-carboxylate To a solution of 3-acetoxymethyl-7-[(Z)-2-(2-aminothiazol-4-yl)-2-(ethoxyimino)acetamido]-3-cephem-4-carboxylic acid (500 mg) suspended in distilled water (5 ml) were added 1-allyl-4,6-diamino-2(1H)-pyrimidinethione (200 mg) and potassium iodide (1 g). The pH of the mixture was adjusted to 7.1~7.2 with a sodium carbonate solution, and acetonitrile (1 ml) was added thereto. After stirring for 4 hours at 75° C., the mixture was cooled to room temperature. The pH was adjusted to 3~3.5 with 2N hydrochloric acid, and the precipitates were filtered, washed with distilled water (5 ml), and chromatographed over silica gel. Elution with a 5:1 (v/v) mixture of acetonitrile/distilled water gave the above-indicated compound(300 mg) in a white solid.

m.p.: 165° C.~(decomp.).

NMR: δ($D_2O+NaHCO_3$) 1.29 (t, 3H), 3.57 (ABq, 2H), 4.17 (q, 2H), 5.16 (d, 1H), 5.66 (s, 1H), 5.82 (d, 1H), 5.09~6.56 (m, 5H), 6.96 (s, 1H).

MS(FAB, M+1): 592.

IR(KBr, $cm^{-1}$): 1765 (β-lactam), 1680, 1630, 1550.

EXAMPLE 5

Synthesis of 7-[(Z)-2-(2-aminothiazol-4-yl)-2-(2-propen-1-oxyimino)acetamido]-3-(4,6-diamino-1-methylpyrimidinium-2-yl)thiomethyl-3-cephem-4-carboxylate A solution of 3-acetoxymethyl-7-[(Z)-2-(2-aminothiazol-4-yl)-2-(2-propen-1-oxyimino)acetamido]-3-cephem-4-carboxylic acid (500 mg) suspended in distilled water (5 ml) was reacted in the same manner as described in Example 1 to give the above-indicated compound (260 mg) in a pale white solid.

m.p.: 169° C.~(decomp.).

NMR: δ($D_2O$+acetone-$d_6$) 3.60 (ABq, 2H), 3.61 (s, 3H), 4.40 (ABq, 2H), 5.16 (d, 1H), 5.68 (s, 1H), 5.84 (d, 1H), 5.11~6.25 (m, 5H), 6.96 (s, 1H).

MS(FAB, M+1): 578.

IR(KBr, $cm^{-1}$): 1760 (β-lactam), 1670, 1618, 1522.

EXAMPLE 6

Synthesis of 7-[(Z)-2-(2-aminothiazol-4-yl)-2-(2-propen-1-oximino)acetamido]-3-(4,6-diamino-1-ethylpyrimidinium-2-yl)thiomethyl-3-cephem-4-carboxylate 3-Acetoxymethyl-7-[(Z)-2-(2-aminothiazol-4-yl)-2-(2-propen-1-oxyimino) acetamido]-3-cephem-4-carboxylic acid (500 mg) and 4,6-diamino-1-ethyl-2(1H)-pyrimidinethione (200 mg) were reacted in the same manner as described in Example 1 to give the above-indicated compound (290 mg).

m.p.: 165° C.~(decomp.).

NMR: δ ($D_2O$+acetone-$d_6$) 1.41 (t, 3H), 3.57 (ABq, 2H), 4.14 (q, 2H), 4.41 (ABq, 2H), 5.16 (d, 1H), 5.67 (s, 1H), 5.84 (d, 1H), 5.05~6.12 (m, 5H), 6.96 (s, 1H).

MS(FAB, M+1): 592.

IR(KBr, $cm^{-1}$): 1764 ($\beta$-lactam), 1765, 1615, 1522.

EXAMPLE 7

Synthesis of 3-(1-allyl-4,6-diaminopyrimidinium-2-yl)thiomethyl-7-[(Z)-2-(2-aminothiazol-4-yl)-2-(propen-1-oxyimino)acetamido]-3-cephem-4-carboxylate 3-Acetoxymethyl-7-[(Z)-2-(2-aminothiazol-4-yl)-2-(2-propene-1-oxyimino)acetamido]-3-cephem-4-carboxylic acid (500 mg) and 1-allyl-4,6-diamino-2(1H)-pyrimidinethione (200 mg) were reacted in the same manner as described in Example 1 to give the above-indicated compound (310 mg).

NMR: $\delta$ ($D_2O$+acetone-$d_6$) 3.56 (ABq, 2H), 4.39 (ABq, 2H), 5.16 (d, 1H), 5.62 (s, 1H), 5.79 (d, 1H), 5.08~6.21 (m, 10H), 7.01 (s, 1H).

MS(FAB, M+1): 604.

IR(KBr, $cm^{-1}$): 1770 ($\beta$-lactam), 1669, 1620, 1531.

EXAMPLE 8

Synthesis of 7-[(Z)-2-(2-aminothiazol-4-yl)-2-(2-propyn-1-oxyimino)acetamido]-3-(4,6-diamino-1-methyl-pyrimidinium-2-yl)thiomethyl-3-cephem-4-carboxylate To a solution of 3-acetoxymethyl-7-[(Z)-2-(2-aminothiazol-4-yl)-2-(2-propyn-1-oxyimino)acetamido]-3-cephem-4-carboxylic acid (500 mg) suspended in distilled water (5 ml) were added 4,6-diamino-1-methyl-2(1H)-pyrimidinethione (200 mg) and potassium iodide (1 g). While adjusting pH of the mixture to 7.1~7.2 with a sodium bicarbonate solution, the reaction mixture was heated to 70° C. After stirring for 4 hours, the mixture was cooled to room temperature. The pH was adjusted to 3~3.5 with 2N hydrochloric acid, and the precipitates were filtered, washed with distilled water (5 ml), and chromatographed over silica gel. Elution with a 5:1 (v/v) mixture of acetonitrile/distilled water gave the above-indicated compound (300 mg) in a pale white solid.

m.p.: 167° C.~(decomp.).

NMR: $\delta$ ($D_2O$+acetone-$d_6$) 3.01 (s, 1H), 3.56 (s, 3H), 3.62 (ABq, 2H), 4.76 (s, 2H), 5.12 (d, 1H), 5.65 (s, 1H), 5.79 (d, 1H), 6.96 (s, 1H).

MS(FAB, M+1): 576.

IR(KBr, $cm^{-1}$): 1766 ($\beta$-lactam), 1685, 1632, 1525.

EXAMPLE 9

Synthesis of 7-[(Z)-2-(2-aminothiazol-4-yl)-2-(2-propyn-1-oxyimino)acetamido]-3-(4,6-diamino-1-ethylpyrimidinium-2-yl)thiomethyl-3-cephem-4-carboxylate 3-Acetoxymethyl-7-[(Z)-2-(2-aminothiazol-4-yl)-2-(2-propyn-1-oxyimino)acetamido]-3-cephem-4-carboxylic acid (500 mg) and 4,6-diamino-1-ethyl-2(1H)-pyrimidinethione(200 mg) were reacted in the same manner as described in Example 1 to give the above-indicated compound (280 mg).

m.p.: 165° C.~(decomp.).

NMR: $\delta$ ($D_2O$+acetone-$d_6$) 1.41 (t, 3H), 3.03 (s, 1H), 3.56 (ABq, 2H), 4.16 (q, 2H), 4.39 (ABq, 2H), 4.81 (s, 2H), 5.16 (d, 1H), 5.66 (s, 1H), 5.84 (d, 1H), 7.00 (s, 1H).

MS(FAB, M+1): 590.

IR(KBr, $cm^{-1}$): 1769 ($\beta$-lactam), 1781, 1630, 1525.

EXAMPLE 10

Synthesis of 3-(1-allyl-4,6-diaminopyrimidinium-2-yl)thiomethyl-7-[(Z)-2-(2-aminothiazol-4-yl)-2-(2-propyn-1-oxyimino)acetamido]-3-cephem-4-carboxylate 3-Acetoxymethyl-7-[(Z)-2-(2-aminothiazol-4-yl)-2-(2-propyn-1-oxyimino)acetamido]-3-cephem-4-carboxylic acid (500 mg) and 1-allyl-4,6-diamino-2(1H)-pyrimidinethione (200 mg) were reacted in the same manner as described in Example 1 to give the above-indicated compound (270 mg).

m.p.: 171° C.~(decomp.).

NMR: $\delta$ ($D_2O$+acetone-$d_6$) 3.02 (s, 1H), 3.57 (ABq, 2H), 4.43 (ABq, 2H), 4.79 (s, 2H), 5.18 (d, 1H), 5.63 (s, 1H), 5.79 (d, 1H), 5.12~6.31 (m, 5H), 6.97 (s, 1H).

MS(FAB. M+1):602.

IR(KBr. $cm^{-1}$):1765 ($\beta$-lactam), 1660, 1620, 1530.

EXAMPLE 11

Synthesis of 7-[(Z)-2-(2-aminothiazol-4-yl)-2-(2-carboxyprop-2-oxyimino)acetamido]-3-(4,6-diamino-1-methyl-pyrimidinium-2-yl) thiomethyl-3-cephem-4-carboxylate To a solution of 3-acetoxymethyl-7-[(Z)-2-(2-aminothiazol-4-yl)-2-(carboxyprop-2-oxyimino)acetamido]-3-cephem-4-carboxylic acid (500 mg) suspended in distilled water (5 ml) were added 4,6-diamino-1-methyl-2(1H)-pyrimidinethione (200 mg) and potassium iodide (1.2 g). While adjusting pH of the mixture to 7.3~7.5 with a sodium bicarbonate solution, the reaction mixture was heated to 70° C. After stirring for 4 hours, the mixture was cooled to room temperature. Insoluble materials were removed by filtration, and the pH of the filtrate was adjusted to 4 with 2N-hydrochloric acid. The precipitates were filtered, washed with distilled water (5 ml), and chromatographed over silica gel. Elution with a 5:1 (v/v) mixture of acetonitrile/distilled water gave the above-indicated compound (280 mg) in a pale white solid.

m.p.: 151° C.~(decomp.).

NMR: $\delta$ ($D_2O$+$NaHCO_3$) 1.50 (s, 6H), 3.50 (s, 3H), 3.59 (ABq, 2H), 4.29 (ABq, 2H), 5.17 (d, 1H), 5.58 (s, 1H), 5.79 (d, 1H), 6.95 (s, 1H).

MS(FAB. M+1):624.

IR(KBr. $cm^{-1}$): 1761 ($\beta$-lactam), 1660, 1580, 1550.

EXAMPLE 12

Synthesis of 7-[(Z)-2-(2-aminothiazol-4-yl)-2-(2-carboxyprop-2-oxyimino)acetamido]-3-(4,6-diamino-1-ethylpyrimidinium-2-yl)thiomethyl-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid dihydrochloride (500 mg) and 4,6-diamino-1-ethyl-2(1H)-pyrimidinethione (200 mg) were reacted in the same manner as described in Example 11 to give the above-indicated compound (310 mg) in a pale white solid.

m.p.: 153° C.~(decomp.)

NMR: $\delta$ ($D_2O$+$NaHCO_3$) 1.32 (t, 3H), 1.48 (s, 6H), 3.56 (ABq, 2H), 4.04 (q, 2H), 4.31 (ABq, 2H), 5.12 (d, 1H), 5.53 (s, 1H), 5.73 (d, 1H), 6.92 (s, 1H).

MS(FAB, M+1): 638

IR(KBr. $cm^{-1}$): 1770 ($\beta$-lactam), 1680, 1590, 1530.

EXAMPLE 13

Synthesis of 7-[(Z)-2-(2-aminothiazol-4-yl)-2-(2-carboxyprop-2-oxyimino)acetamido]-3-(4,6-diamino-1-propyl-pyrimidinium-2-yl)thiomethyl-3-cephem-4-carboxylate To a solution of 3-acetoxymethyl-7-[(Z)-2-(2-aminothiazol-4-yl)-2-(2-carboxyprop-2-oxyimino)acetamido]-3-cephem-4-carboxylic acid dihydrochloride (500 mg) dissolved in distilled water (10 ml) were added 4,6-diamino-1-propyl-2(1H)-pyrimidinethione (200 mg) and potassium iodide (1.2 g). The pH of the mixture was adjusted to 7.3~7.4 with a sodium bicarbonate solution, and acetonitrile (3 ml) was added thereto. After stirring for 5 hours at 73° C., the mixture was cooled to room temperature and, the acetonitrile was removed under reduced pressure. Insoluble materials were filtered off, and pH of the filtrate was adjusted to 4.5 with 2N-hydrochloric acid. After being concentrated under reduced pressure, the residue was chromatographed over silica gel. Elution with a 5:1(v/v) mixture of acetonitrile/distilled water gave the above-indicated compound (210 mg) in a pale yellow solid.

m.p.: 156° C.~(decomp.).

NMR: δ ($D_2O$+$NaHCO_3$) 0.93 (t, 3H), 1.49 (s, 6H), 1.77 (m, 2H), 3.61 (ABq, 2H), 3.91 (t, 2H), 5.14 (d, 1H), 5.54 (s, 1H), 5.77 (d, 1H), 6.92 (s, 1H).

MS(FAB. M+1): 652

IR(KBr. $cm^{-1}$): 1765 (β-lactam), 1650, 1596, 1530.

EXAMPLE 14

Synthesis of 7-[(Z)-2-(2-aminothiazol-4-yl)-2-(2-carboxyprop-2-oxyimino)acetamido]-3-(1-butyl-4,6-diaminopyrimidinium-2-yl)thiomethyl-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid dihydrochloride (500 mg) and 1-butyl-4,6-diamino-1-2(H)-pyrimidinethione (200 mg) were reacted in the same manner as described in Example 13 to give the above indicated-compound (230 mg).

m.p.: 161° C.~(decomp.).

NMR: δ ($D_2O$+acetone-$d_6$) 0.92 (t, 3H), 1.36 (m, 2H), 1.48 (s, 6H), 1.71 (m, 2H), 3.52 (ABq, 2H), 3.99 (t, 2H), 4.35 (ABq, 2H), 5.14 (d, 1H), 5.58 (s, 1H), 5.79 (d, 1H), 6.95 (s, 1H).

MS(FAB. M+1): 666

IR(KBr. $cm^{-1}$): 1768 (β-lactam), 1671, 1625, 1528.

EXAMPLE 15

Synthesis of 3-(1-allyl-4,6-diaminopyrimidinium-2-yl)thiomethyl-7-[(Z)-2-(2-aminothiazol-4-yl)-2-(2-carboxyprop-2-oxyimino) acetamido]-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid dihydrochloride (500 mg) and 1-allyl-4,6-diamino-2(1H)-pyrimidinethione (200 mg) were reacted in the same manner as described in Example 13 to give the above-indicated compound (310 mg).

m.p.: 160° C.~(decomp.).

NMR: δ($D_2O$+acetone-$d_6$) 1.48 (s, 6H), 3.56 (ABq, 2H), 5.16 (d, 1H), 5.61 (s, 1H), 5.79 (d, 1H), 5.05~6.51 (m, 5H), 6.96 (s, 1H).

MS(FAB, M+1): 650

IR(KBr, $cm^{-1}$): 1765 (β-lactam), 1670, 1620, 1530.

EXAMPLE 16

Synthesis of 7-[(Z)-2-(2-aminothiazol-4-yl)-2-(1-carboxyeth-1-oxyimino)acetamido]-3-(4,6-diamino-1-methyl-pyrimidinium-2-yl)thiomethyl-3-cephem-4-carboxylate To a solution of 3-acetoxymethyl-7-[(Z)-2-(2-aminothiazol-4-yl)-2-(1-carboxyeth-1-oxyimino)acetamido]-3-cephem-4-carboxylic acid (500 mg) suspended in distilled water (10 ml) were added 4,6-diamino-1-methyl-2(1H)-pyrimidinethione (200 mg) and potassium iodide (1.2 g). While adjusting pH of the mixture to 7.1~7.2 with a sodium bicarbonate solution, the reaction mixture was heated to 70° C. After stirring for 5 hours, the mixture was cooled to room temperature. The pH was adjusted to 4.1 with 2N-hydrochloric acid, and the precipitates were filtered, washed with distilled water (5 ml, and chromatographed over silica gel. Elution with a 5:1 (v/v) mixture of acetonitrile/distilled water gave the above-indicated compound (200 mg) in a pale white solid.

m.p.: 153° C.~(decomp.)

NMR: δ($D_2O$+$NaHCO_3$) 1.48 (d, 3H), 3.53 (s, 3H), 3.59 (ABq, 2H), 4.36 (ABq, 2H), 5.17 (d, 1H), 5.60 (s, 1H), 5.79 (d, 1H), 7.01 (s, 1H).

MS(FAB, M+1): 610

IR(KBr, $cm^{-1}$): 1766 (β-lactam), 1765, 1595, 1525.

EXAMPLE 17

Synthesis of 7-[(Z)-2-(2-aminothiazol-4-yl)-2-(2-carboxyeth-1-oxyimino)acetamido]-3-(1-ethyl-4,6-diaminopyrimidinium-2-yl)thiomethyl-3-cephem-4-carboxylate 3-Acetoxymethyl-7-[(Z)-2-(2-aminothiazol-4-yl)-2-(1-carboxyeth-1-oxyimino)acetamido]-3-cephem-4-carboxylic acid (500 mg) and 4,6-diamino-1-ethyl-2(1H)-pyrimidinethione (200 mg) were reacted in the same manner as described in Example 16 to give the above-indicated compound(210 mg).

m.p.: 155° C.~(decomp.)

NMR: δ ($D_2O$+acetone-$d_6$) 1.34 (t, 3H), 1.48 (d, 3H), 3.59 (ABq, 2H), 4.04 (q, 2H), 5.15 (d, 1H), 5.52 (s, 1H), 5.78 (d, 1H), 6.96 (s, 1H).

MS(FAB. M+1): 624.

IR(KBr. $cm^{-1}$): 1765 (β-lactam), 1765, 1590, 1530.

EXAMPLE 18

Synthesis of 7-[(Z)-2-(2-aminothiazol-4-yl)-2-(1-carboxyeth-1-oxyimino)acetamido]-3-(4,6-diamino-1-propyl-pyrimidinium-2-yl)thiomethyl-3-cephem-4-carboxylate 3-Acetoxymethyl-7-[(Z)-2-(2-aminothiazol-4-yl)-2-(1-carboxyeth-1-oxyimino)acetamido]-3-cephem-4-carboxylic acid (500 mg) and 4,6-diamino-1-propyl-2(1H)-pyrimidinethione (200 mg) were reacted in the same manner as described in Example 16 to give the above-indicated compound (170 mg).

m.p.: 154° C.~(decomp.)

NMR: δ ($D_2O$+$NaHCO_3$) 0.95 (t, 3H), 1.46 (d, 3H), 1.65 (m, 2H), 3.56 (ABq, 2H), 3.91 (t, 2H), 5.17 (d, 1H), 5.56 (s, 1H), 5.77 (d, 1H), 6.96 (s, 1H).

MS(FAB. M+1): 638.

IR(KBr. $cm^{-1}$): 1760 (β-lactam), 1671, 1590, 1525.

EXAMPLE 19

Synthesis of 3-(1-allyl-4,6-diaminopyrimidinium-2-yl)thiomethyl-7-[(Z)-2-(2-aminothiazol-4-yl)-2-(1-carboxyeth-1-oxyimino) acetamido]-3-cephem-4-carboxylate 3-Acetoxymethyl-7-[(Z)-2-(2-aminothiazol-4-yl)-2-(1-carboxyeth-1-oxyimino)acetamido]-3-cephem-4-carboxylic acid (500 mg) and 1-allyl-4,6-diamino-2(1H)-pyrimidinethione (200 mg) were reacted in the same manner as described in Example 16 to give the above-indicated compound(230 mg).

m.p.: 155° C.~(decomp.)

NMR: δ ($D_2O$+acetone-$d_6$) 1.44 (d, 3H), 3.52 (ABq, 2H), 5.16 (d, 1H), 5.59 (s, 1H), 5.76 (d, 1H), 5.07~6.51 (m, 5H), 6.99 (s, 1H).

MS(FAB, M+1): 636.

IR(KBr, $cm^{-1}$): 1765 (β-lactam), 1680, 1600, 1530.

EXAMPLE 20

Synthesis of 7-[(Z)-2-(2-aminothiazol-4-yl)-2-(-carboxymethoxyimino)acetamido]-3-(4,6-diamino-1-methylpyrimidinium-2-yl) thiomethyl-3-cephem-4-carboxylate To a solution of 3-acetoxymethyl-7-[(Z)-2-(2-aminothiazol-4-yl)-2-(-carboxymethoxyimino)acetamido]-3-cephem-4-carboxylic acid (500 mg) suspended in distilled water (10 ml) were added 4,6-diamino-1-methyl-2(1H)-pyrimidinethione (200 mg) and potassium iodide (1.2 g). With the adjusting of the pH of the mixture to 7.2 with a sodium bicarbonate solution, the reaction mixture was stirred for 5 hours at 70° C. After cooled to room temperature, insoluble materials were filtered off, and the pH of the filtrate was adjusted to 4.1 with 2N-hydrochloric acid. After being concentrated under reduced pressure, the residue was chromatographed over silica gel. Elution with a 4:1 (v/v) mixture of acetonitrile/distilled water gave above-indicated compound(350 mg) in a white solid.

m.p.: 167° C.~(decomp.).

NMR: δ ($D_2O+NaHCO_3$) 3.49 (s, 3H), 3.52 (ABq, 2H), 4.34 (ABq, 2H), 4.60 (s, 2H), 5.16 (d, 1H), 5.56 (s, 1H), 5.78 (d, 1H), 6.98 (s, 1H).

MS(FAB, M+1): 596.

IR(KBr, $cm^{-1}$): 1760 (β-lactam), 1670, 1600, 1550.

EXAMPLE 21

Synthesis of 7-[(Z)-2-(2-aminothiazol-4-yl)-2-(carboxymethoxyimino)acetamido]-3-(4,6-diamino-1-ethylpyrimidinium-2-yl)thiomethyl-3-cephem-4-carboxylate 3-Acetoxymethyl-7-[(Z)-2-(2-aminothiazol-4-yl)-2-(-carboxymethoxyimino) acetamido]-3-cephem-4-carboxylic acid (500 mg) and 4,6-diamino-1-ethyl-2(1H)-pyrimidinethione (200 mg) were reacted in the same manner as described in Example 20 to give the above-indicated compound(280 mg).

m.p.: 165° C.~(decomp.).

NMR: δ ($D_2O$+$NAHCO_3$) 1.32 (t, 3H), 3.62 (ABq, 2H), 3.98 (q, 2H), 4.60 (s, 2H), 5.17 (d, 1H), 5.58 (s, 1H), 5.80 (d, 1H), 7.01 (s, 1H).

MS(FAB, M+1): 610.

IR(KBr, $cm^{-1}$): 1765 (β-lactam), 1670, 1600, 1520.

EXAMPLE 22

Synthesis of 7-[(Z)-2-(2-aminothiazol-4-yl)-2-(carboxymethoxyimino)acetamido]-3-(4,6-diamino-1-propylpyrimidinium-2-yl)thiomethyl-3-cephem-4-carboxylate 3-Acetoxymethyl-7-[(Z)-2-(2-aminothiazol-4-yl)-2-(-carboxymethoxyimino)acetamido]-3-cephem-4-carboxylic acid (500 mg) and 4,6-diamino-1-propyl-2(1H)-pyrimidinethione (200 mg) were reacted in the same manner as described in Example 20 to give the above-indicated compound(210 mg).

m.p.: 169° C.~(decomp.),

NMR: δ ($D_2O+NaHCO_3$)

0.93 (t, 3H), 1.73 (m, 2H), 3.56 (ABq, 2H), 3.92 (t, 2H), 4.58 (s, 2H), 5.15 (d, 1H), 5.56 (s, 1H), 5.78 (d, 1H), 6.98 (s, 1H).

MS(FAB. M+1): 624.

IR(KBr. $cm^{-1}$): 1763 (β-lactam), 1670, 1610, 1525.

EXAMPLE 23

Synthesis of 7-[(Z)-2-(2-aminothiazol-4-yl)-2-(carboxymethoxyimino)acetamido]-3-(1-butyl-4,6-diaminopyrimidinium-2-yl)thiomethyl-3-cephem-4-carboxylate 3-Acetoxymethyl-7-[(Z)-2-(2-aminothiazol-4-yl)-2-(-carboxymethoxyimino)acetamido]-3-cephem-4-carboxylic acid (500 mg) and 1-butyl-4,6-diamino-2(1H)-pyrimidinethione (200 mg) were reacted in the same manner as described in Example 20 to give the above-indicated compound(240 mg).

m.p.: 167° C.~(decomp.).

NMR: δ ($D_2O+NaHCO_3$)

0.92 (t, 3H), 1.32 (m, 2H), 1.66 (m, 2H), 3.60 (ABq, 2H), 3.96 (t, 2H), 4.57 (s, 2H), 5.15 (d, 1H), 5.58 (s, 1H), 5.78 (d, 1H), 7.01 (s, 1H).

MS(FAB. M+1): 638

IR(KBr. $cm^{-1}$): 1765 (β-lactam), 1670, 1610, 1530.

EXAMPLE 24

Synthesis of 3-(1-allyl-4,6-diaminopyrimidinium-2-yl)thiomethyl-7-[(Z)-2-(2-aminothiazol-4-yl)-2-(-carboxymethoxyimino)acetamido]-3-cephem-4-carboxylate 3-Acetoxymethyl-7-[(Z)-2-(2-aminothiazol-4-yl)-2-(-carboxymethoxyimino)acetamido]-3-cephem-4-carboxylic acid (500 mg) and 1-allyl-4,6-diamino-2(1H)-pyrimidinethione (200 mg) were reacted in the same manner as described in Example 20 to give the above-indicated compound(220 mg).

m.p.: 165° C.~(decomp.).

NMR: δ ($D_2O+NaHCO_3$)

3.56 (ABq, 2H), 4.56 (s, 2H), 5.12 (d, 1H), 5.63 (s, 1H), 5.79 (d, 1H), 5.07~6.51 (m, 5H), 7.00 (s, 1H).

MS(FAB, M+1): 622.

IR(KBr, $cm^{-1}$): 1770 (β-lactam), 1660, 1600, 1535.

EXAMPLE 25

Synthesis of 7-[(Z)-2-(2-aminothiazol-4-yl)-2-(methoxyimino) acetamido]-3-(1,4,6-triaminopyrimidinium-2-yl)thiomethyl-3-cephem-4-carboxylate To a solution of 3-acetoxymethyl-7-[(Z)-2-(2-aminothiazol-4-yl)-2-(methoxyimino)acetamido]-3-cephem-4-carboxylic acid (500 mg) suspended in distilled water (5 ml) were added 1,4,6-triamino-2(1H)-pyrimidinethione (200 mg) and potassium iodide (800 mg). With adjusting of the pH of the mixture to 7.1~7.2 with a sodium bicarbonate solution, the reaction mixture was heated to 70° C. After stirring for 4 hours, the mixture was cooled to room temperature. The pH was adjusted to 3~3.5 with 2N-hydrochloric acid, and the precipitates were filtered, washed with distilled water (5 ml), and chromatographed over silica gel. Elution with a 5:1(v/v) mixture of acetonitrile/distilled water gave the above-indicated compound (300 mg) in a pale white solid.

m.p.: 156° C.~(decomp.).

NMR: δ($D_2O$+acetone-$d_6$) 3.58 (ABq, 2H), 3.81 (s, 3H), 4.33 (ABq, 2H), 5.12 (d, 1H), 5.61 (s, 1H), 5.83 (d, 1H), 6.91 (s, 1H).

MS(FAB, M+1): 553.

IR(KBr, $cm^{-1}$): 1765 (β-lactam), 1670, 1620, 1560.

EXAMPLE 26

Synthesis of 7-[(Z)-2-(2-aminothiazol-4-yl)-2-(ethoxyimino) acetamido]-3-(1,4,6-triaminopyrimidinium-2-yl)thiomethyl-3-cephem-4-carboxylate 3-Acetoxymethyl-7-[(Z)-2-(2-aminothiazol-4-yl)-2-(ethoxyimino)acetamido]-3-cephem-4-carboxylic acid (500 mg) was reacted in the same manner as described in Example 25 to give the above-indicated compound (290 mg) in a pale white solid.

m.p.: 165° C.~(decomp.).

NMR: δ($D_2O$+acetone-$d_6$) 1.29 (t, 2H), 3.57 (ABq, 2H), 4.24 (q, 2H), 4.35 (ABq, 2H), 5.16 (d, 1H), 5.62 (s, 1H), 6.91 (s, 1H).

MS(FAB, M+1): 567.

IR(KBr, $cm^{-1}$): 1765 (δ-lactam), 1680, 1590.

EXAMPLE 27

Synthesis of 7-[(Z)-2-(2-aminothiazol-4-yl)-2-(2-propyn-1-oxyimino)acetamido[-3-(1,4,6-triaminopyrimidinium-2-yl) thiomethyl-3-cephem-4-carboxylate 3-Acetoxymethyl-7-[(Z)-2-(2-aminothiazol-4-yl)-2-(2-propyn-1-oxyimino) acetamido]-3-cephem-4-carboxylic acid (500 mg) was reacted in the same manner as described in Example 25 to give the above-indicated compound (350 mg) in a pale yellow solid.

m.p.: 167° C.~(decomp.).

NMR: δ ($D_2O$+acetone-$d_6$) 3.06 (t, 1H), 3.56 (ABq, 2H), 4.41 (ABq, 2H), 4.80 (d, 2H), 5.12 (d, 1H), 5.62 (s, 1H), 5.80 (d, 1H), 6.96 (s, 1H).

MS(FAB, M+1): 577.

IR(KBr. $cm^{-1}$): 1765 (β-lactam), 1690, 1580.

EXAMPLE 28

Synthesis of 7-[(Z)-2-(5-amino-1,2,4-thiadiazol-3-yl)-2-(ethoxyimino)acetamido]-3-(1,4,6-triaminopyrimidinium-2-yl) thiomethyl-3-cephem-4-carboxylate 3-Acetoxymethyl-7-[(Z)-2-(5-amino-1,2,4-thiadiazol-3-yl)-2-(ethoxyimino)acetamido]-3-cephem-4-carboxylic acid (500 mg) was reacted in the same manner as described in Example 25 to give the above-indicated compound (280 mg) in a yellow solid.

m.p.: 169° C.~(decomp.).

NMR: δ ($D_2O$+acetone-$d_6$) 1.52 (t, 3H), 3.57 (ABq, 2H), 4.26 (ABq, 2H), 4.36 (q, 2H), 5.14 (d, 1H), 5.58 (s, 1H), 5.84 (d, 1H).

IR(KBr. $cm^{-1}$): 1769 (β-lactam), 1690, 1630.

EXAMPLE 29

Synthesis of 7-[(Z)-2-(2-aminothiazol-4-yl)-2-(2-carboxyprop-2-oxyimino)acetamido]-3-(1,4,6-triaminopyrimidinium-2-yl) thiomethyl-3-cephem-4-carboxylate To a solution of 3-acetoxymethyl-7-[(Z)-(2-amino-thiazol-4-yl)-2-(2-carboxyprop-2-oxyimino)acetamido]-3-cephem-4-carboxylic acid (500 mg) suspended in distilled water (10 ml) were added 1,4,6-triamino-2-(1H)-pyrimidinethione (200 mg) and potassium iodide (1.2 g). The pH of the reaction mixture was adjusted to 7.1~7.3 with a sodium bicarbonate solution, and the reaction mixture was heated for 4 hours to 70° C. After cooling to room temperature, insoluble materials were filtered off, and the pH of the filtrate was adjusted to 4. After being concentrated under reduced pressure, the residue was chromatographed over silica gel. Elution with a 4:1 (v/v) mixture of acetonitrile/distilled water gave the above-indicated compound (310 mg) in/pale white solid.

m.p.: 155° C.~(decomp.).

NMR: δ ($D_2O$+$NaHCO_3$) 1.49 (s, 6H), 3.58 (ABq, 2H), 4.22 (ABq, 2H), 5.16 (d, 1H), 5.56 (s, 1H), 5.77 (d, 1H), 6.94 (s, 1H).

MS(FAB. M+1): 625.

IR(KBr. $cm^{-1}$): 1770 (β-lactam), 1690, 1610, 1570.

EXAMPLE 30

Synthesis of 7-[(Z)-2-(2-aminothiazol-4-yl)-2-(1-carboxyeth-1-oxyimino)acetamido]-3-(1,4,6-triaminopyrimidinium-2-yl) thiomethyl-3-cephem-4-carboxylate 3-Acetoxymethyl-7-[(Z)-2-(2-aminothiazol-4-yl)-2-(1-carboxyeth-1-oxyimino)acetamido[-3-cephem-4-carboxylic acid (500 mg) was reacted in the same manner as described in Example 29 to give the above-indicated compound (230 mg) in a pale yellow solid.

m.p.: 167° C.~(decomp.).

NMR: δ ($D_2O$+acetone-$d_6$) 1.44 (d, 3H), 3.55 (ABq, 2H), 4.21 (ABq, 2H), 5.17 (d, 1H), 5.54 (s, 1H), 5.76 (d, 1H), 6.97 (s, 1H).

MS(FAB. M+1): 611.

IR(KBr. $cm^{-1}$): 1765 (β-lactam), 1660, 1590, 1540.

EXAMPLE 31

Synthesis of 7-[(Z)-2-(5-amino-1,2,4-thiadiazol-3-yl)-2-(2-carboxy-prop-2-oxyimino)acetamido]-3-(1,4,6-triaminopyrimidinium -2-yl)thiomethyl-3-cephem-4-carboxylate 3-Acetoxymethyl-7-[(Z)-2-(5-amino-1,2,4-thiadiazol-3-yl)-2-(2-carboxyprop-2-oxyimino)acetamido]-3-cephem-4-carboxylic acid (500 mg) was reacted in the same manner as described in Example 29 to give the above-indicated compound (280 mg) in a pale white solid.

m.p.: 173° C.~(decomp.).

NMR: δ ($D_2O$+$NaHCO_3$) 1.52 (s, 6H), 3.52 (ABq, 2H), 4.23 (ABq, 2H), 5.16 (d, 1H), 5.54 (s, 1H), 5.81 (d, 1H).

IR(KBr. $cm^{-1}$): 1760 (β-lactam), 1690, 1610, 1570.

EXAMPLE 32

Synthesis of 7-[(Z)-2-(5-amino-1,2,4-thiadiazol-3-yl)-2-(methoxyimino)acetamido]-3-(4,6-diamino-1-methylpyrimidinium-2-yl)thiomethyl-3-cephem-4-carboxylate To a solution of 3-acetoxymethyl-7-[(Z)-(5-amino-1,2,4-thiadiazol-3-yl)2-(methoxymino)acetamido]-3-cephem-4-carboxylic acid (500 mg) suspended in distilled water (5 ml) were added 4,6-diamino-1-methyl-2(1H)-pyrimidinethione (200 mg) and potassium iodide (800 mg). With adjusting of the pH of the mixture to 7.1~7.2 with a sodium bicarbonate solution, the reaction mixture was heated to 70° C. After stirring for 4 hours, the mixture was cooled to room temperature. The pH was adjusted to 3~3.5 with 2N-hydrochloric acid, and the resultant precipitates were filtered, washed with distilled water (5 ml), and chromatographed over silica gel. Elution with a 5:1 (v/v) mixture of acetonitrile/distilled water gave the above-indicated compound (300 mg) in a pale white solid.

m.p.: 161° C.~(decomp.)

NMR: δ($D_2O$+acetone-$d_6$) 3.62 (s, 3H), 3.66 (ABq, 2H), 4.05 (s, 3H), 4.45 (ABq, 2H), 5.15 (d, 1H), 5.62 (s, 1H), 5.81 (d, 1H).

IR(KBr. $cm^{-1}$): 1765 (β-lactam), 1680, 1630, 1570.

EXAMPLE 33

Synthesis of 7-[(Z)-2-(5-amino-1,2,4-thiadiazol-3-yl)-2-(methoxyimino)acetamido]-3-(4,6-diamino-1-ethylpyrimidinium-2-yl)thiomethyl-3-cephem-4-carboxylate 3-Acetoxymethyl-7-[(Z)-2-(5-amino-1,2,4-thiadiazol-3-yl)-2-(methoxyimino)acetamido]-3-cephem-4-carboxylic acid (500 mg) and 4,6-diamino-1-ethyl-2(1H)-pyrimidinethione (200 mg) were reacted in the same manner as described in Example 32 to give the above-indicated compound (230 mg).

m.p.: 169° C.~(decomp.)

NMR: δ($D_2O$+acetone-$d_6$) 3.60 (q, 2H), 3.60 (ABq, 2H), 4.05 (s, 3H), 4.55 (ABq, 2H), 5.11 (d, 1H), 5.68 (s, 1H), 5.82 (d, 1H).

IR(KBr. $cm^{-1}$): 1770 (β-lactam), 1690, 1630, 1580.

EXAMPLE 34

Synthesis of 7-[(Z)-2-(5-amino-1,2,4-thiadiazol-3-yl)-2-(methoxyimino)acetamido]-3-(4,6-diamino-1-propylpyrimidinium-2-yl)thiomethyl-3-cephem-4-carboxylate 3-Acetoxymethyl-7-[(Z)-2-(5-amino-1,2,4-thiadiazol-3-yl)-2-(methoxyimino)acetamido]-3-cephem-4-carboxylic acid (500 mg) and 4,6-diamino-1-propyl-2(1H)-pyrimidinethione (200 mg) were reacted in the same manner as described in Example 32 to give the above-indicated compound (250 mg).

m.p.: 67° C.~(decomp.)

NMR: δ ($D_2O$+acetone-$d_6$) 1.05 (t, 3H), 1.80 (m, 2H), 3.52 (ABq, 2H), 3.80 (t, 2H), 4.05 (s, 3H), 4.55 (ABq, 2H), 5.16 (d, 1H), 5.65 (s, 1H), 5.84 (d, 1H).

IR(KBr, $cm^{-1}$): 1765 (β-lactam), 1695, 1640, 1580.

EXAMPLE 35

Synthesis of 7-[(Z)-2-(5-amino-1,2,4-thiadiazol-3-yl)-2-(methoxyimino)acetamido]-3-(1-allyl-4,6-diaminopyrimidinium-2-yl)thiomethyl-3-cephem-4-carboxylate 3-Acetoxymethyl-7-[(Z)-2-(5-amino-1,2,4-thiadiazol-3-yl)-2-(methoxyimino) acetamido]-3-cephem-4-carboxylic acid (500 mg) and 1-allyl-4,6-diamino-2(1H)-pyrimidinethione (200 mg) were reacted in the same manner as described in Example 32 to give the above-indicated compound(170 mg).

m.p.: 158° C.~(decomp.).

NMR: δ ($D_2O$+acetone-$d^6$) 3.56 (ABq, 2H), 4.05 (s, 3H), 4.42 (ABq, 2H), 5.16 (d, 1H), 5.70 (s, 1H), 5.85 (d, 1H), 5.05~6.51 (m, 5H).

IR(KBr, $cm^{-1}$): 1760 (β-lactam), 1700, 1650, 1590.

EXAMPLE 36

Synthesis of 7-[(Z)-2-(5-amino-1,2,4-thiadiazol-3-yl)-2-(ethoxyimino)acetamido]-3-(4,6-diamino-1-methylpyrimidinium-2-yl)thiomethyl-3-cephem-4-carboxylate 3-Acetoxymethyl-7-[(Z)-2-(5-amino-1,2,4-thiadiazol-3-yl)-2-(ethoxyimino) acetamido]-3-cephem-4-carboxylic acid (500 mg) and 4,6-diamino-1-methyl-2(1H)-pyrimidinethione (200 mg) were reacted in the same manner as described in Example 32 to give the above-indicated compound (280 mg).

m.p.: 163° C.~(decomp.).

NMR: δ ($D_2O$+acetone-$d_6$) 1.30 (t, 3H), 3.60 (s, 3H), 3.56 (ABq, 2H), 4.30 (q, 2H), 4.40 (ABq, 2H), 5.13 (d, 1H), 5.62 (s, 1H), 5.84 (d, 1H).

IR(KBr, $cm^{-1}$): 1768 (β-lactam), 1690, 1630, 1580.

EXAMPLE 37

Synthesis of 7-[(Z)-2-(5-amino-1,2,4-thiadiazol-3-yl)-2-(ethoxyimino)acetamido]-3-(4,6-diamino-1-ethylpyrimidinium-2-yl)thiomethyl-3-cephem-4-carboxylate 3-Acetoxymethyl-7-[(Z)-2-(5-amino-1,2,4-thiadiazol-3-yl)-2-(ethoxyimino) acetamido]-3-cephem-4-carboxylic acid (500 mg) and 4,6-diamino-1-ethyl-2(1H)-pyrimidinethione (200 mg) were reacted in the same manner as described in Example 32 to give the above-indicated compound(270 mg).

m.p.: 165° C.~(decomp.).

NMR: δ ($D_2O$+acetone-$d_6$) 1.18 (t, 3H), 1.30 (t, 3H), 3.60 (q, 2H), 3.58 (ABq, 2H), 4.30 (q, 2H), 4.40 (ABq, 2H), 5.18 (d, 1H), 5.71 (s, 1H), 5.84 (d, 1H).

IR(KBr, $cm^{-1}$): 1765 (β-lactam), 1695, 1630, 1570.

EXAMPLE 38

Synthesis of 7-[(Z)-2-(5-amino-1,2,4-thiadiazol-3-yl)-2-(ethoxyimino)acetamido]-3-(4,6-diamino-1-propylpyrimidinium-2-yl)thiomethyl-3-cephem-4-carboxylate 3-Acetoxymethyl-7-[(Z)-2-(5-amino-1,2,4-thiadiazol-3-yl)-2-(ethoxyimino)acetamido]-3-cephem-4-carboxylic acid (500 mg) and 4,6-diamino-1-propyl-2(1H)-pyrimidinethione (200 mg) were reacted in the same manner as described in Example 32 to give the above-indicated compound(230 mg).

m.p.: 158° C.~(decomp.)

NMR: δ ($D_2O$+acetone-$d_6$) 1.05 (t, 3H), 1.30 (t, 3H), 1.80 (m, 2H), 3.54 (ABq, 2H), 4.0 (t, 2H), 4.32 (q, 2H), 4.58 (ABq, 2H), 5.18 (d, 1H), 5.69 (s, 1H), 5.84 (d, 1H).

IR(KBr, $cm^{-1}$): 1770 (β-lactam), 1690, 1640, 1580.

EXAMPLE 39

Synthesis of 7-[(Z)-2-(5-amino-1,2,4-thiadiazol-3-yl)-2-(ethoxyimino)acetamido]-3-(1-allyl-4,6-diaminopyrimidinium-2-yl)thiomethyl-3-cephem-4-carboxylate 3-Acetoxymethyl-7-[(Z)-2-(5-amino-1,2,4-thiadiazol-3-yl)-2-(ethoxyimino)acetamido]-3-cephem-4-carboxylic acid (500 mg) and 1-allyl-4,6-diamino-2(1H)-pyrimidinethione (200 mg) were reacted in the same manner as described in Example 32 to give the above-indicated compound(210 mg).

m.p.: 159° C.~(decomp.)

NMR: δ ($D_2O$+acetone-$d_6$) 1.31 (t, 3H), 3.60 (ABq, 2H), 4.32 (q, 2H), 4.42 (ABq, 2H), 5.16 (d, 1H), 5.68 (s, 1H), 5.82 (d, 1H), 5.05~6.51 (m, 5H).

IR(KBr. $cm^{-1}$): 1769(β-lactam), 1695, 1630, 1570.

EXAMPLE 40

Synthesis of 7-[(Z)-2-(5-amino-1,2,4-thiadiazol-3-yl)-2-(2-carboxyprop-2-oxyimino)acetamido]-3-(4,6-diamino-1-methylpyrimidinium-2-yl)thiomethyl-3-cephem-4-carboxylate To a solution of 3-acetoxymethyl-7-[(Z)-2-(5-amino-1,2,4-thiadiazol-3-yl)-2-(2-carboxyprop-2-oxyimino)acetamido9-3-cephem-4-carboxylic acid (500 mg) suspended in distilled water (10 ml) were added 4,6-diamino-1-methyl-2(1H)-pyrimidinethione (200 mg) and potassium iodide (1.2 g). After adjusting the pH of the reaction mixture to 7.3~7.5 with a sodium bicarbonate solution, the reaction mixture was stirred for 4 hours at 70° C. The mixture was cooled to room temperature, and insoluble materials were filtered off, and pH of the filtrate was adjusted to 4. After concentration under reduced pressure, the residue was chromatographed over silica gel. Elution with a 4:1 (v/v) mixture of acetonitrile/distilled water gave the above-indicated compound (200 mg) in a pale white solid.

m.p.: 154° C.~(decomp.).

NMR: δ ($D_2O$+acetone-$d_6$) 1.52 (s, 6H), 3.51 (s, 3H), 3.58 (ABq, 2H), 4.40 (ABq, 2H), 5.18 (d, 1H), 5.60 (s, 1H), 5.81 (d, 1H).

IR(KBr. $cm^{-1}$): 1769 (β-lactam), 1700, 1650, 1590.

EXAMPLE 41

Synthesis of 7-[(Z)-2-(5-amino-1,2,4-thiadiazol-3-yl)-2-(2-carboxyprop-2-oxyimino)acetamido]-3-(4,6-diamino-1-ethylpyrimidinium-2-yl)thiomethyl-3-cephem-4-carboxylate 3-Acetoxymethyl-7-[(Z)-2-(5-amino-1,2,4-thiadiazol-3-yl)-2-(2-carboxyprop-2-oxyimino)acetamido]-3-cephem-4-carboxylic acid (500 mg) and 4,6-diamino-1-ethyl-2(1H)-pyrimidinethione (200 mg) were reacted in the same manner as described in Example 40 to give the above-indicated compound(250 mg).

m.p.: 161° C.~ (decomp.). NMR: δ ($D_2O$+acetone-$d_6$) 1.32 (t, 3H), 1.58 (s, 6H), 3.56 (ABq, 2H), 4.02 (q, 2H), 4.43 (ABq, 2H), 5.18 (d, 1H), 5.58 (s, 1H), 5.81 (d, 1H).

IR(KBr. $cm^{-1}$): 1767 (β-lactam), 1695, 1640,. 1580.

EXAMPLE 42

Synthesis of 7-[(Z)-2-(5-amino-1,2,4-thiadiazol-3-yl)-2-(2-carboxyprop-2-oxyimino)acetamido]-3-(4,6-diamino-1-propylpyrimidinium-2-yl)thiomethyl-3-cephem-4-carboxylate 3-Acetoxymethyl-7-[(Z)-2-(5-amino-1,2,4-thiadiazol-3-yl)-2-(2-carboxyprop-2-oxyimino)acetamido]-3-cephem-4-carboxylic acid(500 mg) and 4,6-diamino-1-propyl-2(1H)-pyrimidinethione (200 mg) were reacted in the same manner as described in Example 40 to give the above-indicated compound(190 mg).

m.p.: 159° C.~(decomp.). NMR: δ ($D_2O$+acetone-$d_6$) 1.02 (t, 3H), 1.52 (s, 6H), 1.53 (m, 2H), 3.60 (ABq, 2H), 3.98 (t, 2H), 4.45 (ABq, 2H), 5.18 (d, 1H), 5.58 (s, 1H), 5.81 (d, 1H).

IR(KBr, $cm^{-1}$): 1765 (β-lactam), 1690, 1630, 1570.

EXAMPLE 43

Synthesis of 7-[(Z)-2-(5-amino-1,2,4-thiadiazol-3-yl)-2-(2-carboxyprop-2-oxyimino)acetamido]-3-(1-butyl-4,6-diamino pyrimidinium-2-yl)thiomethyl-3-cephem-4-carboxylate 3-acetoxymethyl-7-[(Z)-2-(5-amino-1,2,4-thiadiazol-3-yl)-2-(2-carboxyprop-2-oxyimino)acetamido]-3-cephem-4-carboxylic acid (500 mg) and 1-butyl-4,6-diamino-2(1H)-pyrimidinethione (200 mg) were reacted in the same manner as described in Example 40 to give the above-indicated compound(160 mg).

m.p.: 163° C.~(decomp.). NMR: δ ($D_2O$+acetone-$d_6$) 0.98 (t, 3H), 1.50 (m, 4H), 1.54 (s, 6H), 3.60 (ABq, 2H), 3.95 (t, 2H), 4.46 (ABq, 2H), 5.18 (d, 1H), 5.58(s, 1H), 5.81 (d, 1H).

IR(KBr, $cm^{-1}$): 1770 (β-lactam), 1690, 1620, 1550.

EXAMPLE 44

Synthesis of 7-[(Z)-2-(5-amino-1,2,4-thiadiazol-3-yl)-2-(2-carboxyprop-2-oxyimino)acetamido]-3-(1-allyl-4,6-diaminopyrimidinium-2-yl)thiomethyl-3-cephem-4-carboxylate 3-Acetoxymethyl-7-[(Z)-2-(5-amino-1,2,4-thiadiazol-3-yl)-2-(2-carboxyprop-2-oxyimino)acetamido]-3-cephem-4-carboxylic acid (500 mg) and 1-allyl-4,6-diamino-2(1H)-pyrimidinethione (200 mg) were reacted in the same manner as described in Example 40 to give the above-indicated compound (210 mg).

m.p.: 156° C.~(decomp.)

NMR: δ ($D_2O$+acetone-$d_6$) 1.58 (s, 6H), 3.60 (ABq, 2H), 3.71 (d, 2H), 4.45 (ABq, 2H), 5.18 (d, 1H), 5.60 (s, 1H), 5.81 (d, 1H), 5.01~6.51 (m, 3H).

IR(KBr, $cm^{-1}$): 1760 (β-lactam), 1680, 1620, 1570.

EXAMPLE 45

Synthesis of 7-[(Z)-2-(2-aminothiazol-4-yl)-2-(2-carboxyprop-2-oxyimino)acetamido]-3-(4,6-diamino-1,5-dimethylpyrimidinium-2-yl)thiomethyl-3-cephem-4-carboxylate To 3-acetoxymethyl-7-[(Z)-2-(2-aminothiazol-4-yl)-2-(2-carboxyprop-1-oxyimino)acetamido]-3-cephem-4-carboxylic acid (500 mg) were added 4,6-diamino-1,5-dimethyl-2(1H)-pyrimidinethione (200 mg) obtained in Preparation 7, potassium iodide (800 mg) and distilled water (30 ml). With adjusting of the pH of the mixture to 7.0~7.5 with a saturated aqueous sodium bicarbonate solution, the reaction mixture was stirred for 4 hours at 70°~75° C. After the mixture was cooled to room temperature, the pH of the mixture was adjusted to 4.5~5.0 with 2N-hydrochloric acid. The precipitates were collected by filteration and chromatographed over silica gel. Elution with a 7:1 (v/v) mixture of acetonitrile/distilled water gave the above-indicated compound (126 mg) in a pale yellow solid.

m.p.: 174° C.~(decomp.).

NMR: δ ($D_2O$+$NaHCO_3$) 1.48 (s, 6H), 2.21 (s, 3H), 3.33 and 3.73 (ABq, 2H), 3.49 (s, 3H), 3.89 and 4.72 (ABq, 2H), 5.18 (d, 1H), 5.78 (d, 1H), 6.92 (s, 1H).

MS(FAB, M+1): 638.

IR(KBr, $cm^{-1}$): 1770 (β-lactam), 1761, 1590, 1527.

EXAMPLE 46

Synthesis of 7-[(Z)-2-(2-aminothiazol-4-yl)-2-(2-carboxyprop-2-oxyimino)acetamido]-3-(4,6diamino-5-ethyl-1-methyl-pyrimidinium-2-yl)thiomethyl-3-cephem-4-carboxylate The above-indicated compound (130 mg) in a pale white solid was prepared in the same method as described in Example 45 except for using 4,6-diamino-5-ethyl-1-methyl-2(1H)-pyrimidinethione (200 mg) obtained in Preparation 10 in place of 4,6-diamino-1,5-dimethyl-2(1H)-pyrimidinethione.

m.p.: 178° C.~(decomp.)

NMR: δ (DMSO-$d_6$) 0.93 (t, 3H), 1.42 (d, 6H), 2.38 (q, 2H), 3.19 and 3.54 (ABq, 2H), 3.49 (s, 3H), 3.85 and 4.80 (ABq, 2H), 4.96 (d, 1H), 5.68 (dd, 1H), 6.75 (s, 1H), 7.20 (s, 2H), 7.71 (bs, 4H), 11.42 (bs, 1H).

MS(FAB, M+1): 652.

IR(KBr, $cm^{-1}$): 1769 (β-lactam), 1685, 1632, 1580.

EXAMPLE 47

Synthesis of 7-[(Z)-2-(2-aminothiazol-4-yl)-2-(2-carboxyprop-2-oxyimino)acetamido]-3-(4,6-diamino-1-ethyl-5-methyl-pyrimidinium-2-yl)thiomethyl-3-cephem-4-carboxylate The above-indicated compound (150 mg) in yellow solid was prepared in the same method as described in Example 45 except for using 4,6-diamino-1-ethyl-5-methyl-2(1H)-pyrimidinethione (200 mg) obtained in Preparation 8 in place of 4,6-diamino-1,5-dimethyl-2(1H)-pyrimidinethione.

m.p.: 180° C.~(decomp.).

NMR: δ (DMSO-$d_6$). 1.22 (t, 3H), 1.42 (d, 6H), 1.90 (s, 3H), 3.20 and 3.55 (ABq, 2H), 3.89 and 4.78 (ABq, 2H), 4.10 (q, 2H), 4.98 (d, 1H), 5.70 (dd, 1H), 6.79 (s, 1H), 7.22 (s, 2H), 7.78 (bs, 4H), 11.24 (bs, 1H).

MS(FAB, M+1): 652.

IR(KBr, $cm^{-1}$): 1765 (β-lactam), 1685, 1630, 1580.

EXAMPLE 48

Synthesis of 7-[(Z)-2-(2-aminothiazol-4-yl)-2-(2-carboxyprop-2-oxyimino)acetamido]-3-(4,6-diamino-1,5-diethyl-pyrimidinium-2-yl)thiomethyl-3-cephem-4-carboxylate The above-indicated compound (140 mg) in a pale yellow solid was prepared in the same method as described in Example 45 except for using 4,6-diamino-1,5-diethyl-2(1H)-pyrimidinethione (200 mg) obtained in Preparation 11 in place of 4,6-diamino-1,5-dimethyl-2(1H)-pyrimidinethione.

m.p.: 168° C.~(decomp.).

NMR: δ (DMSO-$d_6$) 0.97 (t, 3H), 1.22 (t, 3H), 1.43 (d, 6H), 2.40 (q, 2H), 3.20 and 3.56 (ABq, 2H), 3.84 and 4.81 (ABq, 2H), 4.08 (q, 2H), 4.98 (d, 1H), 5.70 (dd, 1H), 6.74 (s, 1H), 7.20 (s, 2H), 7.71 (bs, 4H), 11.45 (bs, 1H).

MS(FAB, M+1): 666.

IR(KBr, $cm^{-1}$): 1766 (β-lactam), 1640, 1600.

Example 49

Synthesis of 7-[(Z)-2-(2-aminothiazol-4-yl)-2-(2-carboxyprop-2-oxyimino)acetamido]-3-(5-methyl-1,4,6-triaminopyrimidinium-2-yl)thiomethyl-3-cephem-4-carboxylate The above-indicated compound (170 mg) in a pale yellow solid was prepared in the same method as described in Example 45 except for using 5-methyl-1,4,6-triamino-2(1H)-pyrimidinethione (200 mg) obtained in Preparation 9 in place of 4,6-diamino-1,5-dimethyl-2(1H)-pyrimidinethione.

m.p.: 178° C.~(decomp.)

NMR: δ (DMSO-$d_6$) 1.43 (d, 6H), 1.82 (s, 3H), 3.19 and 3.48 (ABq, 2H), 3.72 and 4.52 (ABq, 2H), 4.99 (d, 1H), 5.68 (dd, 1H), 6.11 (s, 2H), 6.73 (s, 1H), 7.22 (s, 2H), 7.70 (bs, 4H), 11.31 (bs, 1H).

MS(FAB, M+1): 639.

IR(KBr, $cm^{-1}$): 1765 (β-lactam), 1628, 1590.

Example 50

Synthesis of 7-[(Z)-2-(2-aminothiazol-4-yl)-2-(2-carboxyprop-2-oxyimino)acetamido]-3-(1-cyclopropyl-4,6-diaminopyrimidinium-2-yl)thiomethyl-3-cephem-4-carboxylate To a solution of 3-acetoxymethyl-7-[(Z)-2-(2-amino-thiazol-4-yl)-2-(carboxyprop-2-oxyimino)acetamido]-3-cephem-4-carboxylic acid dihydrochoride (500 mg) suspended in distilled water (10 ml) were added 1-cyclopropyl-4,6diamino-2(1H)-pyrimidinethione (200 mg) and potassium iodide (1.2 g). With adjusting of the pH of the reaction mixture to 7.3~7.5 with a sodium bicarbonate solution, the reaction mixture was stirred for 4 hours at 70° C. After the mixture was cooled to room temperature, insoluble materials were filtered off, and the pH of the filtrate was adjusted to 4. After being concentrated under reduced pressure, the residue was chromatographed over silica gel. Elution with a 4:1 (v/v) mixture of acetonitrile/distilled water gave the above-indicated compound (150 mg) in a pale yellow solid.

m.p.: 194° C.~(decomp.).

NMR: δ ($D_2O$+$NaHCO_3$) 1.18 (m, 2H), 1.50 (m, 2H), 3.00 (m, 1H), 1.44 (s, 6H), 3.41 (ABq, 2H), 4.32 (ABq, 2H), 5.11 (d, 1H), 5.66 (s, 1H), 5.71 (d, 1H), 6.92 (s, 1H).

MS(FAB, M+1): 650.

IR(KBr, $cm^{-1}$): 1768 (β-lactam), 1645, 1600.

EXAMPLE 51

Synthesis of 7-[(Z)-2-(2-aminothiazol-4-yl)-2-(2-carboxyprop-2-oxyimino)acetamido]-3-[1-(4-chlorophenyl)-4,6-diaminopyrimidinium-2-yl)thiomethyl-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid (500 mg) and 1-(4-chlorophenyl)-4,6-diamino-2(1H)-pyrimidinethione (200 mg) were reacted in the same manner as described in Example 50 to give the above-indicated compound (170 mg).

m.p.: 182° C.～(decomp.)

NMR: δ ($D_2O+NaHCO_3$) 1.43 (s, 6H), 3.42 (ABq, 2H), 4.35 (ABq, 2H), 5.08 (d, 1H), 5.64 (s, 1H), 5.66 (d, 1H), 6.84 (s, 1H), 7.26～7.62 (m, 4H).

MS(FAB, M+1): 720.

IR(KBr, $cm^{-1}$): 1768 (β-lactam), 1643, 1600.

EXAMPLE 52

Synthesis of 7-[(Z)-2-(2-aminothiazol-4-yl)-2-(-carboxymethoxyimino)acetamido]-3-(4,6-diamino-1-phenylpyrimidinium-2-yl)thiomethyl-3-cephem-4-carboxylate 3-Acetoxymethyl-7-[(Z)-2-(2-aminothiazol-4-yl)-2-(-carboxymethoxyimino)acetamido]-3-cephem-4-carboxylic acid (500 mg) and 4,6-diamino-1-phenyl-2(1H)-pyrimidinethione (200 mg) were reacted in the same manner as described in Example 50 to give the above-indicated compound (190 mg).

m.p.: 187° C.～(decomp.).

NMR: δ ($D_2O+NaHCO_3$) 3.48 (ABq, 2H), 4.42 (ABq, 2H), 4.59 (s, 2H), 5.08 (d, 1H), 5.69 (s, 1H), 5.71 (d, 1H), 6.96 (s, 1H), 7.41～7.82 (m, 5H).

MS(FAB, M+1): 658.

IR(KBr, $cm^{-1}$): 1766 (β-lactam), 1655, 1600, 1538.

EXAMPLE 53

Synthesis of 7-[(Z)-2-(2-aminothiazol-4-yl)-2-(1-carboxyeth-1-oxyimino)acetamido]-3-(4,6-diamino-1-phenylpyrimidinium-2-yl)thiomethyl-3-cephem-4-carboxylate 3-Acetoxymethyl-7-[(Z)-2-(2-aminothiazol-4-yl)-2-(1-carboxyeth-1-oxyimino)acetamido]-3-cephem-4-carboxylic acid (500 mg) and 4,6-diamino-1-phenyl-2(1H)-pyrimidinethione (200 mg) were reacted in the same manner as described in Example 50 to give the above-indicated compound (210 mg).

m.p.: 156° C.～(decomp.).

NMR: δ ($D_2O+NaHCO_3$) 1.48 (d, 3H), 3.48 (ABq, 2H), 4.49 (ABq, 2H), 5.16 (d, 1H), 5.76 (s, 1H), 5.79 (d, 1H), 6.97 (s, 1H), 7.48～7.83 (m, 5H).

MS(FAB, M+1): 672.

IR(KBr, $cm^{-1}$): 1765 (β-lactam), 1655, 1598, 1515.

EXAMPLE 54

Synthesis of 7-[(Z)-2-(2-aminothiazol-4-yl)-2-(ethoxyimino)acetamido]-3-(4,6-diamino-1-phenylpyrimidinium-2-yl)thiomethyl-3-cephem-4-carboxylate 3-Acetoxymethyl-7-[(Z)-2-(aminothiazol-4-yl)-2-(ethoxyimino)acetamido]-3-cephem-4-carboxylic acid (500 mg) and 4,6-diamino-1-phenyl-2(1H)-pyrimidinethione (200 mg) were reacted in the same manner as described in Example 50 to give the above-indicated compound (130 mg).

m.p.: 182° C.～(decomp.)

NMR: δ ($D_2O+NaHCO_3$) 1.28 (t, 3H), 3.52 (ABq, 2H), 4.20 (q, 2H), 4.31 (ABq, 2H), 5.16 (d, 1H), 5.76 (s, 1H), 5.81 (d, 1H), 6.88 (s, 1H), 7.48～7.82 (m, 5H).

MS(FAB, M+1): 628.

IR(KBr, $cm^{-1}$): 1768 (β-lactam), 1643, 1612, 1600, 1515.

EXAMPLE 55

Synthesis of 7-[(Z)-2-(2-aminothiazol-4-yl)-2-(ethoxyimino)acetamido]-3-[1-(4-chlorophenyl)-4,6-diaminopyrimidinium-2-yl)thiomethyl-3-cephem-4-carboxylate 3-Acetoxymethyl-7-[(Z)-2-(2-aminothiazol-4-yl)-2-ethoxyimino)acetamido]-3-cephem-4-carboxylic acid (500 mg) and 1-(4-chlorophenyl-4,6-diamino-2(1H)-pyrimidinethione (200 mg) were reacted in the same manner as described in Example 50 to give the above-indicated compound (170 mg).

m.p.: 177° C.～(decomp.)

NMR: δ ($D_2O$+acetone-$d_6$) 1.28 (t, 3H), 3.48 (ABq, 2H), 4.21 (q, 2H), 4.32 (ABq, 2H), 5.12 (d, 1H), 5.73 (s, 1H), 5.80 (d, 1H), 6.87 (s, 1H), 7.52～7.79 (m, 4H).

MS(FAB, M+1): 662.

IR(KBr, $cm^{-1}$): 1665 (β-lactam), 1643, 1610, 1530.

EXAMPLE 56

Synthesis of 7-[(Z)-2-(2-aminothiazol-4-yl)-2-(2-carboxyprop-2-oxyimino)acetamido]-3-[4,6-diamino-1-(2,4-dimethylphenyl)pyrimidinium-2-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid (500 mg) and 4,6-diamino-1-(2,4-dimethylphenyl)-2(1H)-pyrimidinethione (200 mg) were reacted in the same manner as described in Example 50 to give the above-indicated compound (180 mg).

m.p.: 189° C.～(decomp.).

NMR: δ ($D_2O+NaHCO_3$) 1.44 (s, 6H), 2.02 (s, 3H), 2.34 (s, 3H), 3.36 (ABq, 2H), 4.27 (ABq, 2H), 5.06 (d, 1H), 5.68 (s, 1H), 5.71 (d, 1H), 6.88 (s, 1H), 7.08～7.35 (m, 3H).

MS(FAB, M+1): 714.

IR(KBr, $cm^{-1}$): 1768 (β-lactam), 1641, 1600, 1552.

EXAMPLE 57

Synthesis of 7-[(Z)-2-(2-aminothiazol-4-yl)-2-(ethoxyimino)acetamido]-3-[(4,6-diamino-1-(2,4-dimethylphenyl)-pyrimidinium-2-yl]thiomethyl-3-cephem-4-carboxylate 3-Acetoxymethyl-7-[(Z)-2-(2-aminothiazol-4-yl)-2-ethoxyimino)acetamido]-3-cephem-4-carboxylic acid (500 mg) and 4,6-diamino-1-(2,4-dimethylphenyl)-2(1H)-pyrimidinethione (200 mg) were reacted in the same manaer as described in Example 50 to give the above-indicated compound (130 mg).

m.p.: 176° C.～(decomp.).

NMR: δ ($D_2O$+acetone-$d_6$) 1.29 (t, 3H), 2.12 (s, 3H), 2.40 (s, 3H), 3.51 (ABq, 2H), 4.21 (q, 2H), 4.36 (ABq, 2H), 5.09 (d, 1H), 5.76 (s, 1H), 5.81(d, 1H), 6.90 (s, 1H), 7.23～7.41 (m, 3H).

MS(FAB, M+1): 656.

IR(KBr, $cm^{-1}$): 1770 (β-lactam), 1643, 1610, 1540.

EXAMPLE 58

Synthesis of 7-[(Z)-2-(2-aminothiazol-4-yl)-2-(2-carboxyprop-2-oxyimino)acetamido]-3-[4,6-diamino-1-(2,6-dimethoxyphenyl) -pyrimidinium-2-yl]thiomethyl-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid (500 mg) and 4,6-diamino-1-(2, 6-dimethoxyphenyl)-2(1H)-pyrimidinethione (200 mg) were reacted in the same manner as described in Example 50 to give the above-indicated compound (210 mg).

m.p.: 164° C.~(decomp.)

NMR: $\delta(D_2O+NaHCO_3)$ 1.46 (s, 6H), 3.40 (ABq, 2H), 3.79 (s, 6H), 4.29 (ABq, 2H), 5.12 (d, 1H), 5.67 (s, 1H), 5.76 (d, 1H), 7.04~7.28 (m, 3H).

MS(FAB, M+1): 7.46.

IR(KBr, $cm^{-1}$): 1766 (β-lactam), 1641, 1600, 1550.

EXAMPLE 59

Synthesis of 7-[(Z)-2-(2-aminothiazol-4-yl)-2-(2-carboxyprop-2-oxyimino)acetamido]-3-[(4,6-diamino-1-(4-hydroxyphenyl)-pyrimidinium-2-yl]thiomethyl-3-cephem-4-carboxylate 3-Acetoxymethyl-7-[(Z)-2-(2-aminothiazol-4-yl)-2-(2-carboxyprop-2-oxyimino)acetamido]-3-cephem-4-carboxylic acid (500 mg) and 4,6-diamino-1-(4-hydroxyphenyl)-2(1H)-pyrimidinethione (200 mg) were reacted in the same manner as described in Example 50 to give the above-indicated compound (230 mg).

m.p.: 171° C.~(decomp.).

NMR: $\delta(D_2O+NaHCO_3)$ 1.47 (s, 6H), 3.39 (ABq, 2H), 4.27 (ABq, 2H), 5.06 (d, 1H). 5.64 (s, 1H), 5.74 (d, 1H), 6.91 (s, 1H), 6.90~7.32 (m, 4H).

MS(FAB, M+1): 702.

IR(KBr, $cm^{-1}$): 1768 (β-lactam), 1641, 1600, 1525.

What is claimed is:

1. A cephalosporin compound of the formula

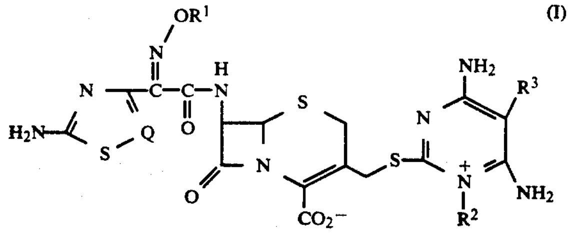

(I)

wherein $R^1$ is a $C_{14}$ alkyl, $C_{3-4}$ alkenyl, $C_{3-4}$ alkynyl group, or $-C(R^a)(R^b)CO_2H$, wherein $R^a$ and $R^b$ are the same or different, and each is a hydrogen atom or a $C_{1-4}$ alkyl group, or $R^a$ and $R^b$ form a $C_{3-7}$ cycloalkyl group with the carbon atom to which they are linked;

$R^2$ is a $C_{1-4}$ alkyl group, $C_{3-4}$ alkenyl group, $C_{3-4}$ cycloalkyl group, an amine group substituted by 0–2 $C_{1-4}$ alkyl groups, or a phenyl group substituted by 0–2 substituents selected from the group consisting of $C_{1-4}$ alkyl, $C_{1-3}$ alkoxy, halogen and hydroxy;

$R^3$ is hydrogen or a $C_{1-4}$ alkyl group; and

Q is N or CH;

or a pharmaceutically acceptable non-toxic salt thereof, or a physiologically hydrolyzable ester or solvate thereof.

2. The compound according to claim 1 which is 7-[(Z)-2-(2-aminothiazol-4-yl)-2-(2-carboxylprop-2-oxyimino)acetamido]-3-(4,6-diamino-1-methylpyrimidinium-2-yl)thiomethyl-3-cephem-4-carboxylate.

3. The compound according to claim 1 which is 7-[(Z)-2-(2-aminothiazol-4-yl)-2-(2-carboxylprop-2-oxyimino)acetamino]-3-(4,6-diamino-1-ethylpyrimidinium-2-yl)thiomethyl-3-cephem-4-carboxylate.

4. The compound according to claim 1 which is 3-(1-allyl-4,6-diaminopyrimidinium-2-yl)thiomethyl-7-[(Z)-2-(2-aminothiazol-4-yl)-2-(2-carboxyprop-2-oxyimino)acetamido]-3-cephem-4-carboxylate.

5. The compound according to claim 1 which is 7-[(Z)-2-(2-aminothiazol-4-yl)-2-(1-carboxyeth-1-carboxyeth-1-oxyimino)acetamido]-3-(4,6-diamino-1-methylpyrimidinium-2-yl)thiomethyl-3-cephem-4-carboxylate.

6. The compound according to claim 1 which is 7-[(Z)-2-(2-aminothiazol-4-yl)-2-(1-carboxyeth-1-oxyimino)acetamido]-3-(4,6-diamino-1-ethylpyrimidinium-2-yl)thiomethyl-3-cephem-4-carboxylate.

7. The compound according to claim 1 which is 3-(1-allyl-4,6-diaminopyrimidinium-2-yl)thiomethyl-7-[(Z)-2-(2-aminothiazol-4-yl)-2-(1-carboxyeth-1-oxyimino)acetamido]-3-cephem-4-carboxylate.

8. The compound according to claim 1 which is 7-[(Z)-2-(2-aminothiazol-4-yl)-2-(carboxymethoxyimino)acetamido]-3-(4,6-diamino-1-methylpyrimidinium-2-yl)thiomethyl-3-cephem-4-carboxylate.

9. The compound according to claim 1 which is 7-[(Z)-2-(2-aminothiazol-4-yl)-2-(carboxymethoxyimino)acetamido]-3-(4,6-diamino-1-ethylprimidinium-2-yl)thiomethyl-3-cephem-4-carboxylate.

10. The compound according to claim 1 which is 3-(1-ally-4,6-diaminopyrimidinium-2-yl)thiomethyl-7-[(Z)-2-aminothiazol-4-yl)-2-(carboxymethoxyimino)acetamido]-3-cephem-4-carboxylate.

11. The compound according to claim 1 which is 7-[(Z)-2-(2-aminothiazol-4-yl)-2-(methoxyimino)acetamido]-3-(4,6-diamino-1-methylpyrimidinium-2-yl)thiomethyl-3-cephem-4-carboxylate.

12. The compound according to claim 1 which is 7-[(Z)-2-(2-aminothiazol-4-yl)-2-(ethoxyimino)acetamido]-3-(4,6-diamino-1-methylpyrimidinium-2-yl)thiomethyl-3-cephem-4-carboxylate.

13. The compound according to claim 1 which is 7-[(Z)-2-(2-aminothiazol-4-yl)-2-(ethoxyimino)acetamido]-3-(4,6-diamino-1-ethylpyrimidinium-2-yl)thiomethyl-3-cephem-4-carboxylate.

14. The compound according to claim 1 which is 7-[(Z)-2-(5-amino-1,2,4-thiadiazol-3-yl)-2-(2-carboxyprop-2-oxyimino)acetamido]-3-(1,4,6-triaminopryimidinium-2-yl)thiomethyl-3-cephem-4-carboxylate.

15. The compound according to claim 1 which is 7-[(Z)-2-(2-aminothiazol-4-yl)-2-(1-carboxyeth-1-oxyimino)acetamido]-3-(1,4,6-triaminopyrimidinium-2-yl)thiomethyl-3-cephem-4-carboxylate.

16. The compound according to claim 1 which is 7-[(Z)-2-(2-aminothiazol-4-yl)-2-(2-carboxyprop-2-oxyimino)acetamido]-3-(1,4,6-triaminopyrimidinium-2-yl)thiomethyl-3-cephem-4-carboxylate.

17. The compound according to claim 1 which is 7-[(Z)-2-(2-aminothiazol-4-yl)-2-(ethoxyimino)acetamido]-3-(1,4,6-triaminopyrimidinium-2-yl)thiomethyl-3-cephem-4-carboxylate.

18. The compound according to claim 1 which is 7-[(Z)-2-(5-amino-1,2,4-thiadiazol-3-yl)-2-(ethoxyimino)acetamido]-3-(1,4,6-triaminopyrimidinium-2-yl)thiomethyl-3-cephem-4-carboxylate.

19. The compound according to claim 1 which is 7-[(Z)-2-(2-aminothiazol-4-yl)-2-(2-propyn-1-oxyimino)acetamido]-3-(1,4,6-triaminopyrimidinium-2-yl)thiomethyl-3-cephem-4-carboxylate.

20. The compound according to claim 1 which is 7-[(Z)-2-(2-aminothiazol-4-yl)-2-(methoxyimino)acetamido]-3-(1,4,6-triaminopyrimidinium-2-yl) thiomethyl-3-cephem-4-carboxylate.

21. The compound according to claim 1 which is 7-[(Z)-2-(5-amino-1,2,4-thiadiazol-3-yl)-2-(ethoxyimino)acetamido]-3-(4,6-diamino-1-methylpyrimidinium-2-yl)thiomethyl-3-cephem-4-carboxylate.

22. The compound according to claim 1 which is 7-[(Z)-2-(5-amino-1,2,4-thiadiazol-3-yl)-2-(ethoxyimino)acetamido]-3-(4,6-diamino-1-ethylpyrimidinium-2-yl)thiomethyl-3-cephem-4-carboxylate.

23. The compound according to claim 1 which is 7-[(Z)-2-(5-amino-1,2,4-thiadiazol-3-yl)-2-(ethoxyimino)acetamido]-3-(4,6-diamino-1-propylpyrimidinium-2-yl)thiomethyl-3-cephem-4-carboxylate.

24. The compound according to claim 1 which is 3-(1-allyl-4,6-diaminopyrimidinium-2-yl)-7-[(Z)-2-(5-amino-1,2,4-thiadiazol-3-yl)-2-(ethoxyimino)acetamido]-3-cephem-4-carboxylate.

25. The compound according to claim 1 which is 7-[(Z)-2-(5-amino-1,2,4-thiadiazol-3-yl)-2-(methoxyimino)acetamido]-3-(4,6-diamino-1-methylpyrimidinium-2-yl)thiomethyl-3-cephem-4-carboxylate.

26. The compound according to claim 1 which is 7-[(Z)-2-(5-amino-1,2,4-thiadiazol-3-yl)-2-(methoxyimino)acetamido]-3-(4,6-diamino-1-ethylpyrimidinium-2-yl)thiomethyl-3-cephem-4-carboxylate.

27. The compound according to claim 1 which is 7-[(Z)-2-(5-amino-1,2,4-thiadiazol-3-yl)-2-(2-carboxyprop-2-oxymino)acetamido]-3-(4,6-diamino-1-methylpyrimidinium-2-yl)thiomethyl-3-cephem-4-carboxylate.

28. The compound according to claim 1 which is 7-[(Z)-2-(5-amino-1,2,4-thiadiazol-3-yl)-2-(2-carboxyprop-2-oxyimino)acetamido]-3-(4,6-diamino-1-ethylpyrimidinium-2-yl)thiomethyl-3-cephem-4-carboxylate.

29. The compound according to claim 1 which is 7-[(Z)-2-(5-amino-1,2,4-thiadiazol-3-yl)-2(2-carboxyprop-2-oxyimino)acetamido]-3-(4,6-diamino-1-propylpylpyrimidinium-2-yl)thiomethyl-3-cephem-4-carboxylate.

30. The compound according to claim 1 which is 7-[(Z)-2-(5-amino-1,2,4-thiadiazol-3-yl)-2-(2-carboxyprop-2-oxyimino)acetamido]-3-(1-butyl-4,6-diaminopyrimidinium-2-yl)thiomethyl-3-cephem-4-carboxylate.

31. The compound according to claim 1 which is 7-[(Z)-2-(2-aminothiazol-4-yl)-2-(2-carboxyprop-2-oxyimino)acetamido]-3-(4,6-diamino-1,5-dimethylpyrimidinium-2-yl)thiomethyl-3-cephem-4-carboxylate.

32. The compound according to claim 1 which is 7-[(Z)-2-(2-aminothiazol-4-yl)-2-(2-carboxyprop-2-oxyimino)acetamido]-3-(4,6-diamino-5-ethyl-1-methylpyrimidinium-2-yl)thiomethyl-3-cephem-4-carboxylate.

33. The compound according to claim 1 which is 7-[(Z)-2-(2-aminothiazol-4-yl)-2-(2-carboxyprop-2-oxyimino)acetamido]-3-(4,6-diamino-1-ethyl-5-methylpyrimidinium-2-yl)thiomethyl-3-cephem-4-carboxylate.

34. The compound according to claim 1 which is 7-[(Z)-2-(2-aminothiazol-4-yl)-2-(2-carboxyprop-2-oxyimino)acetamido]-3-(4,6-diamino-1,5-diethylpyrimidinium-2-yl)thiomethyl-3-cephem-4-carboxylate.

35. The compound according to claim 1 which is 7-[(Z)-2-(2-aminothiazol-4-yl)-2-(2-carboxyprop-2-oxyimino)acetamino]-3-(5-methyl-1,4,6-triaminopyrimidinium-2-yl)thiomethyl-3-cephem-4-carboxylate.

36. The compound according to claim 1 which is 7-(Z)-2-(2-aminothiazol-4-yl)-2-(2-carboxyprop-2-oxyimino)acetamido]-3-(4,6-diamino-1-phenylpyrimidinium-2-yl)thiomethyl-3-cephem-4-carboxylate.

37. The compound according to claim 1 which is 7-[(Z)-2-(2-aminothiazol-4-yl)-2-(2-carboxyprop-2-oxyimino)acetamido]-3-[1-(4-hydroxyphenyl)-4,6-diaminopyrimidinium-2-yl]-thiomethyl-3-cephem-4-carboxylate.

38. The compound according to claim 1 which is 7-[(Z)-2-(2-aminothiazol-4-yl)-2-(carboxymethoxyimino)acetamido]-3-(4,6-diamino-1-phenylpyrimidinium-2-yl)thiomethyl-3-cephem-4-carboxylate.

39. The compound according to claim 1 which is 7-[(Z)-2-(2-aminothiazol-4-yl)-2-(1-carboxyeth-1-oxyimino)acetamido]-3-(4,6-diamino-1-phenylprimidinium-2-yl)thiomethyl-3-cephem-4-carboxylate.

40. The compound according to claim 1 which is 7-[(Z)-2-(2-aminothiazol-4-yl)-2-(ethoxyimino)acetamido]-3-(4,6-diamino-1-phenylpyrimidinium-2-yl) thiomethyl-3-cephem-4-carboxylate.

41. The compound according to claim 1 which is 7-[(Z)-2-(2-aminothiazol-4-yl)-2-(ethoxyimino)acetamido]-3-[1-(4-chlorphenyl)-4,6-diaminopyrimidinium-2-yl]thiomethyl-3-cephem-4-carboxylate.

42. The compound according to claim 1 which is 7-[(Z)-2-(2-aminothiazol-4-yl)-2-(2-carboxyprop-2-oxyimino)acetamido]-3-[4,6-diamino-1-(2,4-dimethylphenyl)-pyrimidinium-2-yl]thiomethyl-3-cephem-4-carboxylate.

43. The compound according to claim 1 which is 7-[(Z)-2-(2-aminothiazol-4-yl)-2-(ethoxyimino)acetamido]-3-(4,6-diamino-1-(2,4-dimethylphenyl)-pyrimidinium-2-yl]thiomethyl-3-cephem-4-carboxylate.

44. The compound according to claim 1 which is 7-[(Z)-2-(2-aminothiazol-4-yl)-2-(2-carboxyprop-2-oxyimino)acetamido]-3-[4,6-diamino-1-(2,6-dimethoxyphenyl)-pyrimidinium-2-yl]thiomethyl-3-cephem-4-carboxylate.

45. The compound according to claim 1 which is 7-[(Z)-2-(2-aminothiazol-4-yl)-2-(2-carboxyprop-2-oxyimino)acetamido]-3-[4,6-diamino-1-(4-chlorophenyl)-pyrimidinium-2-yl]thiomethyl-3-cephem-4-carboxylate.

46. The compound according to claim 1 which is 7-[(Z)-2-(2-aminothiazol-4-yl)-2-(1-carboxyeth-1-oxyimino)acetamido]-3-[4,6-diamino-1-propylpyrimidinium-2-yl]thiomethyl-3-cephem-4-carboxylate.

47. The compound according to claim 1 which is 7-[(Z)-2-(2-aminothiazol-4-yl)-2-(2-propyn-1-oxyimino)acetamido]-3-(4,6-diamino-1-methylpyrimidinium-2-yl)thiomethyl-3-cephem-4-carboxylate.

48. The compound according to claim 1 which is 7-[(Z)-2-(2-aminothiazol-4-yl)-2-(2-propyn-1-oxyimino)acetamido]-3-(4,6-diamino-1-ethylpyrimidinium-2-yl)thiomethyl-3-cephem-4-carboxylate.

49. The compound according to claim 1 which is 7-[(Z)-2-(2-aminothiazol-4-yl)-2-(2-carboxyprop-2- oxyimino)acetamido]-3-(1-cyclopropyl-4,6-diaminopyrimidinium-2yl)-3-cephem-4-carboxylate.

50. The compound according to claim 1 which is 7-[(Z)-2-(2-aminothiazol-4-yl)-2-(2-propen-1-oxyimino)acetamido]-3-(4,6-diamino-1-methyl-pyrimidinium-2-yl)-3-cephem-4-carboxylate.

51. The compound according to claim 1 which is 7-[(Z)-2-(2-aminothiazol-4-yl)-2-(2-propen-1-oxyimino)acetamido]-3-(4,6-diamino-1-ethylpyrimidinium-2-yl)-3-cephem-4-carboxylate.

52. A pharmaceutical composition which comprises a therapeutically effective amount of one or more the cephalosporin compounds of formula (I) recited in claim 1, pharmaceutically acceptable non-toxic slats thereof, or physiologically hydrolyzable esters or solvates thereof as active ingredients, in assoication with pharmaceutically acceptable carriers, excipients or other additives therefor.

53. A cephalosporin compound as recited in claim 1, wherein:

$R^1$ is $C_{1-14}$ alkyl or $-C(CH_3)_2-COOH$;

$R^2$ is $C_{1-4}$ alkyl or $NH_2$;

$R^3$ is hydrogen or methyl; and

Q is N or CH.

54. A cephalosporin compound as recited in claim 1, wherein:

$R^1$ is methyl or $-C(CH_3)_2-COOH$;

$R^2$ is $C_{1-4}$ alkyl or $NH_2$;

$R^3$ is hydrogen or methyl; and

Q is N or CH.

55. A pharmaceutical composition as recited in claim 52, where in the cephalosporin compound of Formula (I):

$R^1$ is methyl or $-C(CH_3)_2-COOH$;

$R^2$ is $C_{1-4}$ alkyl or $NH_2$;

$R^3$ is hydrogen or methyl; and

Q is N or CH.

56. A pharmaceutical composition as recited in claim 52, where in the cephalosporin compound of Formula (I):

$R^1$ is methyl or $-C(CH_3)_2-COOH$;

$R^2$ is methyl or $NH_2$;

$R^3$ is hydrogen or methyl; and

Q is N or CH.

57. A pharmaceutical composition as recited in claim 52, wherein the cephalosporin compound of Formula (I) is: 7-[(Z)-2-(2-aminothiazol-4-yl)-2-(2-carboxyprop-2-oxyimino)acetamido]-3-(1,4,6-triaminopyrimidinium-2-yl)thiomethyl-3-cephem-4-carboxylate.

58. A pharmaceutical composition as recited in claim 52, wherein the cephalosporin compound of Formula (I) is: 7-[(Z)-2-(5-amino-1,2,4-thiadiazol-3-yl)-2-(ethoxyimino)acetamido]-3-(4,6-diamino-1-methylpyrimidinium-2-yl)thiomethyl-3-cephem-4-carboxylate.

* * * * *